(12) United States Patent
Haniuda et al.

(10) Patent No.: US 11,951,103 B2
(45) Date of Patent: Apr. 9, 2024

(54) PHARMACEUTICAL COMPOSITION

(71) Applicant: Kyowa Kirin Co., Ltd., Tokyo (JP)

(72) Inventors: Hiroki Haniuda, Tokyo (JP); Sachiko Enokizono, Tokyo (JP); Tomoyuki Nakazato, Tokyo (JP); Takuya Tokuda, Tokyo (JP); Norie Fujiki, Tokyo (JP)

(73) Assignee: KYOWA KIRIN CO., LTD., Tokyo (JP)

( * ) Notice: Subject to any disclaimer, the term of this patent is extended or adjusted under 35 U.S.C. 154(b) by 528 days.

(21) Appl. No.: 17/106,671

(22) Filed: Nov. 30, 2020

(65) Prior Publication Data

US 2021/0077481 A1 Mar. 18, 2021

Related U.S. Application Data

(63) Continuation of application No. 16/332,033, filed as application No. PCT/JP2017/033161 on Sep. 13, 2017, now Pat. No. 10,894,043.

(30) Foreign Application Priority Data

Sep. 13, 2016 (JP) ................. 2016-178599

(51) Int. Cl.
| | |
|---|---|
| *A61K 31/4709* | (2006.01) |
| *A61K 9/00* | (2006.01) |
| *A61K 9/08* | (2006.01) |
| *A61K 47/02* | (2006.01) |
| *A61K 47/14* | (2017.01) |

(Continued)

(52) U.S. Cl.
CPC ........ *A61K 31/4709* (2013.01); *A61K 9/0048* (2013.01); *A61K 9/08* (2013.01); *A61K 47/02* (2013.01); *A61K 47/14* (2013.01); *A61K 47/38* (2013.01); *A61K 47/40* (2013.01)

(58) Field of Classification Search
CPC .... A61K 31/4709; A61K 9/0048; A61K 9/08; A61K 47/02; A61K 47/14
See application file for complete search history.

(56) References Cited

U.S. PATENT DOCUMENTS

| | | | |
|---|---|---|---|
| 5,145,684 | A | 9/1992 | Liversidge et al. |
| 5,510,118 | A | 4/1996 | Bosch et al. |

(Continued)

FOREIGN PATENT DOCUMENTS

| | | |
|---|---|---|
| CN | 102408418 | 4/2012 |
| JP | 2003-12668 | 1/2003 |

(Continued)

OTHER PUBLICATIONS

Seyfoddin et al., Drug Delivery, (2010) 17:7,467-489 (Year: 2010).*

(Continued)

*Primary Examiner* — San Ming R Hui
(74) *Attorney, Agent, or Firm* — Wenderoth, Lind & Ponack, L.L.P.

(57) ABSTRACT

The present invention relates to a therapeutic agent for an ophthalmic disease comprising a vascular endothelial growth factor (VEGF) receptor inhibitor or an epidermal growth factor (EGF) receptor inhibitor in a nanoparticle form, having a property to be retained in a posterior eye tissue when systemically administered.

33 Claims, 4 Drawing Sheets

(51) Int. Cl.
 *A61K 47/38* (2006.01)
 *A61K 47/40* (2006.01)

(56) References Cited

U.S. PATENT DOCUMENTS

| | | | |
|---|---|---|---|
| 5,518,187 | A | 5/1996 | Bruno et al. |
| 5,718,388 | A | 2/1998 | Czekai et al. |
| 5,862,999 | A | 1/1999 | Czekai et al. |
| 9,353,122 | B2 | 5/2016 | Ong et al. |
| 9,827,248 | B2 | 11/2017 | Ong et al. |
| 9,877,970 | B2 | 1/2018 | Ong et al. |
| 10,034,880 | B2 | 7/2018 | Ochiai et al. |
| 10,154,994 | B2 | 12/2018 | Nguyen et al. |
| 10,398,703 | B2 | 9/2019 | Ong et al. |
| 2006/0052415 | A1 | 3/2006 | Matsunaga et al. |
| 2008/0220075 | A1 | 9/2008 | Merisko-Liversidge et al. |
| 2010/0143346 | A1 | 6/2010 | Richards |
| 2010/0323957 | A1 | 12/2010 | Kuriyan et al. |
| 2013/0316006 | A1 | 11/2013 | Popov et al. |
| 2013/0316601 | A1 | 11/2013 | Kellerman et al. |
| 2013/0316609 | A1 | 11/2013 | Kwon et al. |
| 2014/0235634 | A1 | 8/2014 | Ong et al. |
| 2015/0037422 | A1 | 2/2015 | Kaplan et al. |
| 2015/0125539 | A1 | 5/2015 | Popov et al. |
| 2016/0002254 | A1 | 1/2016 | Ong et al. |
| 2016/0235761 | A1 | 8/2016 | Ong et al. |
| 2016/0237093 | A1 | 8/2016 | Ong et al. |
| 2017/0173161 | A1 | 6/2017 | Kaplan et al. |
| 2017/0296536 | A1 | 10/2017 | Ochiai et al. |
| 2017/0368061 | A1 | 12/2017 | Nguyen et al. |
| 2018/0133225 | A1 | 5/2018 | Ong et al. |
| 2018/0243294 | A1 | 8/2018 | Nguyen et al. |
| 2018/0271782 | A1 | 9/2018 | Popov et al. |

FOREIGN PATENT DOCUMENTS

| | | |
|---|---|---|
| JP | 2004-217649 | 8/2004 |
| JP | 2011-514360 | 5/2011 |
| JP | 2015-519331 | 7/2015 |
| JP | 2016-513108 | 5/2016 |
| WO | 2004/035572 | 4/2004 |
| WO | 2004/060373 | 7/2004 |
| WO | 2009/067548 | 5/2009 |
| WO | 2013/126799 | 8/2013 |
| WO | 2016/039422 | 3/2016 |
| WO | 2016/209555 | 12/2016 |

OTHER PUBLICATIONS

Office Action dated Jul. 13, 2022 in corresponding Australian Patent Application No. 2017326791.

Huu et al., "Light-responsive nanoparticle depot to control release of a small molecule angiogensis inhibitor in the posterior segment of the eye," Journal of Controlled Release, Jan. 2015, vol. 200, pp. 71-77.

Mousa S.A. et al., "Current Status of Vascular Endothelial Growth Factor Inhibition in Age-Related Macular Degeneration", BioDrugs, 2010, vol. 24, No. 3, pp. 183-194.

English translation by Google of WO2004/030676 (Year: 2004).

Cooper, Eugene R., "Nanoparticles: A personal experience for formulating poorly water soluble drugs", Journal of Controlled Release, vol. 141, pp. 300-302, 2010.

Office Action dated Oct. 24, 2023 in corresponding Canadian Patent Application No. 3,036,474.

* cited by examiner

[Figure 1]
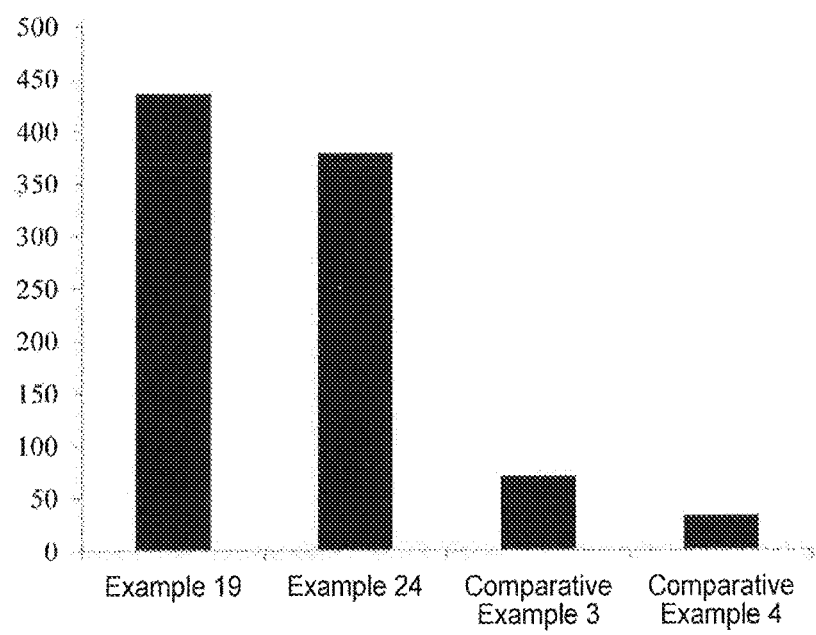
[Figure 2]
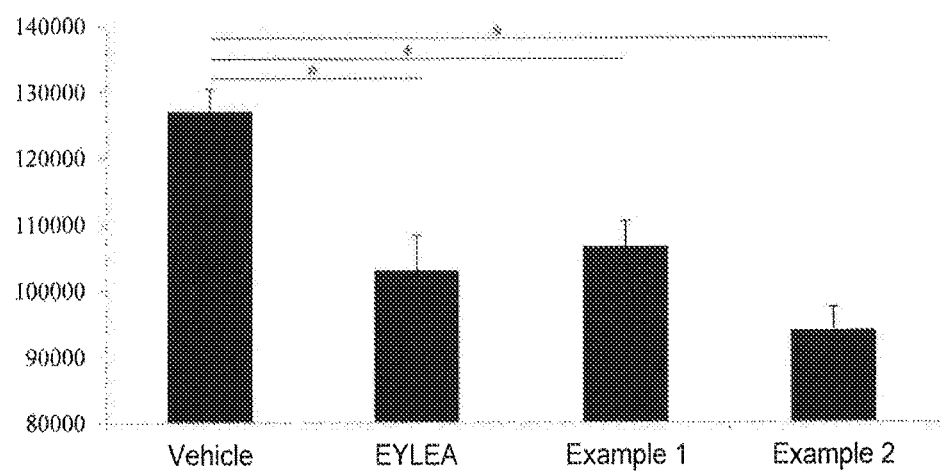

[Figure 3]
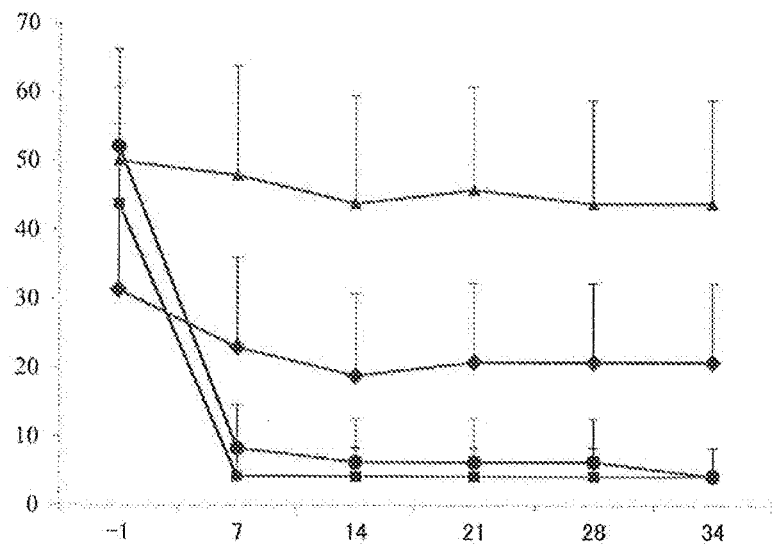
[Figure 4]
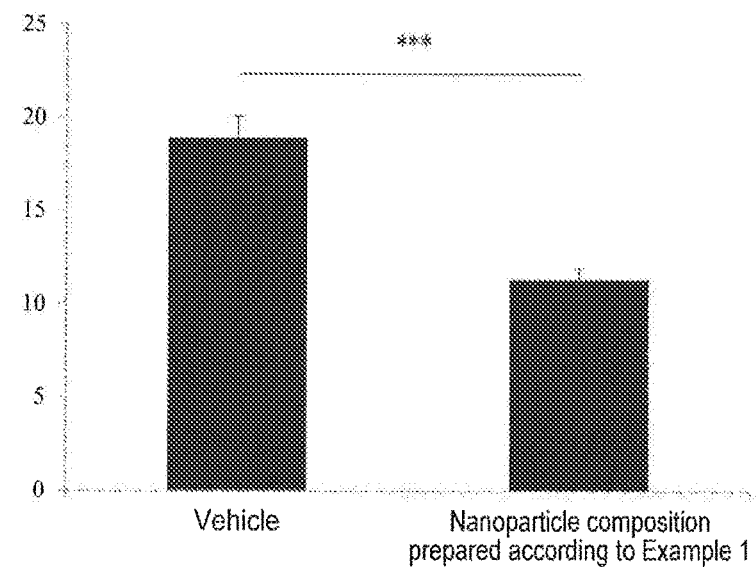

[Figure 5]
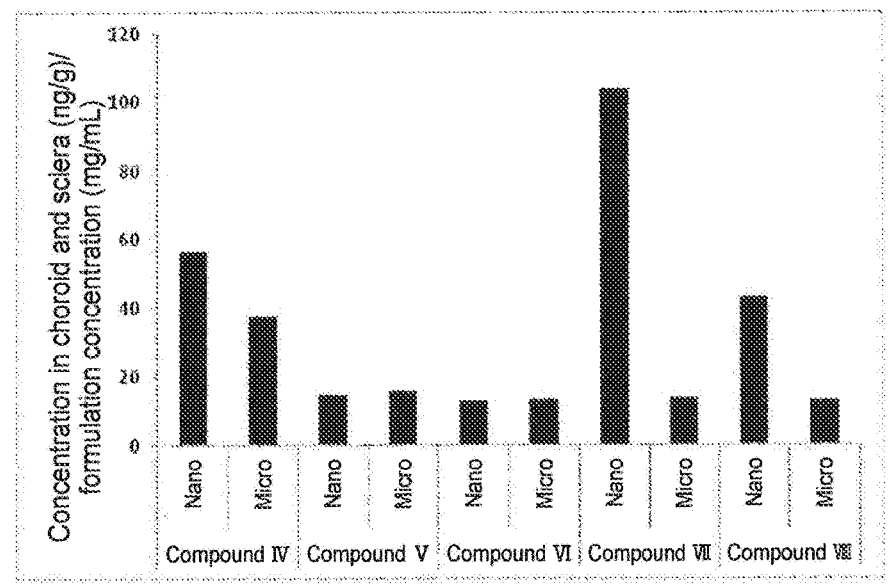
[Figure 6]
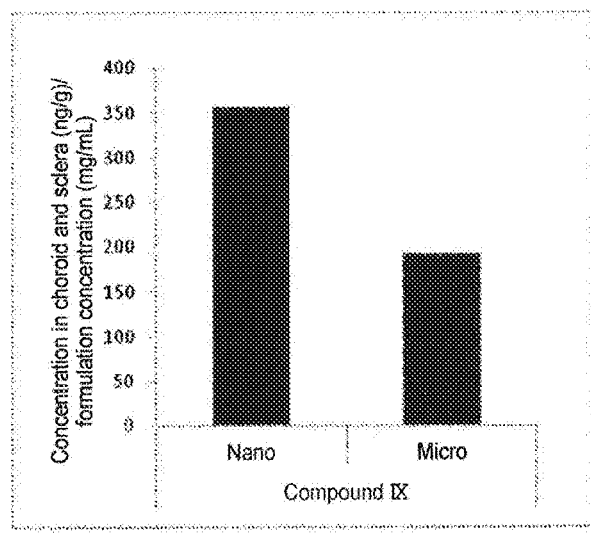

[Figure 7]
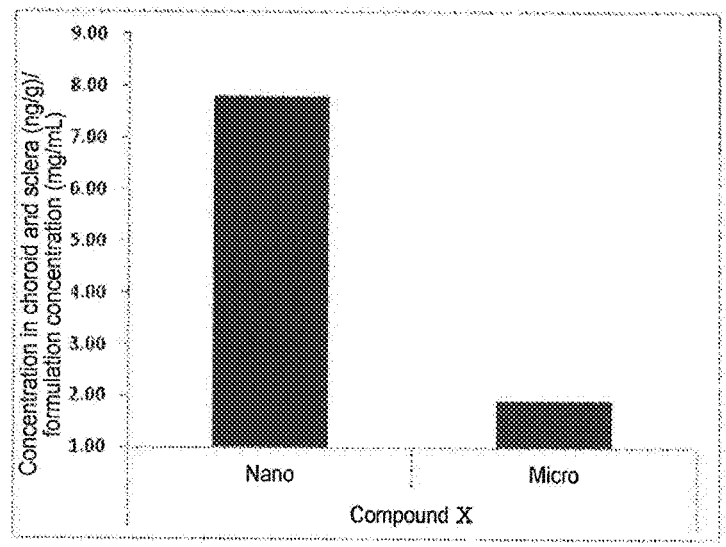

PHARMACEUTICAL COMPOSITION

TECHNICAL FIELD

The present invention relates to a therapeutic agent for an ophthalmic disease, etc. Specifically, the present invention relates to a therapeutic agent for an ophthalmic disease comprising a vascular endothelial growth factor (VEGF) receptor inhibitor or an epidermal growth factor (EGF) receptor inhibitor in a nanoparticle form, etc.

BACKGROUND ART

Research on drug delivery using active ingredients in a nanoparticle form has been actively made in recent Years. Patent Literatures 1 to 4 disclose a pharmaceutical composition comprising an active ingredient in a nanoparticle form. Also, Patent Literatures 5 and 6 disclose a pharmaceutical composition comprising an active ingredient, such as an angiogenesis inhibitor, in a nanoparticle form.

Patent Literature 7 discloses a suspension formulation for eye drops containing (R)-(−)-2-(4-brom-2-fluorobenzyl)-1,2,3,4-tetrahydropyrrolo[1,2-a]pyrazine-4-spiro-3'-pyrrolidine-1,2',3,5'-tetraone (hereinafter, referred to as "compound A") or a physiologically acceptable salt thereof.

However, Patent Literature 7 indicates that compound A is a compound that exhibits an aldose reductase inhibitory effect, but discloses that other suspension formulations of compound B and compound C which also exhibit an aldose reductase inhibitory effect arrived at the retina only slightly. In other words, the technique disclosed in Patent Literature 7 does not indicate that nano-sizing enhances delivery to a posterior eye tissue as to all compounds.

Patent Literature 8 discloses an ophthalmic formulation comprising nanosized particles of nintedanib, pazopanib, or the like in a pharmaceutically effective amount.

However, Patent Literature 8 neither makes specific disclosure about the nano-sizing of nintedanib, pazopanib, or the like nor makes disclosure about any method for nano-sizing each compound.

CITATION LIST

Patent Literature

Patent Literature 1: U.S. Pat. No. 5,518,187
Patent Literature 2: U.S. Pat. No. 5,862,999
Patent Literature 3: U.S. Pat. No. 5,718,388
Patent Literature 4: U.S. Pat. No. 5,510,118
Patent Literature 5: U.S. Pat. No. 5,145,684
Patent Literature 6: Japanese Unexamined Patent Application Publication (Translation of PCT Application) No. 2011-514360
Patent Literature 7: WO 2016/039422
Patent Literature 8: WO 2016/209555

SUMMARY OF INVENTION

Technical Problem

An object of the present invention is to provide a therapeutic agent for an ophthalmic disease comprising a vascular endothelial growth factor (VEGF) receptor inhibitor or an epidermal growth factor (EGF) receptor inhibitor in a nanoparticle form, etc.

Solution to Problem

The present invention is as follows:

(1)
A therapeutic agent for an ophthalmic disease comprising a vascular endothelial growth factor (VEGF) receptor inhibitor or an epidermal growth factor (EGF) receptor inhibitor in a nanoparticle form, having a property to be retained in a posterior eye tissue when systemically administered.

(2)
The therapeutic agent for the ophthalmic disease according to (1), wherein the vascular endothelial growth factor (VEGF) receptor inhibitor or the epidermal growth factor (EGF) receptor inhibitor having a property to be retained in a posterior eye tissue with a half-life of 30 hours or longer in a choroid and/or a sclera when systemically administered.

(3)
The therapeutic agent for the ophthalmic disease according to (1) or (2), wherein, the VEGF receptor inhibitor is a compound represented by formula (I):

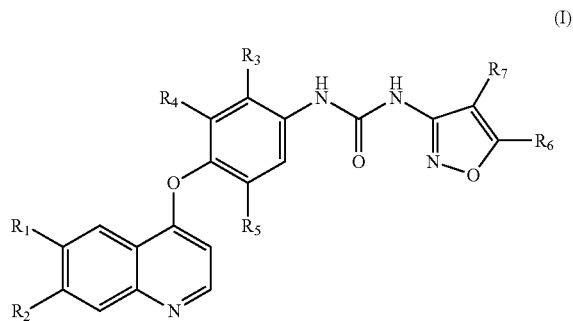

wherein
$R_1$ and $R_2$ are the same or different and each represent a C1-C6 alkoxy group,
$R_3$ represents a halogen atom,
$R_4$ and $R_5$ are the same or different and each represent a hydrogen atom, a halogen atom, a C1-C4 alkyl group, a C1-C4 alkoxy group, a C1-C4 alkylthio group, a trifluoromethyl group, a nitro group or an amino group, and
$R_6$ and $R_7$ are the same or different and each represent a hydrogen atom, a halogen atom, a C1-C4 alkyl group, a C1-C4 alkoxy group, a C1-C4 alkylthio group, a trifluoromethyl group, a nitro group, an amino group, an amino group substituted by one or two C1-C4 alkyl groups, a C1-C4 alkoxycarbonyl-C1-C4 alkyl group, a C1-C4 alkylcarbonyl group or a C3-C5 cycloalkyl group, or a pharmaceutically acceptable salt thereof, or a hydrate or a solvate of the compound or the salt.

(4)
The therapeutic agent for the ophthalmic disease according to (3), wherein $R_4$ and $R_5$ are the same or different and each are a hydrogen atom or a halogen atom, and $R_6$ and $R_7$ are the same or different and each are a hydrogen atom, a halogen atom or a C1-C4 alkyl group.

(5)
The therapeutic agent for the ophthalmic disease according to (3) or (4), wherein $R_3$ is a chlorine atom.

(6)
The therapeutic agent for the ophthalmic disease according to any of (3) to (5), wherein $R_6$ is a C1-C4 alkyl group, and $R_7$ is a hydrogen atom.

(7)
The therapeutic agent for the ophthalmic disease according to any of (3) to (6), wherein each of $R_4$ and $R_5$ is a hydrogen atom.

(8)
The therapeutic agent for the ophthalmic disease according to (1) or (2), wherein the VEGF receptor inhibitor is a compound represented by formula (II):

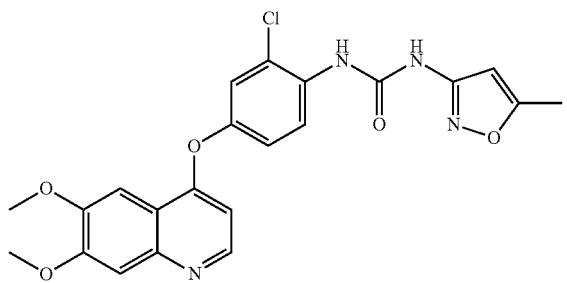

or a pharmaceutically acceptable salt thereof, or a hydrate or a solvate of the compound or the salt.

(9)
The therapeutic agent for the ophthalmic disease according to (1) or (2), wherein the VEGF receptor inhibitor is a compound selected from the group consisting of axitinib, anlotinib, cabozantinib, glesatinib, sunitinib, nintedanib, fruquintinib, rebastinib and lenvatinib, or a pharmaceutically acceptable salt thereof, or a hydrate or solvate of the compound or the salt.

(10)
The therapeutic agent for the ophthalmic disease according to (1) or (2), wherein the EGF receptor inhibitor is a compound selected from the group consisting of avitinib, allitinib, icotinib, erlotinib, osimertinib, N-[2-[[2-(dimethylamino)ethyl]methylamino]-5-[[4-(1H-indol-3-yl)-2-pyrimidinyl]amino]-4-methoxyphenyl]-2-propanamide (AZD-5104), gefitinib, dacomitinib, tesevatinib, nazartinib, varlitinib, brigatinib, poziotinib, lapatinib, 4-[(3-chloro-2-fluorophenyl)amino]-7-methoxyquinazolin-6-yl (2R)-2,4-dimethylpiperazine-1-carboxylate (AZD-3759) and N-(3-chlorophenyl)-N-(6,7-dimethoxyquinazolin-4-yl)amine (AG-1478), or a pharmaceutically acceptable salt thereof, or a hydrate or a solvate of the compound or the salt.

(11)
The therapeutic agent for the ophthalmic disease according to any of (1) to (10), wherein the VEGF receptor inhibitor or the EGF receptor inhibitor has a mean particle size of 20 to 180 nm.

(12)
The therapeutic agent for the ophthalmic disease according to any of (1) to (11), further comprising one or more components selected from a thickening agent, a surfactant and a dispersion media.

(13)
The therapeutic agent for the ophthalmic disease according to (12), wherein the thickening agent is one or more substances selected from carboxyvinyl polymer, carboxymethylcellulose calcium, carboxymethylcellulose sodium, povidone, partially hydrolyzed polyvinyl alcohol, hydroxypropylcellulose, hydroxypropylmethylcellulose, hydroxypropylmethylcellulose phthalate, hydroxyethylcellulose, amorphous cellulose, methylcellulose, magnesium aluminum silicate and triethanolamine.

(14)
The therapeutic agent for the ophthalmic disease according to (12) or (13), wherein the surfactant is one or more substances selected from polyoxyethylene castor oil, polyoxyl 40 stearate, sucrose stearate, polyoxyethylene sorbitan monolaurate, polyoxyethylene sorbitan monostearate, polyoxyethylene sorbitan tristearate, polyoxyethylene sorbitan monooleate, polyoxyethylene sorbitan trioleate, sorbitan monolaurate, L-α-phosphatidylcholine (PC), 1,2-dipalmitoylphosphatidylcholine (DPPC), oleic acid, natural lecithin, synthetic lecithin, polyoxyethylene oleyl ether, polyoxyethylene lauryl ether, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol, tyloxapol, octylphenol ethoxylate, alkyl glucoside and poloxamer.

(15)
The therapeutic agent for the ophthalmic disease according to any of (12) to (14), wherein the dispersion media is water, an alcohol, liquid paraffin, water containing a solute, an alcohol containing a solute or liquid paraffin containing a solute.

(16)
The therapeutic agent for the ophthalmic disease according to any of (12) to (14), wherein the dispersion media is water containing a solute.

(17)
The therapeutic agent for the ophthalmic disease according to (15) or (16), wherein the solute is one or more substances selected from sodium chloride, glucose, glycerol, mannitol, sodium dihydrogen phosphate, dibasic sodium phosphate hydrate, sodium bicarbonate, trishydroxymethylaminomethane, citric acid hydrate, boric acid and borax.

(18)
The therapeutic agent for the ophthalmic disease according to any of (1) to (17), further comprising one or more components selected from a preservative and an inclusion substance.

(19)
The therapeutic agent for the ophthalmic disease according to (18), wherein the preservative is one or more substances selected from benzalkonium chloride, methyl parahydroxybenzoate, propyl parahydroxybenzoate, chlorobutanol, disodium edetate hydrate, chlorhexidine gluconate and sorbic acid.

(20)
The therapeutic agent for the ophthalmic disease according to (18) or (19), wherein the inclusion substance is one or more substances selected from α-cyclodextrin, β-cyclodextrin, 2-hydroxypropyl-β-cyclodextrin and γ-cyclodextrin.

(21)
The therapeutic agent for the ophthalmic disease according to any of (1) to (20), wherein the therapeutic agent for the ophthalmic disease is intended to be used for topical ocular administration.

(22)
The therapeutic agent for the ophthalmic disease according to (21), wherein the topical ocular administration is ocular instillation, subconjunctival administration, sub-Tenon administration, intravitreal administration, suprachoroidal administration, periocular administration or administration using an intraocular implant.

(23)
The therapeutic agent for the ophthalmic disease according to any of (1) to (22), wherein the therapeutic agent for the ophthalmic disease is a liquid formulation.
(24)
The therapeutic agent for the ophthalmic disease according to any of (1) to (23), wherein the therapeutic agent for the ophthalmic disease is eye drops.
(25)
The therapeutic agent for the ophthalmic disease according to any of (1) to (24), wherein the ophthalmic disease is a vascular endothelial growth factor (VEGF)-related disease or an epidermal growth factor (EGF)-related disease.
(26)
The therapeutic agent for the ophthalmic disease according to (25), wherein the VEGF-related disease is wet age-related macular degeneration, dry age-related macular degeneration, choroidal neovascularization, myopic choroidal neovascularization, branch retinal vein occlusion, macular edema, macular edema following central retinal vein occlusion, diabetic macular edema, proliferative diabetic retinopathy, neovascular glaucoma, angioid streaks of the retina, retinopathy of prematurity, Coats disease, branch retinal vein occlusion, central retinal vein occlusion, cystoid macular edema, vitreous hemorrhage caused by diabetic retinopathy, Eales disease, central serous chorioretinopathy, epiretinal membrane, uveitis, multifocal choroiditis, anterior ischemic optic neuropathy, corneal neovascularization, pterygium, intraocular melanoma, vasoproliferative tumor of the retina, radiation retinopathy, tuberous sclerosis, vasoproliferative tumor of the retina, conjunctival squamous cell carcinoma or ocular hypertension.
(27)
The therapeutic agent for the ophthalmic disease according to (26), wherein the VEGF-related disease is wet age-related macular degeneration, myopic choroidal neovascularization, branch retinal vein occlusion, central retinal vein occlusion, macular edema following central retinal vein occlusion, diabetic macular edema, proliferative diabetic retinopathy or neovascular glaucoma.
(28)
The therapeutic agent for the ophthalmic disease according to (25), wherein the EGF-related disease is wet age-related macular degeneration, dry age-related macular degeneration, choroidal neovascularization, myopic choroidal neovascularization, macular edema, macular edema following central retinal vein occlusion, diabetic macular edema, proliferative diabetic retinopathy, glaucoma, neovascular glaucoma, ocular inflammation, retinoblast, branch retinal vein occlusion, central retinal vein occlusion, retinopathy of prematurity, angioid streaks of the retina, retinal artery obstruction, corneal neovascularization, pterygium, uveal melanoma, uveitis, epiretinal membrane, corneal subepithelial fibrosis, dry eye or meibomian gland dysfunction.
(29)
The therapeutic agent for the ophthalmic disease according to (25), wherein the EGF-related disease is wet age-related macular degeneration, myopic choroidal neovascularization, branch retinal vein occlusion, central retinal vein occlusion, macular edema following central retinal vein occlusion, diabetic macular edema, proliferative diabetic retinopathy or neovascular glaucoma.
(30)
A method for treating a vascular endothelial growth factor (VEGF)-related disease or an epidermal growth factor (EGF)-related disease, comprising administering a therapeutic agent for an ophthalmic disease according to any of (1) to (29).
(31)
A method for producing a therapeutic agent for an ophthalmic disease according to any of (1) to (29), comprising the step of milling a vascular endothelial growth factor (VEGF) receptor inhibitor or an epidermal growth factor (EGF) receptor inhibitor into a nanoparticle form.
(32)
The method according to (31), wherein the milling step further comprises adding one or more components selected from a thickening agent, a surfactant and a dispersion media, followed by the milling.
(33)
The method according to (31) or (32), wherein the milling step further comprises adding one or more components selected from a preservative and an inclusion substance, followed by the milling.
(34)
The method according to any of (31) to (33), wherein the milling is wet milling.
(35)
The method according to (33), wherein the wet milling comprises the step of adding a dispersion media to the vascular endothelial growth factor (VEGF) receptor inhibitor or the epidermal growth factor (EGF) receptor inhibitor, followed by the milling.

Advantageous Effects of Invention

The present invention can provide a therapeutic agent for an ophthalmic disease comprising a vascular endothelial growth factor (VEGF) receptor inhibitor or an epidermal growth factor (EGF) receptor inhibitor in a nanoparticle form, etc.

BRIEF DESCRIPTION OF DRAWINGS

FIG. 1 The pharmaceutical compositions (nanoparticle compositions) of the present invention obtained in Examples 19 and 24 and microparticle compositions obtained in Comparative Examples 3 and 4 were evaluated for their pharmacokinetics when administered at a single dose by ocular instillation (4 to 12 µL/eye) to rats. The ordinate depicts the concentration (ng/g) of compound II in the choroid and the sclera, and the abscissa depicts Example and Comparative Example Nos.

FIG. 2 A vehicle and the pharmaceutical compositions (nanoparticle compositions) of the present invention obtained in Examples 1 and 2 were evaluated for their anti-angiogenic effects when administered twice a day by ocular instillation to rats from immediately after laser irradiation to 14 days after the laser irradiation. Aflibercept (EYLEA(Registered Trademark) solution for intravitreal injection, Bayer Corp.) was intravitreally injected to rat eyes immediately after laser irradiation and evaluated for its anti-angiogenic effect 14 days after the administration. The ordinate depicts a choroidal neovascularization area (pixel), and the abscissa depicts the name of the administered substance or Example No. * represents significant difference (p<0.05) in the Dunnet test on the aflibercept, Example 1 and Example 2 administration groups vs. the vehicle group.

FIG. 3 Laser-induced choroidal neovascularization models were prepared by the laser irradiation of cynomolgus monkey eyes. Choroidal neovascular grading was carried out on an irradiation spot basis by fluorescein fundus angiography to calculate the incidence of grade 4 (clear hyperfluorescence at the first or middle stage of angiography and fluorescent leakage at the late stage except for the injured region). A vehicle, the pharmaceutical composition (nanoparticle composition) of the present invention prepared according to Example 1, and a solution composition obtained in Comparative Example 2 were evaluated for their anti-angiogenic effects when administered four times a day by ocular instillation to the animal models for 35 days. Aflibercept (EYLEA(Registered Trademark) solution for intravitreal injection, Bayer Corp.) was intravitreally injected to the animal models and evaluated for its anti-angiogenic effect up to 35 days after the administration. The ordinate depicts the incidence of grade 4 (% of grade 4 lesion), and the abscissa depicts the drug administration period or the period after the administration (e.g., −1 refers to the day before the start of administration, and 7 refers to the 7th day after the start of administration). The filled rhomboid depicts the Example 1 vehicle administration group, the filled circle depicts the Example 1 administration group, the filled triangle depicts the Comparative Example 2 administration group, and the filled square depicts the aflibercept administration group.

FIG. 4 A vehicle and the pharmaceutical composition (nanoparticle composition) of the present invention prepared according to Example 1 were evaluated for their anti-angiogenic effects on the retina when administered twice a day by ocular instillation to immature mice for 5 days before which the immature mice were subjected to high-oxygen loading treatment (under 75% oxygen, 5 days) and then placed under normal oxygen for the administration. The ordinate depicts a neovascular area (the ratio of a neovascular area to the total tissue area of the retina; %) in the retina, and the abscissa depicts the name of the administered substance or Example No. *** represents significant difference (p<0.001) in the unpaired t-test on the administration group of the pharmaceutical composition (nanoparticle composition) of the present invention prepared according to Example 1 vs. the vehicle group.

FIG. 5 The pharmaceutical compositions (nanoparticle compositions) of the present invention containing compounds IV to VIII, obtained according to Example 101, Example 108, Example 112, Reference Example 9 and Reference Example 10, and microparticle compositions containing compounds IV to VIII, obtained in Comparative Examples 6, 7, 8, 9 and 10 were evaluated for their pharmacokinetics when administered at a single dose by ocular instillation (5 μL/eye) to rats. The ordinate depicts values obtained by dividing the concentrations (ng/g) of compounds IV to VIII in the choroid and the sclera by formulation concentrations (mg/mL), and the abscissa depicts compound Nos. and particle size.

FIG. 6 The pharmaceutical composition (nanoparticle composition) of the present invention containing compound IX, obtained in Example 145, and a microparticle composition obtained in Comparative Example 16 were evaluated for their pharmacokinetics when administered at a single dose by ocular instillation (5 μL/eye) to rats. The ordinate depicts a value obtained by dividing the concentration (ng/g) of compound IX in the choroid and the sclera by a formulation concentration (mg/mL), and the abscissa depicts compound Nos. and particle size.

FIG. 7 The pharmaceutical composition (nanoparticle composition) of the present invention containing compound X, obtained in Example 153, and a microparticle composition obtained in Comparative Example 17 were evaluated for their pharmacokinetics when administered at a single dose by ocular instillation (5 μL/eye) to rats. The ordinate depicts a value obtained by dividing the concentration (ng/g) of compound X in the choroid, and the sclera by a formulation concentration (mg/mL), and the abscissa depicts compound Nos. and particle size.

DESCRIPTION OF EMBODIMENTS

The therapeutic agent for the ophthalmic disease of the present invention comprises, as an active ingredient, a vascular endothelial growth factor (VEGF) receptor inhibitor or an epidermal growth factor (EGF) receptor inhibitor having a property to be retained in a posterior eye tissue when systemically administered.

The vascular endothelial growth factor (VEGF) receptor inhibitor is not particularly limited, and a substance known in the art can be used which has inhibitory activity against vascular endothelial growth factor (VEGF) receptor and has a property to be retained in a posterior eye tissue when systemically administered.

The epidermal growth factor (EGF) receptor inhibitor is not particularly limited, and a substance known in the art can be used which has inhibitory activity against epidermal growth factor (EGF) receptor and has a property to be retained in a posterior eye tissue when systemically administered.

The therapeutic agent for the ophthalmic disease may comprise one vascular endothelial growth factor (VEGF) receptor inhibitor or may comprise two or more vascular endothelial growth factor (VEGF) receptor inhibitors.

The therapeutic agent for the ophthalmic disease may comprise one epidermal growth factor (EGF) receptor inhibitor or may comprise two or more epidermal growth factor (EGF) receptor inhibitors.

The therapeutic agent for the ophthalmic disease may comprise one or more vascular endothelial growth factor (VEGF) receptor inhibitors and one or more epidermal growth factor (EGF) receptor inhibitors.

The "posterior eye tissue" in the "property to be retained in a posterior eye tissue when systemically administered" for the vascular endothelial growth factor (VEGF) receptor inhibitor or the epidermal growth factor (EGF) receptor inhibitor used in the therapeutic agent for the ophthalmic disease of the present invention refers to the choroid, the retina, the sclera, or the optic nerve and preferably refers to the choroid and/or the sclera or the retina, more preferably the choroid and/or the sclera. The "property to be retained" in the "property to be retained in a posterior eye tissue when systemically administered" for the vascular endothelial growth factor (VEGF) receptor inhibitor or the epidermal growth factor (EGF) receptor inhibitor used in the therapeutic agent for the ophthalmic disease of the present invention specifically means that the compound has a half-life of 30 hours or longer in the choroid and/or the sclera when administered (preferably by intravenous injection) to a Brown Norway rat. The half-life in the choroid and/or the sclera is preferably 35 hours or longer, more preferably 40 hours or longer. In this context, the compound that remains in the posterior eye tissue (choroid and/or sclera, retina, etc.) localizes longer near the target (VEGF receptor or EGF receptor) in the tissue, as compared with a compound that does not remain therein. Thus, an effect based on the mechanism of action of the compound (inhibitory effect on the phosphorylation of VEGF receptor or EGF receptor) is maintained for a longer time. Finally, its pharmacological effects (angiogenesis inhibitory effect, suppressive effect on increase in vascular permeability, and other pharmacological effects based on the inhibitory effect on the phosphorylation of VEGF receptor or EGF receptor) are more strongly exerted. Furthermore, the compound that remains in the posterior eye tissue accumulates in the tissue by continuous (repetitive) administration and increases its exposure in the tissue, as compared with a compound that does not remain therein. As a result of these effects, the pharmacological effects of the compound are more strongly exerted in the posterior eye tissue.

Examples of the systemic administration method include, but are not particularly limited to, oral administration, intravenous injection, intramuscular injection or subcutaneous injection, sublingual administration, transnasal administration, ocular instillation, inhalation, and transdermal administration. Oral administration, intravenous injection, intramuscular injection or subcutaneous injection, or ocular instillation is preferred, and oral administration or intravenous injection is more preferred. The recipient of the systemic administration is not particularly limited as long as the recipient is a mammal. A human, a monkey (e.g., a cynomolgus monkey), a rabbit (e.g., Kbl:Dutch), a mouse (e.g., 129SVE), or a rat (e.g., Brown Norway) is preferred, and a human, a monkey, or a rat is more preferred.

Whether or not the compound has the property to be retained in a posterior eye tissue when systemically administered can be determined by, for example, the following approach: the vascular endothelial growth factor (VEGF) receptor inhibitor or the epidermal growth factor (EGF) receptor inhibitor is dissolved in an organic solvent such as dimethylacetamide (DMA) and then diluted with saline containing polyoxyethylene sorbitan monooleate (polysorbate 80 or Tween 80) or the like to prepare an intravenous dosing solution. This intravenous dosing solution is administered to a Brown Norway rat. After a given interval from the administration, for example, 24, 72 and 168 hours after the administration, blood is collected. Then, the rat is euthanized while the eyeballs are excised. A posterior eye tissue such as the choroid and/or the sclera, the retina, or the optic nerve is harvested therefrom. A given amount of an aqueous solution containing an organic solvent (e.g., a 50 vol % methanol solution) is added to the harvested posterior eye tissue, which is then homogenized, for example, to prepare an assay sample. The drug concentration in this assay sample can be measured using a liquid chromatograph-tandem mass spectrometer (LC/MS/MS) to measure the compound concentration in the posterior eye tissue in the case of systemic administration. The elimination half-life of the compound in the posterior eye tissue can be further calculated from time-dependent change in compound concentration in the posterior eye tissue.

Examples of the vascular endothelial growth factor (VEGF) receptor inhibitor that may be used as a therapeutic agent for an ophthalmic disease in a nanoparticle form include a compound represented by formula (I) or formula (II), a pharmaceutically acceptable salt of the compound represented by formula (I) or formula (II), a hydrate of the compound represented by formula (I) or formula (II), a solvate of the compound represented by formula (I) or formula (II), a hydrate of the pharmaceutically acceptable salt of the compound represented by formula (I) or formula (II), and a solvate of the pharmaceutically acceptable salt of the compound represented by formula (I) or, formula (II). Examples of the vascular endothelial growth factor (VEGF) receptor inhibitor that may be used as a therapeutic agent for an ophthalmic disease in a nanoparticle form include axitinib, cabozantinib, regorafenib, ponatinib, lenvatinib, sunitinib, sorafenib, pazopanib, vandetanib, nintedanib, ginsenoside Rg3 (Jilin Yatai Pharmaceuticals Co., Ltd.), apatinib, anlotinib, fruquintinib, famitinib, sulfatinib, muparfostat (Medigen Biotechnology Corp.), rebastinib, glesatinib, X-82 (Tyrogenex, Inc.), ODM-203 (Orion Corp.), PAN-90806 (PanOptica, Inc.), lucitanib, TAS-115 (Taiho Pharmaceutical Co., Ltd.), ENMD-2076 (CAST Pharmaceuticals Inc.), albendazole, fenretinide, AN-019 (Natco Pharma Ltd.), CTO (Tactical Therapeutics, Inc.), puquitinib, their pharmaceutically acceptable salts, and hydrates and solvates of these compounds or the salts.

Among them, examples of the vascular endothelial growth factor (VEGF) receptor inhibitor having a property to be retained in a posterior eye tissue when systemically administered include a compound represented by formula (I) or formula (II), a pharmaceutically acceptable salt of the compound represented by formula (I) or formula (II), a hydrate of the compound represented by formula (I) or formula (II), a solvate of the compound represented by formula (I) or formula (II), a hydrate of the pharmaceutically acceptable salt of the compound represented by formula (I) or formula (II), and a solvate of the pharmaceutically acceptable salt of the compound represented by formula (I) or formula (II). Examples of the VEGF receptor inhibitor having a property to be retained in a posterior eye tissue when systemically administered include axitinib, anlotinib, cabozantinib, glesatinib, sunitinib, nintedanib, fruquintinib, rebastinib, lenvatinib, their pharmaceutically acceptable salts, and hydrates and solvates of these compounds or the salts.

Examples of the epidermal growth factor (EGF) receptor inhibitor that may be used as a therapeutic agent for an ophthalmic disease in a nanoparticle form include osimertinib, erlotinib, lapatinib, icotinib, gefitinib, afatinib, olmutinib, AZD-3759 (AstraZeneca plc), allitinib, nazartinib, tesevatinib, poziotinib, dacomitinib, varlitinib, avitinib, S-222611 (Shionogi & Co., Ltd.), brigatinib, AP-32788 (ARIAD Pharmaceuticals, Inc.), neratinib, naguotinib, agerafenib, PF-06747775 (Pfizer Inc.), theliatinib, SKLB-1028 (Sichuan University), NRC-2694-A (Natco Pharma Ltd.), epitinib, Hemay-020 (Tianjin Hemay Bio-Tech Co., Ltd.), PB-357 (Puma Biotechnology/Pfizer Inc.), tucatinib, TAS-121 (Taiho Pharmaceutical Co., Ltd.), QLNC-120 (Qilu Pharmaceutical Co., Ltd.), pirotinib, Hemay-022 (Tianjin Hemay Bio-Tech Co., Ltd.), simotinib, AG-1478, their pharmaceutically acceptable salts, and hydrates and solvates of these compounds or the salts.

Among them, examples of the epidermal growth factor (EGF) receptor inhibitor having a property to be retained in a posterior eye tissue when systemically administered include avitinib, allitinib, icotinib, erlotinib, osimertinib, N-[2-[[2-(dimethylamino)ethyl]methylamino]-5-[[4-(1H-indol-3-yl)-2-pyrimidinyl]amino]-4-methoxyphenyl]-2-propanamide (AZD-5104), gefitinib, dacomitinib, tesevatinib, nazartinib, varlitinib, brigatinib, poziotinib, lapatinib, 4-[(3-chloro-2-fluorophenyl)amino]-7-methoxyquinazolin-6-yl (2R)-2,4-dimethylpiperazine-1-carboxylate (AZD-3759), N-(3-chlorophenyl)-N-(6,7-dimethoxyquinazolin-4-yl) amine (AG-1478), their pharmaceutically acceptable salts, and hydrates and solvates of these compounds or the salts.

Examples of the vascular endothelial growth factor (VEGF) receptor inhibitor comprised in the therapeutic agent for the ophthalmic disease of the present invention include a compound represented by formula (I):

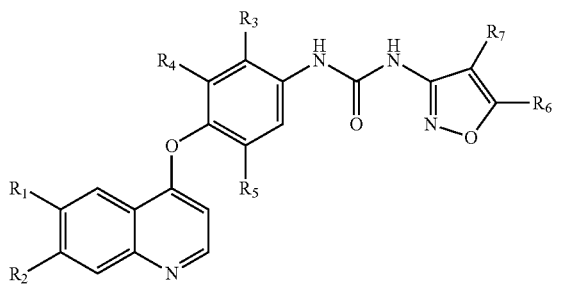

(I)

wherein
- $R_1$ and $R_2$ are the same or different and each represent a C1-C6 alkoxy group,
- $R_3$ represents a halogen atom,
- $R_4$ and $R_5$ are the same or different and each represent a hydrogen atom, a halogen atom, a C1-C4 alkyl group, a C1-C4 alkoxy group, a C1-C4 alkylthio group, a trifluoromethyl group, a nitro group or an amino group, and
- $R_6$ and $R_7$ are the same or different and each represent a hydrogen atom, a halogen atom, a C1-C4 alkyl group, a C1-C4 alkoxy group, a C1-C4 alkylthio group, a trifluoromethyl group, a nitro group, an amino group, an amino group substituted by one or two C1-C4 alkyl groups, a C1-C4 alkoxycarbonyl-C1-C4 alkyl group, a C1-C4 alkylcarbonyl group or a C3-C5 cycloalkyl group, and a pharmaceutically acceptable salt thereof, and a hydrate and a solvate of the compound or the salt.

The vascular endothelial growth factor (VEGF) receptor inhibitor is a compound represented by formula (I), a pharmaceutically acceptable salt of the compound represented by formula (I), a hydrate of the compound represented by formula (I), a solvate of the compound represented by formula (I), a hydrate of the pharmaceutically acceptable salt of the compound represented by formula (I), or a solvate of the pharmaceutically acceptable salt of the compound represented by formula (I).

In formula (I), $R_1$ and $R_2$ are the same or different and each represent a C1-C6 alkoxy group. Each of $R_1$ and $R_2$ is preferably a methoxy group.

In formula (I), $R_3$ represents a halogen atom and is preferably a chlorine atom.

In formula (I), $R_4$ and $R_5$ are the same or different and each represent a hydrogen atom, a halogen atom, a C1-C4 alkyl group, a C1-C4 alkoxy group, a C1-C4 alkylthio group, a trifluoromethyl group, a nitro group or an amino group. $R_4$ and $R_5$ are the same or different and each are preferably a hydrogen atom or a halogen atom, more preferably a hydrogen atom or a halogen atom, further preferably a hydrogen atom.

In formula (I), $R_6$ and $R_7$ are the same or different and each represent a hydrogen atom, a halogen atom, a C1-C4 alkyl group, a C1-C4 alkoxy group, a C1-C4 alkylthio group, a trifluoromethyl group, a nitro group, an amino group, an amino group substituted by one or two C1-C4 alkyl groups, a C1-C4 alkoxycarbonyl-C1-C4 alkyl group, a C1-C4 alkylcarbonyl group or a C3-C5 cycloalkyl group. $R_6$ and $R_7$ are the same or different and each are preferably a hydrogen atom, a halogen atom, a C1-C4 alkyl group or a C1-C4 alkoxy group. More preferably, $R_6$ is a C1-C4 alkyl group, and $R_7$ is a hydrogen atom. Further preferably, $R_6$ is a methyl group, and $R_7$ is a hydrogen atom.

For the combination of these substituents in formula (I), preferably, $R_4$ and $R_5$ are the same or different and each are a hydrogen atom or a halogen atom, and $R_6$ and $R_7$ are the same or different and each are a hydrogen atom, a halogen atom or a C1-C4 alkyl group. More preferably, $R_3$ is a chlorine atom, $R_4$ and $R_5$ are the same or different and each are a hydrogen atom or a halogen atom, and $R_6$ and $R_7$ are the same or different and each are a hydrogen atom, a halogen atom or a C1-C4 alkyl group. Further preferably, $R_3$ is a chlorine atom, each of $R_4$ and $R_5$ is a hydrogen atom, $R_6$ is a C1-C4 alkyl group, and $R_7$ is a hydrogen atom.

The vascular endothelial growth factor (VEGF) receptor inhibitor is preferably a compound represented by formula (II):

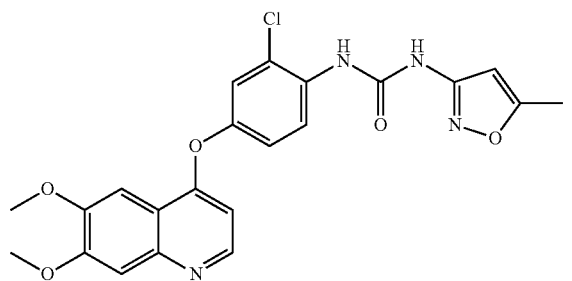

(II)

or a pharmaceutically acceptable salt thereof, or a hydrate or a solvate of the compound or the salt.

The compound represented by formula (I) or the compound represented by formula (II) according to the present invention can be produced by a method disclosed in Japanese Unexamined Patent Application Publication No 2003-12668, or a method equivalent thereto.

The vascular endothelial growth factor (VEGF) receptor inhibitor comprised in the therapeutic agent for the ophthalmic disease of the present invention is as mentioned above and includes the compound described above (free form), a pharmaceutically acceptable salt thereof, and a hydrate and a solvate of the compound or the salt.

The vascular endothelial growth factor (VEGF) receptor inhibitor according to the present invention can be produced by a conventional method known in the art, or a method equivalent thereto.

When the vascular endothelial growth factor (VEGF) receptor inhibitor is a compound represented by formula (I) or a compound represented by formula (II), the compound can be produced by a method disclosed in Japanese Unexamined Patent Application Publication No. 2003-12668, or a method equivalent thereto.

The epidermal growth factor (EGF) receptor inhibitor according to the present invention can be produced by a conventional method known in the art, or a method equivalent thereto.

When the vascular endothelial growth factor (VEGF) receptor inhibitor or the epidermal growth factor (EGF) receptor inhibitor used in the present invention is a pharmaceutically acceptable salt, examples thereof include: hydrohalides such as hydrochloride, hydrofluoride, hydrobromide, and hydroiodide; inorganic acid salts such as sulfate, phosphate, nitrate, and perchlorate; organic acid salts such as acetate, citrate, fumarate, succinate, tartrate, oxalate, maleate, malate, lactate, and ascorbate, lower alkylsulfonates such as mesylate, trifluoromethanesulfonate, and ethanesulfonate; arylsulfonates such as benzenesulfonate and tosylate; amino acid salts such as glycinate, phenylalanate, glutamate, and aspartate, alkali metal salts such as sodium salt and potassium salt; alkaline earth metal salts such as calcium salt and magnesium salt; and organic base salts such as amine salt.

The compound represented by formula (I) or the pharmaceutically acceptable salt thereof according to the present invention includes all of intramolecular salts and adducts thereof, solvates and hydrates of the compound, the salt, or these substances, etc.

The vascular endothelial growth factor (VEGF) receptor inhibitor or the epidermal growth factor (EGF) receptor inhibitor used in the present invention may be a compound (free form) or a pharmaceutically acceptable salt thereof, or a hydrate or a solvate of the compound or the salt.

The hydrate of the compound or the pharmaceutically acceptable salt is not particularly limited by the number of water molecules for hydration and can be monohydrate, dihydrate, or trihydrate.

The solvate of the compound or the pharmaceutically acceptable salt is not particularly limited by the number of solvent molecules for solvation and can be monosolvate, disolvate, or trisolvate.

Examples of the solvent for solvation include alcohols such as methanol and ethanol. Examples of the solvate of the compound or the pharmaceutically acceptable salt include alcohol solvates such as methanol solvate and ethanol solvate.

When the vascular endothelial growth factor (VEGF) receptor inhibitor used in the present invention is a compound represented by formula (I) or a pharmaceutically acceptable salt thereof, or a hydrate or a solvate of the compound or the salt, a free form, an inorganic acid salt or an organic acid salt, or a hydrate of the free form or the inorganic acid salt or the organic acid salt is preferred, and hydrochloride of the compound represented by formula (I) or a hydrate of the hydrochloride of the compound represented by formula (I) is more preferred.

In the present invention, the vascular endothelial growth factor (VEGF) receptor inhibitor is more preferably hydrochloride of the compound represented by formula (II) or a hydrate of the hydrochloride of the compound represented by formula (II).

The therapeutic agent for the ophthalmic disease of the present invention, which comprises the vascular endothelial growth factor (VEGF) receptor inhibitor or the epidermal growth factor (EGF) receptor inhibitor in a nanoparticle form, may comprise a vascular endothelial growth factor (VEGF) receptor inhibitor or an epidermal growth factor (EGF) receptor inhibitor in a form other than the nanoparticle form.

Examples of the form other than the nanoparticle form include a microparticle form.

In the therapeutic agent for the ophthalmic disease of the present invention, the content of the vascular endothelial growth factor (VEGF) receptor inhibitor or the epidermal growth factor (EGF) receptor inhibitor in a form other than the nanoparticle form can be 20% by mass or less of the content of the vascular endothelial growth factor (VEGF) receptor inhibitor or the epidermal growth factor (EGF) receptor inhibitor in a nanoparticle form.

The content of the nanoparticle form is preferably 60% by mass to 100% by mass, more preferably 70% by mass to 100% by mass, further preferably 80% by mass to 100% by mass, with respect to the total amount of the vascular endothelial growth factor (VEGF) receptor inhibitor or the epidermal growth factor (EGF) receptor inhibitor.

In the present invention, the nanoparticle form means that the substance is in a particle form of nanometer order and generally means that the substance is in a particle form having a mean particle size of 10 to 1000 nm.

The vascular endothelial growth factor (VEGF) receptor inhibitor or the epidermal growth factor (EGF) receptor inhibitor in a nanoparticle form comprised in the therapeutic agent for the ophthalmic disease of the present invention is preferably prepared by milling or crystallization.

The mean particle size of the vascular endothelial growth factor (VEGF) receptor inhibitor or the epidermal growth factor (EGF) receptor inhibitor in a nanoparticle form comprised in the therapeutic agent for the ophthalmic disease of the present invention is not particularly limited as long as the mean particle size is 400 nm or smaller. The mean particle size is preferably 10 to 400 nm, more preferably 10 to 300 nm, further preferably 10 to 200 nm, still further preferably 20 to 180 nm or smaller, still further preferably 30 to 150 nm or smaller, particularly preferably 50 to 130 nm or smaller.

The method for measuring the mean particle size of the vascular endothelial growth factor (VEGF) receptor inhibitor or the epidermal growth factor (EGF) receptor inhibitor according to the present invention is not particularly limited. The measurement of the mean particle size can employ, for example, a dynamic light scattering method and can be performed under measurement conditions involving a scattering angle of 173° and a wavelength of 633 nm. The method for measuring the median size (D50) of the vascular endothelial growth factor (VEGF) receptor inhibitor or the epidermal growth factor (EGF) receptor inhibitor according to the present invention is not particularly limited. The median size (D50) can be measured, for example, using a laser diffraction/scattering particle size distribution measurement apparatus under measurement conditions involving a 2 mV He—Ne laser (wavelength: 632.8 nm) focal length of 100 nm.

The content of the vascular endothelial growth factor (VEGF) receptor inhibitor or the epidermal growth factor (EGF) receptor inhibitor is not particularly limited and is, for example, preferably 0.01 to 20 parts by weight, more preferably 0.01 to 15 parts by weight, further preferably 0.01 to 10 parts by weight, per 100 parts by weight of the therapeutic agent for the ophthalmic disease.

The therapeutic agent for the ophthalmic disease of the present invention may further comprise one or more components selected from a thickening agent, a surfactant and a dispersion media, or one or more components selected from a preservative and an inclusion substance, in addition to the vascular endothelial growth factor (VEGF) receptor inhibitor or the epidermal growth factor (EGF) receptor inhibitor.

Preferably, the therapeutic agent for the ophthalmic disease of the present invention further comprises one or more components selected from a thickening agent, a surfactant and a dispersion media, and one or more components selected from a preservative and an inclusion substance, in addition to the vascular endothelial growth factor (VEGF) receptor inhibitor or the epidermal growth factor (EGF) receptor inhibitor.

Each of the thickening agent, the surfactant, the dispersion media, the preservative and the inclusion substance used may be one component or may be two or more components.

Examples of the thickening agent used in the therapeutic agent for the ophthalmic disease of the present invention include carboxyvinyl polymer, carboxymethylcellulose calcium, carboxymethylcellulose sodium, povidone (polyvinylpyrrolidone), partially hydrolyzed polyvinyl alcohol, hydroxypropylcellulose, hydroxypropylmethylcellulose, hydroxypropylmethylcellulose phthalate, hydroxyethylcellulose, amorphous cellulose, methylcellulose, magnesium aluminum silicate and triethanolamine.

The thickening agent is preferably polyvinyl alcohol, povidone (polyvinylpyrrolidone), hydroxypropylcellulose, hydroxypropylmethylcellulose, hydroxymethylcellulose, etc.

One of these thickening agents may be used alone, or two or more thereof may be used in combination.

The content of the thickening agent in the therapeutic agent for the ophthalmic disease of the present invention is not particularly limited and is, for example, preferably 0.01 to 5 parts by weight, more preferably 0.05 to 3 parts by weight, further preferably 0.1 to 2.5 parts by weight, per 100 parts by weight of the therapeutic agent for the ophthalmic disease.

Examples of the surfactant used in the therapeutic agent for the ophthalmic disease of the present invention include polyoxyethylene castor oil, polyoxyl 40 stearate, sucrose stearate, polyoxyethylene sorbitan monolaurate, polyoxyethylene sorbitan monostearate, polyoxyethylene sorbitan tristearate, polyoxyethylene sorbitan monooleate (polysorbate 80 and Tween(Registered Trademark) 80), polyoxyethylene sorbitan trioleate, sorbitan monolaurate, sodium lauryl sulfate, L-α-phosphatidylcholine (PC), 1,2-dipalmitoylphosphatidylcholine (DPPC), oleic acid, natural lecithin, synthetic lecithin, polyoxyethylene oleyl ether, polyoxyethylene lauryl ether, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol, tyloxapol, octylphenol ethoxylate, alkyl glucoside and poloxamer.

The surfactant is preferably polyoxyethylene sorbitan monooleate or poloxamer. Among them, polyoxyethylene sorbitan monooleate (polysorbate 80) or poloxamer (Pluronic(Registered Trademark) F-127) is more preferred.

One of these surfactants may be used alone, or two or more thereof may be used in combination.

The content of the surfactant in the therapeutic agent for the ophthalmic disease of the present invention is not particularly limited and is, for example, preferably 0 to 5 parts by weight, more preferably 0 to 3 parts by weight, further preferably 0 to 1.0 parts by weight, per 100 parts by weight of the therapeutic agent for the ophthalmic disease.

In the case of using a thickening agent and a surfactant in combination, examples of the combination of the thickening agent and the surfactant include, but are not particularly limited to, combinations such as hydroxypropylmethylcellulose and polyoxyethylene sorbitan monooleate, hydroxypropylcellulose and polyoxyethylene sorbitan monooleate, hydroxypropylcellulose and tyloxapol, povidone and polyoxyethylene sorbitan monooleate, polyvinyl alcohol and polyoxyethylene sorbitan monooleate, and poloxamer and polyoxyethylene sorbitan monooleate.

The combination of the thickening agent and the surfactant is preferably a combination of hydroxypropylcellulose and polyoxyethylene sorbitan monooleate, povidone and polyoxyethylene sorbitan monooleate, polyvinyl alcohol and polyoxyethylene sorbitan monooleate, or poloxamer and polyoxyethylene sorbitan monooleate, more preferably a combination of hydroxypropylcellulose and polyoxyethylene sorbitan monooleate, povidone and polyoxyethylene sorbitan monooleate, or poloxamer and polyoxyethylene sorbitan monooleate.

In the case of using a thickening agent and a surfactant in combination, the weight ratio between the thickening agent and the surfactant is not particularly limited. The surfactant/thickening agent weight ratio is, for example, 0 to 500, preferably 0 to 60, more preferably 0 to 10.

Examples of the dispersion media used in the therapeutic agent for the ophthalmic disease of the present invention include water, an alcohol, liquid paraffin, water containing a solute, an alcohol containing a solute, and liquid paraffin containing a solute.

The dispersion media is preferably water, liquid paraffin, or water containing a solute, more preferably water or water containing a solute.

One of these dispersion media may be used alone, or two or more thereof may be used in combination.

The content of the dispersion media in the therapeutic agent for the ophthalmic disease of the present invention is not particularly limited. The therapeutic agent for the ophthalmic disease can comprise the dispersion media so as to constitute a balance by adjusting the contents of components other than the dispersion media comprised in the therapeutic agent for the ophthalmic disease, in terms of a content per 100 parts by weight of the therapeutic agent for the ophthalmic disease. Specifically, the therapeutic agent for the ophthalmic disease can comprise the dispersion media such that the content of the dispersion media and the sum of the contents of components other than the dispersion media comprised in the therapeutic agent for the ophthalmic disease are added up to 100 parts by weight of the therapeutic agent for the ophthalmic disease. The content of the dispersion media is, for example, preferably 68 to 99.9 parts by weight, more preferably 78 to 99.9 parts by weight, further preferably 85 to 99.9 parts by weight, per 100 parts by weight of the therapeutic agent for the ophthalmic disease.

The solute comprised in the dispersion media is not particularly limited and is, for example, preferably a tonicity agent for use in the medical field.

Examples of the tonicity agent include sodium chloride, glucose (grape sugar), glycerol, mannitol, sodium dihydrogen phosphate, dibasic sodium phosphate hydrate, sodium bicarbonate, trishydroxymethylaminomethane, citric acid hydrate, boric acid, borax, and phosphoric acid.

The tonicity agent is preferably sodium chloride, glucose (grape sugar), glycerol, or mannitol.

One of these tonicity agents may be used alone, or two or more thereof may be used in combination.

The content of the solute in the therapeutic agent for the ophthalmic disease of the present invention is not particularly limited and is preferably 0 to 50 parts by weight, more preferably 0 to 25 parts by weight, per 100 parts by weight of the water, the alcohol, or the liquid paraffin.

Examples of the preservative used in the therapeutic agent for the ophthalmic disease of the present invention include benzalkonium chloride, methyl parahydroxybenzoate, propyl parahydroxybenzoate, chlorobutanol, disodium edetate hydrate, chlorhexidine gluconate, and sorbic acid.

The preservative is preferably benzalkonium chloride.

One of these preservatives may be used alone, or two or more thereof may be used in combination.

The content of the preservatives in the therapeutic agent for the ophthalmic disease of the present invention is not particularly limited and is, for example, preferably 0 to 1 parts by weight, more preferably 0 to 0.75 parts by weight, further preferably 0 to 0.5 parts by weight, per 100 parts by weight of the therapeutic agent for the ophthalmic disease. Alternatively, the content of the preservatives is not particularly limited and is, for example, preferably 0 to 100 parts by weight, more preferably 0 to 75 parts by weight, further preferably 0 to 50 parts by weight, per 100 parts by weight of the vascular endothelial growth factor (VEGF) receptor inhibitor or the epidermal growth factor (EGF) receptor inhibitor.

The inclusion substance used in the therapeutic agent for the ophthalmic disease of the present invention is not particularly limited as long as the inclusion substance has the property of incorporating a molecule. Examples thereof include α-cyclodextrin, β-cyclodextrin, 2-hydroxypropyl-β-cyclodextrin (HP-β-CD), and γ-cyclodextrin.

The inclusion substance is preferably β-cyclodextrin or 2-hydroxypropyl-β-cyclodextrin, more preferably 2-hydroxypropyl-β-cyclodextrin (HP-β-CD).

One of these inclusion substances may be used alone, or two or more thereof may be used in combination.

The content of the inclusion substance in the therapeutic agent for the ophthalmic disease of the present invention is not particularly limited and is, for example, preferably 0 to 1 parts by weight, more preferably 0 to 0.75 parts by weight, further preferably 0 to 0.5 parts by weight, per 100 parts by weight of the therapeutic agent for the ophthalmic disease.

The therapeutic agent for the ophthalmic disease of the present invention is administered by topical ocular administration. Examples of the topical ocular administration include ocular instillation, subconjunctival administration, sub-Tenon administration, intravitreal administration, suprachoroidal administration, periocular administration, and administration using an intraocular implant, and administration using other drug delivery devises. Ocular instillation is preferred.

The pharmaceutical composition of the present invention can be administered to a mammal or the like and thereby used in the prevention, treatment, etc. of a vascular endothelial growth factor (VEGF)-related disease or an epidermal growth factor (EGF)-related disease.

Examples of the vascular endothelial growth factor (VEGF)-related disease include wet-type (neovascular or exudative) age-related macular degeneration (wet-AMD), dry age-related, macular degeneration, choroidal neovascularization, myopic choroidal neovascularization, branch retinal vein occlusion, macular edema, macular edema following central retinal vein occlusion, diabetic macular edema, proliferative diabetic retinopathy, neovascular glaucoma, angioid streaks of the retina, retinopathy of prematurity, Coats disease, branch retinal vein occlusion, central retinal vein occlusion, cystoid macular edema, vitreous hemorrhage caused by diabetic retinopathy, Eales disease, central serous chorioretinopathy, epiretinal membrane, uveitis, multifocal choroiditis, anterior ischemic optic neuropathy, corneal neovascularization, pterygium, intraocular melanoma, vasoproliferative tumor of the retina, radiation retinopathy, tuberous sclerosis, vasoproliferative tumor of the retina, conjunctival squamous cell carcinoma and ocular hypertension.

The vascular endothelial growth factor (VEGF)-related disease is preferably wet age-related macular degeneration, myopic choroidal neovascularization, branch retinal vein occlusion, central retinal vein occlusion, macular edema following central retinal vein occlusion, diabetic macular edema, proliferative diabetic retinopathy or neovascular glaucoma.

Examples of the epidermal growth factor (EGF)-related disease include wet-type (neovascular or exudative) age-related macular degeneration (wet-AMD), dry age-related macular degeneration, choroidal neovascularization, myopic choroidal neovascularization, macular edema, macular edema following central retinal vein occlusion, diabetic macular edema, proliferative diabetic retinopathy, glaucoma, neovascular glaucoma, ocular inflammation, retinoblast, branch retinal vein occlusion, central retinal vein occlusion, retinopathy of prematurity, angioid streaks of the retina, retinal artery obstruction, corneal neovascularization, pterygium, uveal melanoma, uveitis, epiretinal membrane, corneal subepithelial fibrosis, dry eye, and meibomian gland dysfunction.

The epidermal growth factor (EGF)-related disease is preferably wet age-related macular degeneration, myopic choroidal neovascularization, branch retinal vein occlusion, central retinal vein occlusion, macular edema following central retinal vein occlusion, diabetic macular edema, proliferative diabetic retinopathy or neovascular glaucoma.

The pharmaceutical composition of the present invention can be used in the treatment, prevention, etc. of the vascular endothelial growth factor (VEGF)-related disease or the epidermal growth factor (EGF)-related disease and, among others, is preferably used in the prevention, treatment, etc. of ophthalmic diseases such as wet-type (neovascular or exudative) age-related macular degeneration (wet-AMD), macular edema following central retinal vein occlusion, myopic choroidal neovascularization and diabetic macular edema whose indications have been obtained for existing anti-VEGF inhibitors (intravitreal injections), and proliferative diabetic retinopathy, neovascular glaucoma, uveitis and retinopathy of prematurity on which the therapeutic effects of anti-VEGF inhibitors (intravitreal injections) have been clinically reported, albeit by off label indication.

In the epidermal growth factor (EGF)-related disease, a pathological condition is probably caused by angiogenesis or increase in vascular permeability in the eye. The pharmaceutical composition, of the present invention can be used in the treatment, prevention, etc. of the epidermal growth factor (EGF)-related disease and, among others, is preferably used in the prevention, treatment, etc. of ophthalmic diseases such as wet-type (neovascular or exudative) age-related macular degeneration (wet-AMD), macular edema following central retinal vein occlusion, myopic choroidal neovascularization and diabetic macular edema on which efficacy ascribable to an angiogenesis inhibitory effect or a suppressive effect on increase in vascular permeability in the eye has been confirmed.

As for the ophthalmic diseases as described above, for example, favorable therapeutic effects (recovery of best-corrected visual acuity, histological amelioration such as thinning of the retina thickened due to a pathological condition, etc.) have been clinically confirmed by the intravitreal injection of anti-VEGF inhibitors, and the inhibition of angiogenesis or the suppression of increase in vascular permeability in the retina or in the choroid has been nonclinically confirmed by the administration of EGF inhibitors. Hence, the clinical efficacy of these drugs is expected. However, for example, the existing anti-VEGF inhibitors (intravitreal injections) have high therapeutic effects, but put an enormous load on patients themselves, their families and health-care professionals, which is a social concern, because their administration route is intravitreal injection and continued treatment is necessary due to high rates of recurrence or the like. In light of these circumstances, there is a demand for the development of drugs (oral agents, eye drops, etc.), for the ophthalmic diseases as described above, administrable through a noninvasive and convenient route other than intravitreal injection, from the viewpoint of reduction in load on patients themselves, their families and health-care professionals, etc. In this respect, the therapeutic agent for the ophthalmic disease of the present invention is useful because the active ingredient can be administered to a patient through a route such as ocular instillation.

The dosage form of the therapeutic agent for the ophthalmic disease of the present invention is not particularly limited and is preferably a liquid formulation (a solution). The solution is more preferably a suspension formulation or a solution formulation.

A portion or the whole of the components of the therapeutic agent for the ophthalmic disease of the present invention, or a freeze-dried powder thereof may be dissolved or dispersed in water or the like to prepare the therapeutic agent for the ophthalmic disease of the present invention.

The method for producing the vascular endothelial growth factor (VEGF) receptor inhibitor or the epidermal growth factor (EGF) receptor inhibitor in a nanoparticle form in the therapeutic agent for the ophthalmic disease of the present invention is not particularly limited. The vascular endothelial growth factor (VEGF) receptor inhibitor or the epidermal growth factor (EGF) receptor inhibitor in a nanoparticle form can be produced by a nanoparticulation method, such as milling, which is generally used in the pharmaceutical technical field.

The nanoparticulation method can involve, for example, milling the vascular endothelial growth factor (VEGF) receptor inhibitor or the epidermal growth factor (EGF) receptor inhibitor using a commercially available instrument (zirconia container, zirconia balls, etc.), a commercially available nano pulverizer, or the like, followed by purification, etc. using a commercially available centrifuge or the like to produce the vascular endothelial growth factor (VEGF) receptor inhibitor or the epidermal growth factor (EGF) receptor inhibitor in a nanoparticle form. Alternatively, a solution of the vascular endothelial growth factor (VEGF) receptor inhibitor or the epidermal growth factor (EGF) receptor inhibitor can be crystallized by stimulation in a liquid phase or a vapor phase to produce the vascular endothelial growth factor (VEGF) receptor inhibitor or the epidermal growth factor (EGF) receptor inhibitor in a nanoparticle form.

In the milling step, the vascular endothelial growth factor (VEGF) receptor inhibitor or the epidermal growth factor (EGF) receptor inhibitor as well as one or more components selected from a thickening agent, a surfactant, a dispersion media, a preservatives and an inclusion substance may be added and milled.

In the milling step, one or more components selected from a thickening agent, surfactant and a dispersion media may be added, and one or more components selected from a preservatives and an inclusion substance may be further added, followed by the milling.

Examples of the milling method include, but are not particularly limited to, dry milling and wet milling. Wet milling is preferred.

The wet milling more preferably comprises adding a dispersion media to the vascular endothelial growth factor (VEGF) receptor inhibitor or the epidermal growth factor (EGF) receptor inhibitor, followed by the milling.

Examples of the purification method include, but are not particularly limited to, purification using a commercially available centrifuge or the like.

EXAMPLES

Hereinafter, the present invention will be described in more detail with reference to Reference Examples, Examples, and Test Examples. However, the present invention is not limited by these examples.

Reference Example 1

N-[2-Chloro-4-(6,7-dimethoxyquinolin-4-yloxy)phenyl]-N'-(5-methylisoxazol-3-yl)urea hydrochloride hydrate was prepared according to the method disclosed in Japanese Unexamined Patent Application Publication No. 2003-12668.

Example 1

N-[2-Chloro-4-(6,7-dimethoxyquinolin-4-yloxy)phenyl]-N'-(5-methylisoxazol-3-yl)urea hydrochloride hydrate was weighed into a zirconia container (Thinky Corp.) and subsequently prepared into a suspension by the addition of hydroxypropylcellulose (hydroxypropylcellulose (HPC), Wako Pure Chemical Industries, Ltd.; the same holds true for the description below), polysorbate 80 (Junsei Chemical Co., Ltd.; the same holds true for the description below), benzalkonium chloride (benzalkonium chloride (BAC), Nacalai Tesque, Inc.; the same holds true for the description below), D-mannitol (Junsei Chemical Co., Ltd.; the same holds true for the description below), and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp). Then, the milled product was diluted (mill/mix 400 rpm, 5 min) by the addition of an aqueous glucose solution (5% by mass; the same holds true for the description below), and the zirconia balls were removed through a screen (Clean Media 2000 rpm, 1 min, mill/mix 400 rpm, 1 min) to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

This nanoparticle composition was purified (13200 rpm, 28 min) using Micro Refrigerated Centrifuge (3740, Kubota Corp.) to adjust the concentration of N-[2-chloro-4-(6,7-dimethoxyquinolin-4-yloxy)phenyl]-N'-(5-methylisoxazol-3-yl)urea hydrochloride hydrate to 1.28 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 114 nm in the nanoparticle composition.

Example 2

A nanoparticle composition having N-[2-chloro-4-(6,7-dimethoxyquinolin-4-yloxy)phenyl]-N'-(5-methylisoxazol-3-yl)urea hydrochloride hydrate with a concentration of 5.36 mg/mL and a mean particle size of 169 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the purification conditions were changed to 13200 rpm and 5.5 minutes.

Example 3

A nanoparticle composition having N-[2-chloro-4-(6,7-dimethoxyquinolin-4-yloxy)phenyl]-N'-(5-methylisoxazol-3-yl)urea hydrochloride hydrate with a concentration of 6.50 mg/mL and a mean particle size of 151 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the purification conditions were changed to 13200 rpm and 2 minutes.

Example 4

A nanoparticle composition having N-[2-chloro-4-(6,7-dimethoxyquinolin-4-yloxy)phenyl]-N'-(5-methylisoxazol-3-yl)urea hydrochloride hydrate with a concentration of 0.54 mg/mL and a mean particle size of 122 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the purification conditions were changed to 13200 rpm and 20 minutes.

TABLE 1

| Example | Compositional ratio (parts by weight) N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol | Concentration (mg/ml) | Mean particle size (nm) |
|---|---|---|---|
| 1 | 1/0.5/0.1/0.001/0.1 | 1.28 | 114 |
| 2 | 1/0.5/0.1/0.001/0.1 | 5.36 | 169 |
| 3 | 1/0.5/0.1/0.001/0.1 | 6.50 | 151 |
| 4 | 1/0.5/0.1/0.001/0.1 | 0.54 | 122 |

Example 5

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.75 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.49 mg/mL and a mean particle size of 198 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the amount of hydroxypropylcellulose (HPC) was changed from 0.5 parts by weight to 0.75 parts by weight.

Example 6

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (DAC)/D-mannitol=1 part by weight/1.00 part by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.29 mg/mL and a mean particle size of 175 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the amount of hydroxypropylcellulose (HPC) was changed from 0.5 parts by weight to 1.0 part by weight.

Example 7

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/1.25 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.42 mg/mL and a mean particle size of 188 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the amount of hydroxypropylcellulose (HPC) was changed from 0.5 parts by weight to 1.25 parts by weight.

Example 8

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/2.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.44 mg/mL and a mean particle size of 471 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the amount of hydroxypropylcellulose (HPC) was changed from 0.5 parts by weight to 2.5 parts by weight.

TABLE 2

| Example | Compositional ratio (parts by weight) N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol | Concentration (mg/mL) | Mean particle size (nm) |
|---|---|---|---|
| 5 | 1/0.75/0.1/0.001/0.1 | 1.49 | 198 |
| 6 | 1/1.0/0.1/0.001/0.1 | 1.29 | 175 |
| 7 | 1/1.25/0.1/0.001/0.1 | 1.42 | 188 |
| 8 | 1/2.5/0.1/0.001/0.1 | 1.44 | 471 |

Example 9

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/1.0 part by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.36 mg/mL and a mean particle size of 179 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the amount of polysorbate 80 was changed from 0.1 parts by weight to 1.0 part by weight.

Example 10

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.001 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.51 mg/mL and a mean particle size of 117 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the amount of polysorbate 80 was changed from 0.1 parts by weight to 0.001 part by weight.

Example 11

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/benzalkonium chloride (BAC)/D-mannitol=1 part by weight/0.5 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.17 mg/mL and a mean particle size of 105 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), benzalkonium chloride (BAC), D-mannitol, and an aqueous glucose solution in accordance with Example 1 except that polysorbate 80 was excluded from the composition.

TABLE 3

| Example | Compositional ratio (parts by weight) N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol | Concentration (mg/mL) | Mean particle size (nm) |
|---|---|---|---|
| 9 | 1/0.5/1.0/0.001/0.1 | 1.36 | 179 |
| 10 | 1/0.5/0.001/0.001/0.1 | 1.51 | 117 |
| 11 | 1/0.5/0/0.001/0.1 | 1.17 | 105 |

Example 12

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/1.0 part by weight and having N-[2-chloro-4-(6,7-dimethoxyquinolin-4-yloxy)phenyl]-N'-(5-methylisoxazol-3-yl)urea hydrochloride hydrate with a concentration of 1.13 mg/mL and a mean particle size of 140 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the amount of D-mannitol was changed from 0.1 parts by weight to 1.0 part by weight.

Example 13

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.5 parts by weight and having N-[2-chloro-4-(6,7-dimethoxyquinolin-4-yloxy)phenyl]-N'-(5-methylisoxazol-3-yl)urea hydrochloride hydrate with a concentration of 1.53 mg/mL and a mean particle size of 124 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the amount of D-mannitol was changed from 0.1 parts by weight to 0.5 parts by weight.

Example 14

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)=1 part by weight/0.5 parts by weight/0.1 parts by weight/0.001 parts by weight and having N-[2-chloro-4-(6,7-dimethoxyquinolin-4-yloxy)phenyl]-N'-(5-methylisoxazol-3-yl)urea hydrochloride hydrate with a concentration of 0.50 mg/mL and a mean particle size of 138 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), and an aqueous glucose solution in accordance with Example 1 except that D-mannitol was excluded from the composition.

TABLE 4

| Example | Compositional ratio (parts by weight) N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol | Concentration (mg/mL) | Mean particle size (nm) |
|---|---|---|---|
| 12 | 1/0.5/0.1/0.001/1.0 | 1.13 | 140 |
| 13 | 1/0.5/0.1/0.001/0.5 | 1.53 | 124 |
| 14 | 1/0.5/0.1/0.001/0 | 0.50 | 138 |

Example 15

N-[2-Chloro-4-(6,7-dimethoxyquinolin-4-yloxy)phenyl]-N'-(5-methylisoxazol-3-yl)urea hydrochloride hydrate was weighed into a zirconia container and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.05 mm, Nikkato Corp.) were placed in the container, which was then covered with the lid. Wet milling was performed using Rotation/Revolution Nano Pulverizer (NP-100, Thinky Corp.). Then, the milled product was diluted by the addition of an aqueous glucose solution, and the zirconia bells were removed through a screen to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

This nanoparticle composition was purified (10000 rpm, 1 min) using Micro Refrigerated Centrifuge (3740, Kubota Corp.) to adjust the concentration of N-[2-chloro-4-(6,7-dimethoxyquinolin-4-yloxy)phenyl]-N'-(5-methylisoxazol-3-yl)urea hydrochloride hydrate to 0.65 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 426 nm in the nanoparticle composition.

Example 16

N-[2-Chloro-4-(6,7-dimethoxyquinolin-4-yloxy)phenyl]-N'-(5-methylisoxazol-3-yl)urea hydrochloride hydrate was weighed into a zirconia container and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 1.0 mm, Nikkato Corp.) were placed in the container, which was then covered with the lid. Wet milling was performed using Rotation/Revolution Nano Pulverizer (NP-100, Thinky Corp.). Then, the milled product was diluted by the addition of an aqueous glucose solution, and the zirconia balls were removed through a screen to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

This nanoparticle composition was purified using Micro Refrigerated Centrifuge (3740, Kubota Corp.) to adjust the concentration of N-[2-chloro-4-(6,7-dimethoxyquinolin-4-yloxy)phenyl]-N'-(5-methylisoxazol-3-yl)urea hydrochloride hydrate to 1.35 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 154 nm in the nanoparticle composition.

Example 17

N-[2-Chloro-4-(6,7-dimethoxyquinolin-4-yloxy)phenyl]-N'-(5-methylisoxazol-3-yl)urea hydrochloride hydrate was weighed into a zirconia container and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 3.0 mm, Nikkato Corp) were placed in the container, which was then covered with the lid. Wet milling was performed using Rotation/Revolution Nano Pulverizer (NP-100, Thinky Corp.). Then, the milled product was diluted by the addition of an aqueous glucose solution, and the zirconia balls were removed through a screen to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

This nanoparticle composition was purified using Micro Refrigerated Centrifuge (3740, Kubota Corp.) to adjust the concentration of N-[2-chloro-4-(6,7-dimethoxyquinolin-4-yloxy)phenyl]-N'-(5-methylisoxazol-3-yl)urea hydrochloride hydrate to 1.17 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 155 nm in the nanoparticle composition.

TABLE 5

| Example | Zirconia ball diameter (mm) | Concentration (mg/mL) | Mean particle size (nm) |
| --- | --- | --- | --- |
| 15 | 0.05 | 0.65 | 426 |
| 16 | 1.0 | 1.35 | 154 |
| 17 | 3.0 | 1.17 | 155 |

Example 18

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 4.09 mg/mL and a mean particle size of 164 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glycerol solution in accordance with Example 1 except that the aqueous glucose solution was changed to an aqueous glycerol solution (8.2% by mass; the same holds true for the description below).

Example 19

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 0.49 mg/mL and a mean particle size of 133 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glycerol solution in accordance with Example 1 except that the aqueous glucose solution was changed to an aqueous glycerol solution.

Example 20

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)=1 part by weight/0.5 parts by weight/0.1 parts by weight/0.001 parts by weight and having N-[2-chloro-4-(6,7-dimethoxyquinolin-4-yloxy)phenyl]-N'-(5-methylisoxazol-3-yl)urea hydrochloride hydrate with a concentration of 0.76 mg/mL and a mean particle size of 148 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), and an aqueous glycerol solution in accordance with Example 1 except that the aqueous glucose solution was changed to an aqueous glycerol solution, and D-mannitol was excluded from the composition.

Example 21

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)=1 part by weight/0.5 parts by weight/0.1 parts by weight/0.001 parts by weight and having N-[2-chloro-4-(6,7-dimethoxyquinolin-4-yloxy)phenyl]-N'-(5-methylisoxazol-3-yl)urea hydrochloride hydrate with a concentration of 0.18 mg/mL and a mean particle size of 119 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), and an aqueous glycerol solution in accordance with Example 1 except that the aqueous glucose solution was changed to an aqueous glycerol solution, and D-mannitol was excluded from the composition.

Example 22

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 3.21 mg/mL and a mean particle size of 266 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and saline in accordance with Example 1 except that the aqueous glucose solution was changed to saline.

Example 23

A nanoparticle composition having composition of N-[2-chloro-4-(6,7-dimethoxyquinolin-4-yloxy)phenyl]-N'-(5- methylisoxazol-3-yl)urea hydrochloride hydrate/hydroxypropylcellulose (HPC)/polysorbate 80/benzalkonium chloride (BAC)/D-mannitol=1 part by weight/0.3 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 0.24 mg/mL and a mean particle size of 252 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and saline in accordance with Example 1 except that the aqueous glucose solution was changed to saline.

TABLE 6

| Example | Compositional ratio (parts by weight) N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol | Dispersion media | Concentration (mg/mL) | Mean particle size (nm) |
|---|---|---|---|---|
| 18 | 1/0.5/0.1/0.001/0.1 | Aqueous glycerol solution | 4.09 | 164 |
| 19 | 1/0.5/0.1/0.001/0.1 | Aqueous glycerol solution | 0.49 | 133 |
| 20 | 1/0.5/0.1/0.001/0 | Aqueous glycerol solution | 0.76 | 148 |
| 21 | 1/0.5/0.1/0.001/0 | Aqueous glycerol solution | 0.18 | 119 |
| 22 | 1/0.5/0.1/0.001/0.1 | Saline | 3.21 | 266 |
| 23 | 1/0.5/0.1/0.001/0.1 | Saline | 0.24 | 252 |

Example 24

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylmethylcellulose (HPMC)/polysorbate 80/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 0.54 mg/mL and a mean particle size of 153 nm was obtained from N-[2-chloro-4-(6,7-dimethoxyquinolin-4-yloxy)phenyl]-N'-(5-methylisoxazol-3-yl)urea hydrochloride hydrate, hydroxypropylmethylcellulose (hydroxypropylmethylcellulose (HPMC), Shin-Etsu Chemical Co., Ltd.; the same holds true for the description below), polysorbate 80, benzalkonium chloride (BAC), D-mannitol, and an aqueous glucose solution in accordance with Example 1 except that the thickening agent was changed from hydroxypropylcellulose (HPC) to hydroxypropylmethylcellulose (HPMC).

Example 25

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol/hydroxypropyl-β-cyclodextrin (HP-β-CD)=1 part by weight/0.5 parts by weight/0.1 parts by weight/0.001 parts by weight/0.1 parts by weight/0.5 parts by weight and having N-[2-chloro-4-(6,7-dimethoxyquinolin-4-yloxy)phenyl]-N'-(5-methylisoxazol-3-yl)urea hydrochloride hydrate with a concentration of 0.27 mg/mL and a mean particle size of 32 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, hydroxypropyl-β-cyclodextrin (hydroxypropyl-β-cyclodextrin (HP-β-CD), Sigma-Aldrich Co. LLC; the same holds true for the description below), and an aqueous glucose solution in accordance with Example 1 except that an inclusion substance (hydroxypropyl-β-cyclodextrin (HP-β-CD)) was added to the composition.

Example 26

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinyl alcohol (PVA)/polysorbate 80/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.53 mg/mL and a mean particle size of 139 nm was obtained from N-[2-chloro-4-(6,7-dimethoxyquinolin-4-yloxy)phenyl]-N'-(5-methylisoxazol-3-yl)urea hydrochloride hydrate, polyvinyl alcohol (polyvinyl alcohol (PVA), Sigma-Aldrich Co. LLC; the same holds true for the description below), polysorbate 80, benzalkonium chloride (BAC), D-mannitol, and an aqueous glucose solution in accordance with Example 1 except that the thickening agent was changed from hydroxypropylcellulose (HPC) to polyvinyl alcohol (PVA).

Example 27

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)/polysorbate 80/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.44 mg/mL and a mean particle size of 89 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (polyvinylpyrrolidone (PVP), Junsei Chemical Co., Ltd.; the same holds true for the description below), polysorbate 80, benzalkonium chloride (BAC), D-mannitol, and an aqueous glucose solution in accordance with Example 1 except that the thickening agent was changed from hydroxypropylcellulose (HPC) to polyvinylpyrrolidone (PVP).

Example 28

N-[2-Chloro-4-(6,7-dimethoxyquinolin-4-yloxy)phenyl]-N'-(5-methylisoxazol-3-yl)urea hydrochloride hydrate was weighed into a zirconia container and subsequently prepared into a suspension by the addition of polyoxyethylene (196) polyoxypropylene (67) glycol (Pluronic(Registered Trademark) F-127, Sigma-Aldrich Co. LLC; the same holds true for the description below) and water. Zirconia balls (zirconia milling balls, YTZ, diameter: 0.1 mm, Nikkato Corp.) were placed in the container, which was then covered with the lid. Wet milling was performed using Rotation/Revolution Nano Pulverizer (NP-100, Thinky Corp.). Then, the milled product was diluted by the addition of water, and the zirconia balls were removed through a screen to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/Pluronic(Registered Trademark) F-127=1 part by weight/0.15 parts by weight.

This nanoparticle composition was purified (13200 rpm, 60 min) using Micro Refrigerated Centrifuge (3740, Kubota Corp.) to adjust the concentration of N-[2-chloro-4-(6,7-dimethoxyquinolin-4-yloxy)phenyl]-N'-(5-methylisoxazol-3-yl)urea hydrochloride hydrate to 8.13 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 147 nm in the nanoparticle composition.

Example 29

A nanoparticle composition having composition of N-[2-chloro-4-(6,7-dimethoxyquinolin-4-yloxy)phenyl]-N'-(5-methylisoxazol-3-yl)urea hydrochloride hydrate/Pluronic(Registered Trademark) F-127=1 part by weight/0.5 parts by weight and having N-[2-chloro-4-(6,7-dimethoxyquinolin-4-yloxy)phenyl]-N'-(5-methylisoxazol-3-yl)urea hydrochloride hydrate with a concentration of 1.00 mg/mL and a mean particle size of 86 nm was obtained from N-[2-chloro-4-(6,7-dimethoxyquinolin-4-yloxy)phenyl]-N'-(5-methylisoxazol-3-yl)urea hydrochloride hydrate, Pluronic(Registered Trademark) F-127, and water in accordance with Example 28 except that the amount of Pluronic(Registered Trademark) F-127 was changed from 0.15 parts by weight to 0.5 parts by weight.

Example 30

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/Solutol(Registered Trademark) HS15/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.52 mg/mL and a mean particle size of 132 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), Solutol(Registered Trademark) HS15, benzalkonium chloride (BAC), D-mannitol, and an aqueous glucose solution in accordance with Example 1 except that the surfactant was changed from polysorbate 80 to 12-hydroxy-octadecanoic acid polymer with α-hydro-ω-hydroxypoly(oxy-1,2-ethanediyl) (Solutol (Registered Trademark) HS15, BASF SE; the same holds true for the description below).

Example 31

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/tyloxapol/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.51 mg/mL and a mean particle size of 114 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), tyloxapol, benzalkonium chloride (BAC), D-mannitol, and an aqueous glucose solution in accordance with Example 1 except that the surfactant was changed from polysorbate 80 to 4-(1,1,3,3-tetramethylbutyl)phenol polymer (containing formaldehyde and oxirane) (tyloxapol, Sigma-Aldrich Co. LLC; the same holds true for the description below).

Example 32

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/Triton (Registered Trademark) X100/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.04 mg/mL and a mean particle size of 132 nm was obtained from N-[2-chloro-4-(6,7-dimethoxyquinolin-4-

TABLE 7

| Example | Compositional ratio (parts by weight) N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol | X | Dispersion media | Concentration (mg/mL) | Mean particle size (nm) |
|---|---|---|---|---|---|
| 24 | 1/0.5/0/0.1/0.001/0.1 | HPMC | Aqueous glucose solution | 0.54 | 153 |
| 26 | 1/0.5/0/0.1/0.001/0.1 | PVA | Aqueous glucose solution | 1.53 | 139 |
| 27 | 1/0.5/0/0.1/0.001/0.1 | PVP | Aqueous glucose solution | 1.44 | 89 |
| 28 | 1/0.15/0/0/0/0 | Pluronic F127 | Water | 8.13 | 147 |
| 29 | 1/0.5/0/0/0/0 | Pluronic F127 | Water | 1.00 | 86 | yloxy)phenyl]-N'-(5-methylisoxazol-3-yl)urea hydrochloride hydrate, hydroxypropylcellulose (HPC), Triton (Registered Trademark) X100 (Nacalai Tesque, Inc.; the same holds true for the description below), benzalkonium chloride (BAC), D-mannitol, and an aqueous glucose solution in accordance with Example 1 except that the surfactant was changed from polysorbate 80 to polyethylene glycol mono-p-isooctyl phenyl ether (Triton (Registered Trademark) X100, Nacalai Tesque, Inc.; the same holds true for the description below).

Example 33

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/Cremophor(Registered Trademark) EL/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.12 mg/mL and a mean particle size of 125 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), Cremophor (Registered Trademark) EL, benzalkonium chloride (BAC), D-mannitol, and an aqueous glucose solution in accordance with Example 1 except that the surfactant was changed from polysorbate 80 to polyoxyethylene castor oil (Cremophor (Registered Trademark) EL, Sigma-Aldrich Co. LLC; the same holds true for the description below).

Example 34

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/n-octyl-β-D-glucoside/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.23 mg/mL and a mean particle size of 120 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), n-octyl-β-D-glucoside (Wako Pure Chemical Industries, Ltd.; the same holds true for the description below), benzalkonium chloride (BAC), D-mannitol, and an aqueous glucose solution in accordance with Example 1 except that the surfactant was changed from polysorbate 80 to n-octyl-β-D-glucoside.

Example 35

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/sodium lauryl sulfate/benzalkonium chloride (BAC)/D-mannitol=1 part by weight/0.25 parts by weight/0.0005 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 3.57 mg/mL and a mean particle size of 70 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), sodium lauryl sulfate (Nacalai Tesque, Inc.; the same holds true for the description below), benzalkonium chloride (BAC), D-mannitol, and an aqueous glucose solution in accordance with Example 1 except that the surfactant was changed from polysorbate 80 to sodium lauryl sulfate, and the amount of hydroxypropylcellulose (HPC) was changed from 0.5 parts by weight to 0.25 parts by weight.

Example 36

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/sodium lauryl sulfate=1 part by weight/0.1 parts by weight/0.0025 parts by weight and having N-[2-chloro-4-(6,7-dimethoxyquinolin-4-yloxy)phenyl]-N'-(5-methylisoxazol-3-yl)urea hydrochloride hydrate with a concentration of 2.74 mg/mL and a mean particle size of 66 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), sodium lauryl sulfate, and an aqueous glucose solution in accordance with Example 1 except that: the amount of hydroxypropylcellulose (HPC) was changed from 0.5 parts by weight to 0.1 parts by weight; the surfactant was changed from polysorbate 80 to sodium lauryl sulfate; and benzalkonium chloride (BAC) and D-mannitol were excluded from the composition.

Example 37

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/sodium lauryl sulfate/D-mannitol=1 part by weight/0.1 parts by weight/0.0025 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 2.47 mg/mL and a mean particle size of 97 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), sodium lauryl sulfate, D-mannitol, and an aqueous glucose solution in accordance with Example 1 except that: the amount of hydroxypropylcellulose (HPC) was changed from 0.5 parts by weight to 0.1 parts by weight; the surfactant was changed from polysorbate 80 to sodium lauryl sulfate; and benzalkonium chloride (BAC) was excluded from the composition.

TABLE 8

| Example | Compositional ratio (parts by weight) N-[2-Chloro-4-(6,7-dimethoxyquinolin-4-yloxy)phenyl]-N'-(5-methylisoxazol-3-yl)urea hydrochloride hydrate/hydroxypropylcellulose (HPC)/X/benzalkonium chloride (BAC)/D-mannitol | X | Concentration (mg/mL) | Mean particle size (nm) |
|---|---|---|---|---|
| 30 | 1/0.5/0.1/0.001/0.1 | Solutol HS15 | 1.52 | 132 |
| 31 | 1/0.5/0.1/0.001/0.1 | Tyloxapol | 1.51 | 114 |
| 32 | 1/0.5/0.1/0.001/0.1 | Triton X100 | 1.04 | 132 |
| 33 | 1/0.5/0.1/0.001/0.1 | Cremophor EL | 1.12 | 125 |
| 34 | 1/0.5/0.1/0.001/0.1 | n-Octyl-β-D-glucoside | 1.23 | 120 |
| 35 | 1/0.25/0.0005/0.001/0.1 | Sodium laurel sulfate | 3.57 | 70 |
| 36 | 1/0.1/0.0025/0/0 | Sodium lauryl sulfate | 2.74 | 66 |
| 37 | 1/0.1/0.0025/0/0.1 | Sodium lauryl sulfate | 2.47 | 97 |

Example 38

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/D-mannitol=1 part by weight/0.5 parts by weight/0.1 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.23 mg/mL and a mean particle size of 121 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, D-mannitol, and an aqueous glucose solution in accordance with Example 1 except that benzalkonium chloride (BAC) was excluded from the composition.

Example 39

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.01 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.57 mg/mL and a mean particle size of 111 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that the amount of benzalkonium chloride (BAC) was changed from 0.001 parts by weight to 0.01 part by weight.

Example 40

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)=1 part by weight/0.3 parts by weight and having N-[2-chloro-4-(6,7-dimethoxyquinolin-4-yloxy)phenyl]-N'-(5-methylisoxazol-3-yl)urea hydrochloride hydrate with a concentration of 1.25 mg/mL and a mean particle size of 81 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), and an aqueous glucose solution in accordance with Example 1 except that the amount of hydroxypropylcellulose (HPC) was changed from 0.5 parts by weight to 0.3 parts by weight, and polysorbate 80, benzalkonium chloride (BAC), and D-mannitol were excluded from the composition.

Example 41

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80=1 part by weight/0.3 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 2.04 mg/mL and a mean particle size of 89 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, and an aqueous glucose solution in accordance with Example 1 except that the amount of hydroxypropylcellulose (HPC) was changed from 0.5 parts by weight to 0.3 parts by weight, and benzalkonium chloride (BAC) and D-mannitol were excluded from the composition.

Example 42

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80=1 part by weight/0.3 parts by weight/0.01 parts by weight and having N-[2-chloro-4-(6,7-dimethoxyquinolin-4-yloxy)phenyl]-N'-(5-methylisoxazol-3-yl)urea hydrochloride hydrate with a concentration of 1.74 mg/mL and a mean particle size of 73 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, and an aqueous glucose solution in accordance with Example 1 except that: the amount of hydroxypropylcellulose (HPC) was changed from 0.5 parts by weight to 0.3 parts by weight; the amount of polysorbate 80 was changed from 0.1 parts by weight to 0.01 parts by weight; and benzalkonium chloride (BAC) and D-mannitol were excluded from the composition.

Example 43

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80=1 part by weight/ 0.15 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 4.89 mg/mL and a mean particle size of 111 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, and an aqueous glucose solution in accordance with Example 1 except that: the amount of hydroxypropylcellulose (HPC) was changed from 0.5 parts by weight to 0.15 parts by weight; and benzalkonium chloride (BAC) and D-mannitol were excluded from, the composition.

Example 44

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80=1 part by weight/ 0.15 parts by weight/0.01 parts by weight and having N-[2-chloro-4-(6,7-dimethoxyquinolin-4-yloxy)phenyl]-N'-(5-methylisoxazol-3-yl)urea hydrochloride hydrate with a concentration of 3.52 mg/mL and a mean particle size of 67 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, and an aqueous glucose solution in accordance with Example 1 except that: the amount of hydroxypropylcellulose (HPC) was changed from 0.5 parts by weight to 0.15 parts by weight; the amount of polysorbate 80 was changed from 0.1 parts by weight to 0.01 parts by weight; and benzalkonium chloride (BAC) and D-mannitol were excluded from the composition.

Example 45

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)=1 part by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 2.51 mg/mL and a mean particle size of 69 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), and an aqueous glucose solution in accordance with Example 1 except that: the amount of hydroxypropylcellulose (HPC) was changed from 0.5 parts by weight to 0.1 parts by weight; and polysorbate 80, benzalkonium chloride (BAC), and D-mannitol were excluded from the composition.

Example 46

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/D-mannitol=1 part by weight/0.1 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 2.23 mg/mL and a mean particle size of 60 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), D-mannitol, and an aqueous glucose solution in accordance with Example 1 except that: the amount of hydroxypropylcellulose (HPC) was changed from 0.5 parts by weight to 0.1 parts by weight; and polysorbate 80 and benzalkonium chloride (BAC) were excluded from the composition.

Example 47

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.1 parts by weight/0.02 parts by weight/0.0002 parts by weight/0.02 parts by weight and having N-[2-chloro-4-(6,7-dimethoxyquinolin-4-yloxy)phenyl]-N'-(5-methylisoxazol-3-yl)urea hydrochloride hydrate with a concentration of 2.51 mg/mL and a mean particle size of 67 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that: the amount of hydroxypropylcellulose (HPC) was changed from 0.5 parts by weight to 0.1 parts by weight; the amount of polysorbate 80 was changed from 0.1 parts by weight to 0.02 parts by weight; the amount of benzalkonium chloride (BAC) was changed from 0.001 parts by weight to 0.0002 parts by weight; and the amount of D-mannitol was changed from 0.1 parts by weight to 0.02 parts by weight.

Example 48

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.1 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.75 mg/mL and a mean particle size of 82 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 1 except that: the amount of hydroxypropylcellulose (HPC) was changed from 0.5 parts by weight to 0.1 parts by weight.

Example 49

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)=1 part by weight/0.05 parts by weight and having N-[2-chloro-4-(6,7-dimethoxyquinolin-4-yloxy)phenyl]-N'-(5-methylisoxazol-3-yl)urea hydrochloride hydrate with a concentration of 2.00 mg/mL and a mean particle size of 66 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), and an aqueous glucose solution in accordance with Example 1 except that: the amount of hydroxypropylcellulose (HPC) was changed from 0.5 parts by weight to 0.05 parts by weight; and polysorbate 80, benzalkonium chloride (BAC), and D-mannitol were excluded from the composition.

Example 50

N-[2-Chloro-4-(6,7-dimethoxyquinolin-4-yloxy)phenyl]-N'-(5-methylisoxazol-3-yl)urea hydrochloride hydrate was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

This nanoparticle composition was purified (13200 rpm, 25 min) using Micro Refrigerated Centrifuge (3740, Kubota Corp.) and then pH-adjusted to 3 to adjust the concentration of N-[2-chloro-4-(6,7-dimethoxyquinolin-4-yloxy)phenyl]-N'-(5-methylisoxazol-3-yl)urea hydrochloride hydrate to 1.31 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 133 nm in the nanoparticle composition.

Example 51

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)=1 part by weight/0.5 parts by weight/0.1 parts by weight/0.001 parts by weight and having N-[2-chloro-4-(6,7-dimethoxyquinolin-4-yloxy)phenyl]-N'-(5-methylisoxazol-3-yl)urea hydrochloride hydrate with a concentration of 1.49 mg/mL and a mean particle size of 98 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), and an aqueous D-mannitol solution in accordance with Example 1 except that the aqueous glucose solution was changed to an aqueous D-mannitol solution (10% by mass; the same holds true for the description below).

Example 52

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.35 mg/mL and a mean particle size of 137 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous citric acid hydrate solution in accordance with Example 1 except that the aqueous glucose solution was changed to an aqueous citric acid solution (1% by mass).

Example 53

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 0.75 mg/mL and a mean particle size of 227 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous phosphoric acid solution in accordance with Example 1 except that the aqueous glucose solution was changed to an aqueous phosphoric acid solution (6.2% by mass; the same holds true for the description below).

Example 54

N-[2-Chloro-4-(6,7-dimethoxyquinolin-4-yloxy)phenyl]-N'-(5-methylisoxazol-3-yl)urea hydrochloride hydrate was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glycerol solution, and the zirconia balls were removed through a screen (Clean Media 2000 rpm, 1 min, mill/mix 400 rpm, 1 min) to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

This nanoparticle composition was diluted with an aqueous glucose solution. As a result of measuring the concentration, N-[2-chloro-4-(6,7-dimethoxyquinolin-4-yloxy)phenyl]-N'-(5-methylisoxazol-3-yl)urea hydrochloride hydrate had a concentration of 1.30 mg/mL.

As a result of assaying the nanoparticle composition using Zeta Sizer (Malvern instruments Nano series), N-[2-chloro- 4-(6,7-dimethoxyquinolin-4-yloxy)phenyl]-N'-(5-methylisoxazol-3-yl)urea hydrochloride hydrate had a mean particle size of 203 nm in the nanoparticle composition.

ride (BAC), D-mannitol, and an aqueous glucose solution in accordance with Example 1 except that lecithin was used as an additional surfactant.

TABLE 9

| Example | Compositional ratio (parts by weight) (N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol | Dispersion media | Concentration (mg/mL) | Mean particle size (nm) |
|---|---|---|---|---|
| 38 | 1/0.5/0.1/0/0.1 | Aqueous glucose solution | 1.23 | 121 |
| 39 | 1/0.5/0.1/0.01/0.1 | Aqueous glucose solution | 1.57 | 111 |
| 40 | 1/0.3/0/0/0 | Aqueous glucose solution | 1.25 | 81 |
| 41 | 1/0.3/0.1/0/0 | Aqueous glucose solution | 2.04 | 89 |
| 42 | 1/0.3/0.01/0/0 | Aqueous glucose solution | 1.74 | 73 |
| 43 | 1/0.15/0.1/0/0 | Aqueous glucose solution | 4.89 | 111 |
| 44 | 1/0.15/0.01/0/0 | Aqueous glucose solution | 3.52 | 67 |
| 45 | 1/0.1/0/0/0 | Aqueous glucose solution | 2.51 | 69 |
| 46 | 1/0.1/0/0/0.1 | Aqueous glucose solution | 2.23 | 60 |
| 47 | 1/0.1/0.02/0.0002/0.02 | Aqueous glucose solution | 2.51 | 67 |
| 48 | 1/0.1/0.1/0.001/0.1 | Aqueous glucose solution | 1.75 | 82 |
| 49 | 1/0.05/0/0/0 | Aqueous glucose solution | 2.00 | 66 |
| 50 | 1/0.5/0.1/0.001/0.1 | Aqueous glucose solution | 1.31 | 133 |
| 51 | 1/0.5/0.1/0.001 | Aqueous D-mannitol solution | 1.49 | 98 |
| 52 | 1/0.5/0.1/0.001/0.1 | Aqueous citric acid solution | 1.35 | 137 |
| 53 | 1/0.5/0.1/0.001/0.1 | Aqueous phosphoric acid solution | 0.75 | 227 |
| 54 | 1/0.5/0.1/0.001/0.1 | Aqueous glycerol solution | 1.30 | 203 |

Example 55

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polyvinylpyrrolidone (PVP)/polysorbate 80/benzalkonium chloride (BAC)/D-mannitol=1 part by weight/0.5 parts by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.23 mg/mL and a mean particle size of 149 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polyvinylpyrrolidone (PVP), polysorbate 80, benzalkonium chloride (BAC), D-mannitol, and an aqueous glucose solution in accordance with Example 1 except that polyvinylpyrrolidone (PVP) was used as an additional thickening agent.

Example 56

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/lecithin/polysorbate 80/benzalkonium chloride (BAC)/D-mannitol=1 part by weight/0.5 parts by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.35 mg/mL and a mean particle size of 144 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), lecithin (Nacalai Tesque, Inc.), polysorbate 80, benzalkonium chlo Example 57

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polyethylene glycol/polysorbate 80/benzalkonium chloride (BAC)/D-mannitol=1 part by weight/0.5 parts by weight/0.01 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.62 mg/mL and a mean particle size of 128 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polyethylene glycol (Sigma-Aldrich Co. LLC; the same holds true for the description below), polysorbate 80, benzalkonium chloride (BAC), D-mannitol, and an aqueous glucose solution in accordance with Example 1 except that polyethylene glycol was used as an additional surfactant.

Example 58

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)/polyethylene glycol/benzalkonium chloride (BAC)/D-mannitol=1 part by weight/0.5 parts by weight/0.01 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 2.86 mg/mL and a mean particle size of 65 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), polyethylene glycol, benzalkonium chloride (BAC), D-mannitol, and an aqueous glucose solution in accordance with Example 1 except that polyethylene glycol was used as an additional surfactant.

Example 59

A nanoparticle composition having composition of N-[2-chloro-4-(6,7-dimethoxyquinolin-4-yloxy)phenyl]-N'-(5- methylisoxazol-3-yl)urea hydrochloride hydrate/polyvinylpyrrolidone (PVP)/sodium lauryl sulfate=1 part by weight/0.1 parts by weight/0.0025 parts by weight and having N-[2-chloro-4-(6,7-dimethoxyquinolin-4-yloxy)phenyl]-N'-(5-methylisoxazol-3-yl)urea hydrochloride hydrate with a concentration of 2.44 mg/mL and a mean particle size of 89 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), sodium lauryl sulfate, and an aqueous glucose solution in accordance with Example 1 except that: the thickening agent was changed from hydroxypropylcellulose (HPC) to polyvinylpyrrolidone (PVP); the surfactant was changed from polysorbate 80 to sodium lauryl sulfate; and benzalkonium chloride (BAC) and D-mannitol were excluded from the composition.

changed from hydroxypropylcellulose (HPC) to Pluronic (Registered Trademark) F-127; the amount of polysorbate 80 was changed from 0.1 parts by weight to 0.02 parts by weight; and benzalkonium chloride (BAC) and D-mannitol were excluded from the composition.

Example 62

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)/polysorbate 80/benzalkonium chloride (BAC)/D-mannitol=1 part by weight/0.25 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydro-

TABLE 10

| Example | Compositional ratio (parts by weight) N-[2-chloro-4-(6,7-dimethoxyquinolin-4-yloxy)phenyl]-N'-(5-methylisoxazol-3-yl)urea hydrochloride hydrate/X/Y/polysorbate 80/ benzalkonium chloride (BAC)/D-mannitol | X | Y | Concentration (mg/mL) | Mean particle size (nm) |
|---|---|---|---|---|---|
| 55 | 1/0.5/0.5/0.1/0.001/0.1 | HPC | PVP | 1.23 | 149 |
| 56 | 1/0.5/0.5/0.1/0.001/0.1 | HPC | Lecithin | 1.35 | 144 |
| 57 | 1/0.5/0.01/0.1/0.001/0.1 | HPC | PEG | 1.62 | 128 |
| 58 | 1/0.5/0.01/0/0.001/0.1 | PVP | PEG | 2.86 | 65 |
| 59 | 1/0.1/0.0025/0/0/0 | PVP | Sodium lauryl sulfate | 2.44 | 89 |

Example 60

A nanoparticle composition having composition of N-[2-chloro-4-(6,7-dimethoxyquinolin-4-yloxy)phenyl]-N'-(5-methylisoxazol-3-yl)urea hydrochloride hydrate/Pluronic (Registered Trademark) F-68=1 part by weight/0.5 parts by weight and having N-[2-chloro-4-(6,7-dimethoxyquinolin-4-yloxy)phenyl]-N'-(5-methylisoxazol-3-yl)urea hydrochloride hydrate with a concentration of 1.24 mg/mL and a mean particle size of 94 nm was obtained from N-[2-chloro-4-(6, 7-dimethoxyquinolin-4-yloxy)phenyl]-N'-(5-methylisoxazol-3-yl)urea hydrochloride hydrate, Plutonic(Registered Trademark) F-68, and an aqueous glucose solution in accordance with Example 1 except that the thickening agent was changed from hydroxypropylcellulose (HPC) to polyoxyethylene (160) polyoxypropylene (30) glycol (Pluronic(Registered Trademark) F-68, Sigma-Aldrich Co., LLC; the same holds true for the description below), and polysorbate 80, benzalkonium chloride (BAC), and D-mannitol were excluded from the composition.

Example 61

A nanoparticle composition having composition of N-[2-chloro-4-(6,7-dimethoxyquinolin-4-yloxy)phenyl]-N'-(5-methylisoxazol-3-yl)urea hydrochloride hydrate/Pluronic (Registered Trademark) F-127/polysorbate 80=1 part by weight/0.1 parts by weight/0.02 parts by weight and having N-[2-chloro-4-(6,7-dimethoxyquinolin-4-yloxy)phenyl]-N'-(5-methylisoxazol-3-yl)urea hydrochloride hydrate with a concentration of 2.19 mg/mL and a mean particle size of 84 nm was obtained from N-[2-chloro-4-(6,7-dimethoxyquinolin-4-yloxy)phenyl]-N'-(5-methylisoxazol-3-yl)urea hydrochloride hydrate, Pluronic(Registered Trademark) F-127, polysorbate 80, and an aqueous glucose solution in accordance with Example 1 except that: the thickening agent was chloride hydrate with a concentration of 1.56 mg/mL and a mean particle size of 176 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), polysorbate 80, benzalkonium chloride (BAC), D-mannitol, and an aqueous glucose solution in accordance with Example 1 except that the thickening agent was changed from hydroxypropylcellulose (HPC) to polyvinylpyrrolidone (PVP).

Example 63

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)/polysorbate 80/benzalkonium chloride (BAC)/D-mannitol=1 part by weight/1.0 part by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.35 mg/mL and a mean particle size of 149 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), polysorbate 80, benzalkonium chloride (BAC), D-mannitol, and an aqueous glucose solution in accordance with Example 1 except that the thickening agent was changed from hydroxypropylcellulose (HPC) to polyvinylpyrrolidone (PVP).

Example 64

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropyl-β-cyclodextrin (HP-β-CD)/polysorbate 80/benzalkonium chloride (BAC)/D-mannitol=1 part by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.61 mg/mL and a mean particle size of 85 nm was obtained from N-[2-chloro-4-(6,7-dimethoxyquinolin-4-yloxy)phenyl]-N'-(5-methylisoxazol-3-yl)urea hydrochloride hydrate, hydroxypropyl-β-cyclodextrin (HP-β-CD), polysorbate 80, benzalkonium chloride (BAC), D-mannitol, and an aqueous glucose solution in accordance with Example 1 except that the thickening agent was changed from hydroxypropylcellulose (HPC) to hydroxypropyl-β-cyclodextrin (HP-β-CD).

Example 65

A nanoparticle composition having composition of N-[2-chloro-4-(6,7-dimethoxyquinolin-4-yloxy)phenyl]-N'-(5-methylisoxazol-3-yl)urea hydrochloride hydrate/Pluronic (Registered Trademark) F-127/polysorbate 80/benzalkonium chloride (BAC)=1 part by weight/0.5 parts by weight/0.1 parts by weight/0.001 parts by weight and having N-[2-chloro-4-(6,7-dimethoxyquinolin-4-yloxy)phenyl]-N'-(5-methylisoxazol-3-yl)urea hydrochloride hydrate with a concentration of 1.44 mg/mL and a mean particle size of 119 nm was obtained from N-[2-chloro-4-(6,7-dimethoxyquinolin-4-yloxy)phenyl]-N'-(5-methylisoxazol-3-yl)urea hydrochloride hydrate, Pluronic(Registered Trademark) F-127, polysorbate 80, benzalkonium chloride (BAC), and an aqueous D-mannitol solution in accordance with Example 1 except that the thickening agent was changed from hydroxypropylcellulose (HPC) to Pluronic (Registered Trademark) F-127, and the aqueous glucose solution was changed to an aqueous D-mannitol solution.

Example 66

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)/polysorbate 80/benzalkonium chloride (BAC)=1 part by weight/0.5 parts by weight/0.1 parts by weight/0.001 parts by weight and having N-[2-chloro-4-(6,7-dimethoxyquinolin-4-yloxy)phenyl]-N'-(5-methylisoxazol-3-yl)urea hydrochloride hydrate with a concentration of 1.43 mg/mL and a mean particle size of 137 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), polysorbate 80, benzalkonium chloride (BAC), and an aqueous D-mannitol solution in accordance with Example 1 except that the thickening agent was changed from hydroxypropylcellulose (HPC) to polyvinylpyrrolidone (PVP), and the aqueous glucose solution was changed to an aqueous D-mannitol solution.

Example 67

N-[2-Chloro-4-(6,7-dimethoxyquinolin-4-yloxy)phenyl]-N'-(5-methylisoxazol-3-yl)urea hydrochloride hydrate was weighed into a zirconia container (Thinky Corp.) and subsequently prepared into a suspension by the addition of Pluronic(Registered Trademark) F-127, polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glycerol solution, and the zirconia balls were removed through a screen (Clean Media 2000 rpm, 1 min, mill/mix 400 rpm, 1 min) to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/Pluronic(Registered Trademark) F-127/polysorbate 80/benzalkonium chloride (BAC)/D-mannitol=1 part by weight/0.5 parts by weight/0.1 parts by weight/0.001 parts by weight/0.1 parts by weight.

This nanoparticle composition was diluted with an aqueous glycerol solution. As a result of measuring the concentration, N-[2-chloro-4-(6,7-dimethoxyquinolin-4-yloxy)phenyl]-N'-(5-methylisoxazol-3-yl)urea hydrochloride hydrate had a concentration of 1.31 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 432 nm in the nanoparticle composition.

TABLE 11

| Example | Compositional ratio (parts by weight) N-(2-Chloro-4-(6,7-dimethoxyquinolin-4-yloxy)phenyl]-N'-(5-methylisoxazol-3-yl)urea hydrochloride hydrate/X/polysorbate 80/benzalkonium chloride (BAC)/D-mannitol | X | Dispersion media | Concentration (mg/mL) | Mean particle size (nm) |
|---|---|---|---|---|---|
| 60 | 1/0.5/0/0/0 | Pluronic F68 | Aqueous glucose solution | 1.24 | 94 |
| 61 | 1/0.1/0.02/0/0 | Pluronic F127 | Aqueous glucose solution | 2.19 | 84 |
| 62 | 1/0.25/0.1/0.001/0.1 | PVP | Aqueous glucose solution | 1.56 | 176 |
| 63 | 1/1.0/0.1/0.001/0.1 | PVP | Aqueous glucose solution | 1.35 | 149 |
| 64 | 1/0.5/0.1/0.001/0.1 | HPβCD | Aqueous glucose solution | 1.61 | 85 |
| 65 | 1/0.5/0.1/0.001 | Pluronic F127 | Aqueous mannitol solution | 1.44 | 119 |
| 66 | 1/0.5/0.1/0.001 | PVP | Aqueous mannitol solution | 1.43 | 137 |
| 67 | 1/0.5/0.1/0.001/0.1 | Pluronic F127 | Aqueous glycerol solution | 1.31 | 432 |

Example 68

N-[2-Chloro-4-(6,7-dimethoxyquinolin-4-yloxy)phenyl]-N'-(5-methylisoxazol-3-yl)urea hydrochloride hydrate was weighed into a zirconia container (Thinky Corp.) and subsequently prepared into a suspension by the addition of hydroxypropylcellulose (HPC) and water. Zirconia balls (zirconia milling balls, YTZ, diameter: 0.1 mm, Nikkato Corp.) were placed in the container, which was then covered with the lid. Wet milling (mill/mix 1700 rpm, 1 min, loop/10 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)=1 part by weight/0.1 parts by weight.

This nanoparticle composition was purified (13200 rpm, 60 min) using Micro Refrigerated Centrifuge (3740, Kubota Corp.) to adjust the concentration of N-[2-chloro-4-(6,7-dimethoxyquinolin-4-yloxy)phenyl]-N'-(5-methylisoxazol-3-yl)urea hydrochloride hydrate to 2.37 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 76 nm in the nanoparticle composition.

Example 69

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)=1 part by weight/0.3 parts by weight and having N-[2-chloro-4-(6,7-dimethoxyquinolin-4-yloxy)phenyl]-N'-(5-methylisoxazol-3-yl)urea hydrochloride hydrate with a concentration of 1.90 mg/mL and a mean particle size of 90 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), and an aqueous glucose solution in accordance with Example 68 except that the amount of hydroxypropylcellulose (HPC) was changed from 0.1 parts by weight to 0.3 parts by weight.

Example 70

N-[2-Chloro-4-(6,7-dimethoxyquinolin-4-yloxy)phenyl]-N'-(5-methylisoxazol-3-yl)urea hydrochloride hydrate was weighed into a zirconia container (Thinky Corp.) and subsequently prepared into a suspension by the addition of hydroxypropylcellulose (HPC) and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/10 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)=1 part by weight/0.3 Parts by weight.

This nanoparticle composition was purified (13200 rpm, 100 min) using Micro Refrigerated Centrifuge (3740, Kubota Corp.) to adjust the concentration of N-[2-chloro-4-(6,7-dimethoxyquinolin-4-yloxy)phenyl]-N'-(5-methylisoxazol-3-yl)urea hydrochloride hydrate to 1.90 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 75 nm in the nanoparticle composition.

Example 71

N-[2-chloro-4-(6,7-dimethoxyquinolin-4-yloxy)phenyl]-N'-(5-methylisoxazol-3-yl)urea hydrochloride hydrate was weighed into a zirconia container (Thinky Corp.) and subsequently prepared into a suspension by the addition of hydroxypropylcellulose (HPC) and water. Zirconia balls (zirconia milling balls, YTZ, diameter: 0.1 mm, Nikkato Corp.) were placed in the container, which was then covered with the lid. Wet milling (mill/mix 1700 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)=1 part by weight/0.3 parts by weight.

This nanoparticle composition was purified (13200 rpm, 40 min) using Micro Refrigerated Centrifuge (3740, Kubota Corp.) to adjust the concentration of N-[2-chloro-4-(6,7-dimethoxyquinolin-4-yloxy)phenyl]-N'-(5-methylisoxazol-3-yl)urea hydrochloride hydrate to 1.33 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 105 nm in the nanoparticle composition.

Example 72

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)=1 part by weight/0.3 parts by weight and having N-[2-chloro-4-(6,7-dimethoxyquinolin-4-yloxy)phenyl]-N'-(5-methylisoxazol-3-yl)urea hydrochloride hydrate with a concentration of 1.91 mg/mL and a mean particle size of 62 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), and an aqueous glucose solution in accordance with Example 71 except that the thickening agent was changed from hydroxypropylcellulose (HPC) to polyvinylpyrrolidone (PVP).

Example 73

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)=1 part by weight/0.3 parts by weight and having N-[2-chloro-4-(6,7-dimethoxyquinolin-4-yloxy)phenyl]-N'-(5-methylisoxazol-3-yl)urea hydrochloride hydrate with a concentration of 1.21 mg/mL and a mean particle size of 77 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), and an aqueous glucose solution in accordance with Example 68 except that the thickening agent was changed from hydroxypropylcellulose (HPC) to polyvinylpyrrolidone (PVP).

Example 74

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)/polysorbate 80=1 part by weight/0.3 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.75 mg/mL and a mean particle size of 81 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), polysorbate 80, and an aqueous glucose solution in accordance with Example 71 except that the thickening agent was changed from hydroxypropylcellulose (HPC) to polyvinylpyrrolidone (PVP), and the amount of polysorbate was changed from 0 parts by weight to 0.1 parts by weight.

Example 75

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)/polysorbate 80=1 part by weight/0.3 parts by weight/0.01 parts by weight and having N-[2-chloro-4-(6,7-dimethoxyquinolin-4-yloxy)phenyl]-N'-(5-methylisoxazol-3-yl)urea hydrochloride hydrate with a concentration of 1.65 mg/mL and a mean particle size of 60 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), polysorbate 80, and an aqueous glucose solution in accordance with Example 71 except that the thickening agent was changed from hydroxypropylcellulose (HPC) to polyvinylpyrrolidone (PVP), and the amount of polysorbate was changed from 0 parts by weight to 0.01 parts by weight.

Example 76

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)/polysorbate 80=1 part by weight/0.15 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 1.95 mg/mL and a mean particle size of 70 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), polysorbate 80, and an aqueous glucose solution in accordance with Example 71 except that the thickening agent was changed from hydroxypropylcellulose (HPC) to polyvinylpyrrolidone (PVP), and the amount of polysorbate was changed from 0 parts by weight to 0.1 parts by weight.

Example 77

A nanoparticle composition having composition of N-[2-chloro-4-(6,7-dimethoxyquinolin-4-yloxy)phenyl]-N'-(5-methylisoxazol-3-yl)urea hydrochloride hydrate/polyvinylpyrrolidone (PVP)/polysorbate 80=1 part by weight/0.15 parts by weight/0.01 parts by weight and having N-[2-chloro-4-(6,7-dimethoxyquinolin-4-yloxy)phenyl]-N'-(5-methylisoxazol-3-yl)urea hydrochloride hydrate with a concentration of 1.97 mg/mL and a mean particle size of 57 nm was obtained from N-[2-chloro-4-(6,7-dimethoxyquinolin-4-yloxy)phenyl]-N'-(5-methylisoxazol-3-yl)urea hydrochloride hydrate, polyvinylpyrrolidone (PVP), polysorbate 80, and an aqueous glucose solution in accordance with Example 71 except that the thickening agent was changed from hydroxypropylcellulose (HPC) to polyvinylpyrrolidone (PVP), and the amount of polysorbate was changed from 0 parts by weight to 0.01 parts by weight.

Example 78

A nanoparticle composition having composition of N-[2-chloro-4-(6,7-dimethoxyquinolin-4-yloxy)phenyl]-N'-(5-methylisoxazol-3-yl)urea hydrochloride hydrate/Pluronic (Registered Trademark) F-127=1 part by weight/0.3 parts by weight and having N-[2-chloro-4-(6,7-dimethoxyquinolin-4-yloxy)phenyl]-N'-(5-methylisoxazol-3-yl)urea hydrochloride hydrate with a concentration of 2.59 mg/mL and a mean particle size of 96 nm was obtained from N-[2-chloro-4-(6,7-dimethoxyquinolin-4-yloxy)phenyl]-N'-(5-methylisoxazol-3-yl)urea hydrochloride hydrate, Pluronic(Registered Trademark) F-127, and an aqueous glucose solution in accordance with Example 71 except that the thickening agent was changed from hydroxypropylcellulose (HPC) to Pluronic(Registered Trademark) F-127.

Example 79

A nanoparticle composition having composition of N-[2-chloro-4-(6,7-dimethoxyquinolin-4-yloxy)phenyl]-N'-(5-methylisoxazol-3-yl)urea hydrochloride hydrate/Pluronic (Registered Trademark) F-127=1 part by weight/0.3 parts by weight and having N-[2-chloro-4-(6,7-dimethoxyquinolin-4-yloxy)phenyl]-N'-(5-methylisoxazol-3-yl)urea hydrochloride hydrate with a concentration of 1.48 mg/mL and a mean particle size of 133 nm was obtained from N-[2-chloro-4-(6,7-dimethoxyquinolin-4-yloxy)phenyl]-N'-(5-methylisoxazol-3-yl)urea hydrochloride hydrate, Pluronic(Registered Trademark) F-127, and an aqueous glucose solution in accordance with Example 68 except that the thickening agent was changed from hydroxypropylcellulose (HPC) to Pluronic(Registered Trademark) F-127.

TABLE 12

| Example | Compositional ratio (parts by weight) N-[2-chloro-4-(6,7-dimethoxyquinolin-4-yloxy)phenyl)-N'-(5-methylisoxazol-3-yl)urea hydrochloride hydrate/X/polysorbate 80 | X | Milling conditions | Concentration (mg/mL) | Mean particle size (nm) |
|---|---|---|---|---|---|
| 68 | 1/0.1/0 | HPC | 1700 rpm 10 times | 2.37 | 76 |

TABLE 12-continued

| Example | Compositional ratio (parts by weight) N-[2-chloro-4-(6,7-dimethoxyquinolin-4-yloxy)phenyl]-N'-(5-methylisoxazol-3-yl)urea hydrochloride hydrate/X/polysorbate 80 | X | Milling conditions | Concentration (mg/mL) | Mean particle size (nm) |
|---|---|---|---|---|---|
| 69 | 1/0.3/0 | HPC | 1700 rpm 10 times | 1.90 | 90 |
| 70 | 1/0.3/0 | HPC | 2000 rpm 10 times | 1.90 | 75 |
| 71 | 1/0.3/0 | HPC | 1700 rpm 30 times | 1.33 | 105 |
| 72 | 1/0.3/0 | PVP | 1700 rpm 30 times | 1.91 | 62 |
| 73 | 1/0.3/0 | PVP | 1700 rpm 10 times | 1.21 | 77 |
| 74 | 1/0.3/0.1 | PVP | 1700 rpm 30 times | 1.75 | 81 |
| 75 | 1/0.3/0.01 | PVP | 1700 rpm 30 times | 1.65 | 60 |
| 76 | 1/0.15/0.1 | PVP | 1700 rpm 30 times | 1.95 | 70 |
| 77 | 1/0.15/0.01 | PVP | 1700 rpm 30 times | 1.97 | 57 |
| 78 | 1/0.3/0 | Pluronic F127 | 1700 rpm 30 times | 2.59 | 96 |
| 79 | 1/0.3/0 | Pluronic F127 | 1700 rpm 10 times | 1.48 | 133 |

Example 80

N-[2-Chloro-4-(6,7-dimethoxyquinolin-4-yloxy)phenyl]-N'-(5-methylisoxazol-3-yl)urea hydrochloride hydrate was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=0.1 parts by weight/0.5 parts by weight/0.1 parts by weight/0.001 parts by weight/0.1 parts by weight.

As a result of measuring the concentration of this nanoparticle composition, N-[2-chloro-4-(6,7-dimethoxyquinolin-4-yloxy)phenyl]-N'-(5-methylisoxazol-3-yl)urea hydrochloride hydrate had a concentration of 0.90 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 400 nm in the nanoparticle composition.

Example 81

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=0.1 parts by weight/0.05 parts by weight/0.01 parts by weight/0.0001 parts by weight/0.01 parts by weight and having N-[2-chloro-4-(6,7-dimethoxyquinolin-4-yloxy)phenyl]-N'-(5-methylisoxazol-3-yl)urea hydrochloride hydrate with a concentration of 1.12 mg/mL and a mean particle size of 226 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 80 except that: the amount of hydroxypropylcellulose (HPC) was changed from 0.5 parts by weight to 0.05 parts by weight; the amount of polysorbate 80 was changed from 0.1 parts by weight to 0.01 parts by weight; the amount of benzalkonium chloride (BAC) was changed from 0.001 parts by weight to 0.0001 parts by weight; and the amount of D-mannitol was changed from 0.1 parts by weight to 0.01 parts by weight.

Example 82

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylmethylcellulose (HPMC)/polysorbate 80/benzalkonium chloride (BAC)/D-mannitol=0.1 parts by weight/0.05 parts by weight/0.01 parts by weight/0.0001 parts by weight/0.01 parts by weight and having N-[2-chloro-4-(6,7-dimethoxyquinolin-4-yloxy)phenyl]-N'-(5-methylisoxazol-3-yl)urea hydrochloride hydrate with a concentration of 0.77 mg/mL and a mean particle size of 268 nm was obtained from N-[2-chloro-4-(6,7-dimethoxyquinolin-4-yloxy)phenyl]-N'-(5-methylisoxazol-3-yl)urea hydrochloride hydrate, hydroxypropylmethylcellulose (HPMC), polysorbate 80, benzalkonium chloride (BAC), D-mannitol, and an aqueous glucose solution in accordance with Example 80 except that: the thickening agent was changed from hydroxypropylcellulose (HPC) to hydroxypropylmethylcellulose (HPMC); the amount of polysorbate 80 was changed from 0.1 parts by weight to 0.01 parts by weight; the amount of benzalkonium chloride (BAC) was changed from 0.001 parts by weight to 0.0001 parts by weight; and the amount of D-mannitol was changed from 0.1 parts by weight to 0.01 parts by weight.

Example 83

A nanoparticle composition having composition of N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=0.2 parts by weight/0.5 parts by weight/0.1 parts by weight/0.001 parts by weight/0.1 parts by weight and having N-[2-chloro-4-(6,7-dimethoxyquinolin-4-yloxy)phenyl]-N'-(5-methylisoxazol-3-yl)urea hydrochloride hydrate with a concentration of 2.07 mg/mL and a mean particle size of 258 nm was obtained from N-[2-chloro-4-(6,7-dimethoxyquinolin-4-yloxy)phenyl]-N'-(5-methylisoxazol-3-yl)urea hydrochloride hydrate, hydroxypropylcellulose (HPC), polysorbate 80, benzalkonium chloride (BAC), D-mannitol, and an aqueous glucose solution in accordance with Example 80 except that the amount of N-[2-chloro-4-(6,7-dimethoxyquinolin-4-yloxy)phenyl]-N'-(5-methylisoxazol-3-yl)urea hydrochloride hydrate was changed from 0.1 parts by weight to 0.2 parts by weight.

Example 84

N-[2-Chloro-4-(6,7-dimethoxyquinolin-4-yloxy)phenyl]-N'-(5-methylisoxazol-3-yl)urea hydrochloride hydrate was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter 1.0 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=0.2 parts by weight/0.5 parts by weight/0.1 parts by weight/0.001 parts by weight/0.1 parts by weight.

As a result of measuring the concentration of this nanoparticle composition, N-[2-chloro-4-(6,7-dimethoxyquinolin-4-yloxy)phenyl]-N'-(5-methylisoxazol-3-yl)urea hydrochloride hydrate had a concentration of 2.05 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 365 nm in the nanoparticle composition.

TABLE 13

| Example | Compositional ratio (parts by weight) N-[2-chloro-4-(6,7-dimethoxyquinolin-4-yloxy)phenyl]-N'-(5-methylisoxazol-3-yl)urea hydrochloride hydrate/X/polysorbate 80/ benzalkonium chloride (BAC)/D-mannitol | X | Zirconia ball diameter (mm) | Concentration (mg/mL) | Mean particle size (nm) |
|---|---|---|---|---|---|
| 80 | 0.1/0.5/0.1/0.001/0.1 | HPC | 0.1 | 0.90 | 400 |
| 81 | 0.1/0.05/0.01/0.0001/0.01 | HPC | 0.1 | 1.12 | 226 |
| 82 | 0.1/0.05/0.01/0.0001/0.01 | HPMC | 0.1 | 0.77 | 268 |
| 83 | 0.2/0.5/0.1/0.001/0.1 | HPC | 0.1 | 2.07 | 258 |
| 84 | 0.2/0.5/0.1/0.001/0.1 | HPC | 1.0 | 2.05 | 365 |

Reference Example 2

1-(2-(tert-Butyl)-4-(3,5-dimethylisoxazol-4-yl)-1H-imidazol-5-yl)-3-(4-((6,7-dimethoxyquinolin-4-yl)oxy)-3-fluorophenyl)urea was prepared according to the method disclosed in Japanese Unexamined Patent Application Publication No. 2003-12668.

Example 85

1-(2-(tert-Butyl)-4-(3,5-dimethylisoxazol-4-yl)-1H-imidazol-5-yl)-3-(4-((6,7-dimethoxyquinolin-4-yl)oxy)-3-fluorophenyl)urea was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition. The composition of the nanoparticle composition was set to 1-(2-(tert-butyl)-4-(3,5-dimethylisoxazol-4-yl)-1H-imidazol-5-yl)-3-(4-((6,7-dimethoxyquinolin-4-yl)oxy)-3-fluorophenyl)urea/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

As a result of measuring the concentration of this nanoparticle composition, 1-(2-(tert-butyl)-4-(3,5-dimethylisoxazol-4-yl)-1H-imidazol-5-yl)-3-(4-((6,7-dimethoxyquinolin-4-yl)oxy)-3-fluorophenyl)urea had a concentration of 7.80 mg/mL.

As a result of assaying the nanoparticle composition using Zeta Sizer (Malvern instruments Nano series), 1-(2-(tert-butyl)-4-(3,5-dimethylisoxazol-4-yl)-1H-imidazol-5-yl)-3-

(4-((6,7-dimethoxyquinolin-4-yl)oxy)-3-fluorophenyl)urea had a mean particle size of 211 nm in the nanoparticle composition.

Example 86

The nanoparticle composition prepared in Example 85 was purified using Micro Refrigerated Centrifuge (3740, Kubota Corp.) to adjust the concentration of 1-(2-(tert-butyl)-4-(3,5-dimethylisoxazol-4-yl)-1H-imidazol-5-yl)-3-(4-((6,7-dimethoxyquinolin-4-yl)oxy)-3-fluorophenyl)urea to 0.77 mg/mL.

As a result of assaying the nanoparticle composition using Zeta Sizer (Malvern instruments Nano series), 1-(2-(tert-butyl)-4-(3,5-dimethylisoxazol-4-yl)-1H-imidazol-5-yl)-3-(4-((6,7-dimethoxyquinolin-4-yl)oxy)-3-fluorophenyl)urea had a mean particle size of 133 nm in the nanoparticle composition.

Reference Example 3

1-(4-((6,7-Dimethoxyquinolin-4-yl)oxy)-2-fluorophenyl)-3-(1,5,5-trimethyl-4,5,6,7-tetrahydro-1H-indazol-3-yl)urea hydrochloride was prepared according to the method disclosed in Japanese Unexamined Patent Application Publication No. 2003-12668.

Example 87

A nanoparticle composition having composition of 1-(4-((6,7-dimethoxyquinolin-4-yl)oxy)-2-fluorophenyl)-3-(1,5,5-trimethyl-4,5,6,7-tetrahydro-1H-indazol-3-yl)urea hydrochloride/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having 1-(4-((6,7-dimethoxyquinolin-4-yl)oxy)-2-fluorophenyl)-3-(1,5,5-trimethyl-4,5,6,7-tetrahydro-1H-indazol-3-yl)urea hydrochloride with a concentration of 13.27 mg/mL and a mean particle size of 368 nm was obtained from 1-(4-((6,7-dimethoxyquinolin-4-yl)oxy)-2-fluorophenyl)-3-(1,5,5-trimethyl-4,5,6,7-tetrahydro-1H-indazol-3-yl)urea hydrochloride, hydroxypropylcellulose (HPC), polysorbate 80, benzalkonium chloride (BAC), D-mannitol, and an aqueous glucose solution in accordance with Example 85 except that 1-(2-(tert-butyl)-4-(3,5-dimethylisoxazol-4-yl)-1H-imidazol-5-yl)-3-(4-((6,7-dimethoxyquinolin-4-yl)oxy)-3-fluorophenyl)urea was changed to 1-(4-((6,7-dimethoxyquinolin-4-yl)oxy)-2-fluorophenyl)-3-(1,5,5-trimethyl-4,5,6,7-tetrahydro-1H-indazol-3-yl)urea hydrochloride.

Example 88

The nanoparticle composition prepared in Example 87 was purified using Micro Refrigerated Centrifuge (3740, Kubota Corp.) to adjust the concentration of 1-(4-((6,7-dimethoxyquinolin-4-yl)oxy)-2-fluorophenyl)-3-(1,5,5-trimethyl-4,5,6,7-tetrahydro-1H-indazol-3-yl)urea hydrochloride to 3.75 mg/mL.

As a result of assaying the nanoparticle composition using Zeta Sizer (Malvern instruments Nano series), 1-(4-((6,7-dimethoxyquinolin-4-yl)oxy)-2-fluorophenyl)-3-(1,5,5-trimethyl-4,5,6,7-tetrahydro-1H-indazol-3-yl)urea hydrochloride had a mean particle size of 617 nm in the nanoparticle composition.

Reference Example 4

1-(4-((6,7-Dimethoxyquinolin-4-yl)oxy)-3-fluorophenyl)-3-(1,5,5-trimethyl-4,5,6,7-tetrahydro-1H-indazol-3-yl)urea hydrochloride was prepared according to the method disclosed in Japanese Unexamined Patent Application Publication No. 2003-12668.

Example 89

A nanoparticle composition having composition of 1-(4-((6,7-dimethoxyquinolin-4-yl)oxy)-3-fluorophenyl)-3-(1,5,5-trimethyl-4,5,6,7-tetrahydro-1H-indazol-3-yl)urea hydrochloride/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having 1-(4-((6,7-dimethoxyquinolin-4-yl)oxy)-3-fluorophenyl)-3-(1,5,5-trimethyl-4,5,6,7-tetrahydro-1H-indazol-3-yl)urea hydrochloride with a concentration of 6.98 mg/mL and a mean particle size of 260 nm was obtained from 1-(4-((6,7-dimethoxyquinolin-4-yl)oxy)-3-fluorophenyl)-3-(1,5,5-trimethyl-4,5,6,7-tetrahydro-1H-indazol-3-yl)urea hydrochloride, hydroxypropylcellulose (HPC), polysorbate 80, benzalkonium chloride (BAC), D-mannitol, and an aqueous glucose solution in accordance with Example 85 except that 1-(2-(tert-butyl)-4-(3,5-dimethylisoxazol-4-yl)-1H-imidazol-5-yl)-3-(4-((6,7-dimethoxyquinolin-4-yl)oxy)-3-fluorophenyl)urea was changed to 1-(4-((6,7-dimethoxyquinolin-4-yl)oxy)-3-fluorophenyl)-3-(1,5,5-trimethyl-4,5,6,7-tetrahydro-1H-indazol-3-yl)urea hydrochloride.

Reference Example 5

1-(4-((6,7-Dimethoxyquinolin-4-yl)oxy)phenyl)-3-(5-isopropylisoxazol-3-yl)urea was prepared according to the method disclosed in Japanese Unexamined Patent Application Publication No. 2003-12668.

Example 90

A nanoparticle composition having composition of 1-(4-((6,7-dimethoxyquinolin-4-yl)oxy)phenyl)-3-(5-isopropylisoxazol-3-yl)urea/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having 1-(4-((6,7-dimethoxyquinolin-4-yl)oxy)phenyl)-3-(5-isopropylisoxazol-3-yl)urea with a concentration of 5.22 mg/mL and a mean particle size of 169 nm was obtained from 1-(4-((6,7-dimethoxyquinolin-4-yl)oxy)phenyl)-3-(5-isopropylisoxazol-3-yl)urea, hydroxypropylcellulose (HPC), polysorbate 80, benzalkonium chloride (BAC), D-mannitol, and an aqueous glucose solution in accordance with Example 85 except that 1-(2-(tert-butyl)-4-(3,5-dimethylisoxazol-4-yl)-1H-imidazol-5-yl)-3-(4-((6,7-dimethoxyquinolin-4-yl)oxy)-3-fluorophenyl)urea was changed to 1-(4-((6,7-dimethoxyquinolin-4-yl)oxy)phenyl)-3-(5-isopropylisoxazol-3-yl)urea.

Example 91

The nanoparticle composition prepared in Example 90 was purified using Micro Refrigerated Centrifuge (3740, Kubota Corp.) to adjust the concentration of 1-(4-((6,7-dimethoxyquinolin-4-yl)oxy)phenyl)-3-(5-isopropylisoxazol-3-yl)urea to 1.34 mg/mL.

As a result of assaying the nanoparticle composition using Zeta Sizer (Malvern instruments Nano series), 1-(4-((6,7- dimethoxyquinolin-4-yl)oxy)phenyl)-3-(5-isopropylisoxazol-3-yl)urea had a mean particle size of 145 nm in the nanoparticle composition.

Reference Example 6

1-(4-((6,7-Dimethoxyquinolin-4-yl)oxy)phenyl)-3-(5-methylisoxazol-3-yl)urea hydrochloride was prepared according to the method disclosed in Japanese Unexamined Patent Application Publication No. 2003-12668.

Example 92

A nanoparticle composition having composition of 1-(4-((6,7-dimethoxyquinolin-4-yl)oxy)phenyl)-3-(5-methylisoxazol-3-yl)urea hydrochloride/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having 1-(4-((6,7-dimethoxyquinolin-4-yl)oxy)phenyl)-3-(5-methylisoxazol-3-yl)urea hydrochloride with a concentration of 10.69 mg/mL and a mean particle size of 269 nm was obtained from 1-(4-((6,7-dimethoxyquinolin-4-yl)oxy)phenyl)-3-(5-methylisoxazol-3-yl)urea hydrochloride, hydroxypropylcellulose (HPC), polysorbate 80, benzalkonium chloride (BAC), D-mannitol, and an aqueous glucose solution in accordance with Example 85 except that 1-(2-(tert-butyl)-4-(3,5-dimethylisoxazol-4-yl)-1H-imidazol-5-yl)-3-(4-((6,7-dimethoxyquinolin-4-yl)oxy)-3-fluorophenyl)urea was changed to 1-(4-((6,7-dimethoxyquinolin-4-yl)oxy)phenyl)-3-(5-methylisoxazol-3-yl)urea hydrochloride.

Example 93

The nanoparticle composition prepared in Example 92 was purified using Micro Refrigerated Centrifuge (3740, Kubota Corp.) to adjust the concentration of 1-(4-((6,7-dimethoxyquinolin-4-yl)oxy)phenyl)-3-(5-methylisoxazol-3-yl)urea hydrochloride to 1.34 mg/mL.

As a result of assaying the nanoparticle composition using Zeta Sizer (Malvern instruments Nano series), 1-(4-((6,7-dimethoxyquinolin-4-yl)oxy)phenyl)-3-(5-methylisoxazol-3-yl)urea hydrochloride had a mean particle size of 169 nm in the nanoparticle composition.

Reference Example 7

1-(5-(tert-Butyl)isoxazol-3-yl)-3-(4-((6,7-dimethoxyquinolin-4-yl)oxy)-3-methoxyphenyl)urea hydrochloride was prepared according to the method disclosed in Japanese Unexamined Patent Application Publication No. 2003-12668.

Example 94

A nanoparticle composition having composition of 1-(5-(tert-butyl)isoxazol-3-yl)-3-(4-((6,7-dimethoxyquinolin-4-yl)oxy)-3-methoxyphenyl)urea hydrochloride/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having 1-(5-(tert-butyl)isoxazol-3-yl)-3-(4-((6,7-dimethoxyquinolin-4-yl)oxy)-3-methoxyphenyl)urea hydrochloride with a concentration of 10.86 mg/mL and a mean particle size of 163 nm was obtained from 1-(5-(tert-butyl)isoxazol-3-yl)-3-(4-((6,7-dimethoxyquinolin-4-yl)oxy)-3-methoxyphenyl)urea hydrochloride, hydroxypropylcellulose (HPC), polysorbate 80, benzalkonium chloride (BAC), D-mannitol, and an aqueous glucose solution in accordance with Example 85 except that 1-(2-(tert-butyl)-4-(3,5-dimethylisoxazol-4-yl)-1H-imidazol-5-yl)-3-(4-((6,7-dimethoxyquinolin-4-yl)oxy)-3-fluorophenyl)urea was changed to 1-(5-(tert-butyl)isoxazol-3-yl)-3-(4-((6,7-dimethoxyquinolin-4-yl)oxy)-3-methoxyphenyl)urea hydrochloride.

Example 95

The nanoparticle composition prepared in Example 94 was purified using Micro Refrigerated Centrifuge (3740, Kubota Corp.) to adjust the concentration of 1-(5-(tert-butyl)isoxazol-3-yl)-3-(4-((6,7-dimethoxyquinolin-4-yl)oxy)-3-methoxyphenyl)urea hydrochloride to 1.54 mg/mL.

As a result of assaying the nanoparticle composition using Zeta Sizer (Malvern instruments Nano series), 1-(5-(tert-butyl)isoxazol-3-yl)-3-(4-((6,7-dimethoxyquinolin-4-yl)oxy)-3-methoxyphenyl)urea hydrochloride had a mean particle size of 83 nm in the nanoparticle composition.

TABLE 14

| Example | Compositional ratio (parts by weight) X/hydroxypropylcellulose (HPC)/polysorbate 80/benzalkonium chloride (BAC)/D-mannitol | X | Concentration (mg/mL) | Mean particle size (nm) |
|---|---|---|---|---|
| 85 | 1/0.5/0.1/0.001/0.1 | N-[2-(tert-Butyl)-4-(3,5-dimethyl-1,2-oxazol-4-yl)-1H-imidazol-5-yl]-N'-{4*[(6,7-dimethoxyquinolin-4-yl)oxy]-3-fluorophenyl)urea | 7.80 | 211 |
| 86 | 1/0.5/0.1/0.001/0.1 | N-[2-(tert-Butyl)-4-(3,5-dimethyl-1,2-oxazol-4-yl)-1H-imidazol-5-yl]-N'-{4-[(6,7-dimethoxyquinolin-4-yl)oxy]-3-fluorophenyl)urea | 0.77 | 132 |
| 87 | 1/0.5/0.1/0.001/0.1 | N-{4-[(6,7-Dimethoxyquinolin-4-yl)oxy]-2-fluorophenyl-N'-(1,5,5-trimethyl-4,5,6,7-tetrahydro-1H-indazole-3-yl)urea hydrochloride | 13.27 | 368 |
| 88 | 1/1.5/0.1/0.001/0.1 | N-{4-[(6,7-Dimethoxyquinolin-4-yl)oxy]-2-fluorophenyl-N'-(1,5,5-trimethyl-4,5,6,7-tetrahydro-1H-indazole-3-yl)urea hydrochloride | 3.75 | 617 |
| 89 | 1/0.5/0.1/0.001/0.1 | N-{4-[(6,7-Dimethoxyquinolin-4-yl)oxy]-3-fluorophenyl-N'-(1,5,5-trimethyl-4,5,6,7-tetrahydro-1H-indazol-3-urea hydrochloride | 6.98 | 260 |
| 90 | 1/0.5/0.1/0.001/0.1 | N-{4-[(6,7-Dimethoxyquinolin-4-yl)oxy]phenyl}-N'-(5-isopropyl-1,2-oxazol-3-yl)urea | 5.22 | 169 |
| 91 | 1/0.5/0.1/0.001/0.1 | N-{4-[(6,7-Dimethoxyquinolin-4-yl)oxy]phenyl}-N'-(5-isopropyl-1,2-oxazol-3-yl)urea | 1.34 | 145 |

TABLE 14-continued

| Example | Compositional ratio (parts by weight) X/hydroxypropylcellulose (HPC)/polysorbate 80/benzalkonium chloride (BAC)/D-mannitol | X | Concentration (mg/mL) | Mean particle size (nm) |
|---|---|---|---|---|
| 92 | 1/0.5/0.1/0.001/0.1 | N-{4-[(6,7-Dimethoxyquinolin-4-yl)oxy]phenyl}-N'-(5-methyl-1,2-oxazol-3-yl)urea hydrochloride | 10.69 | 269 |
| 93 | 1/0.5/0.1/0.001/0.1 | N-{4-[(6,7-Dimethoxyquinolin-4-yl)oxy]phenyl}-N'-(5-methyl-1,2-oxazol-3-yl)urea hydrochloride | 1.34 | 169 |
| 94 | 1/0.5/0.1/0.001/0.1 | N-[5-(tert-Butyl)-1,2-oxazol-3-yl]-N'-{4-[(6,7-dimethoxyquinolin-4-yl)oxy]-3-methoxyphenyl}urea hydrochloride | 10.58 | 163 |
| 95 | 1/0.5/0.1/0.001/0.1 | N-[5-tert-Butyl)-1,2-oxazol-3-yl]-N'-{4-[(6,7-dimethoxyquinolin-4-yl)oxy]-3-methoxyphenyl}urea hydrochloride | 1.54 | 83 |

Example 96

N-[2-Chloro-4-(6,7-dimethoxyquinolin-4-yloxy)phenyl]-N'-(5-methylisoxazol-3-yl)urea hydrochloride hydrate was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

This nanoparticle composition was diluted with glycerol. The composition of the nanoparticle composition was set to N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol=0.25 parts by weight/0.125 parts by weight/0.025 parts by weight/0.00025 parts by weight/0.025 parts by weight.

As a result of measuring the concentration of this nanoparticle composition, N-[2-chloro-4-(6,7-dimethoxyquinolin-4-yloxy)phenyl]-N'-(5-methylisoxazol-3-yl)urea hydrochloride hydrate had a concentration of 2.06 mg/mL.

As a result of assaying the nanoparticle composition using Zeta Sizer (Malvern instruments Nano series), N-[2-chloro-4-(6,7-dimethoxyquinolin-4-yloxy)phenyl]-N'-(5-methylisoxazol-3-yl)urea hydrochloride hydrate had a mean particle size of 206 nm in the nanoparticle composition.

TABLE 15

| Example | Compositional ratio (parts by weight) N-[2-chloro-4-(6,7-dimethoxyquinolin-4-yloxy)phenyl]-N'-(5-methylisoxazol-3-yl)urea hydrochloride hydrate/hydroxypropylcellulose (HPC)/polysorbate 80/benzalkonium chloride (BAC)/D-mannitol | Concentration (mg/mL) | Mean particle size (nm) | Dispersion media |
|---|---|---|---|---|
| 96 | 0.25/0.125/0.025/0.00025/0.025 | 2.06 | 206 | Aqueous glycerol solution |

Reference Example 8

[4-[N-(2,3-Dimethyl-2H-indazol-6-yl)-N-methylamino]pyrimidin-2-ylamino]-2-methylbenzenesulfonamide hydrochloride (Synkinase; the same holds true for the description below) was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min), by the addition of an aqueous glucose solution, and the zirconia balls were removed through a screen (Clean Media 2000 rpm, 1 min, mill/mix 400 rpm, 1 min) to obtain a suspension.

The composition of the suspension was set to [4-[N-(2,3-dimethyl-2H-indazol-6-yl)-N-methylamino]pyrimidin-2-ylamino]-2-methylbenzenesulfonamide hydrochloride/hydroxypropylcellulose (HPC)/polysorbate 80/benzalkonium chloride (BAC)/D-mannitol=1.0 part by weight/0.5 parts by weight/0.1 parts by weight/0.001 parts by weight/0.1 parts by weight.

As a result of measuring the concentration of this suspension, [4-[N-(2,3-dimethyl-2H-indazol-6-yl)-N-methylamino]pyrimidin-2-ylamino]-2-methylbenzenesulfonamide hydrochloride had a concentration of 3.97 mg/mL.

The suspension was purified (13200 rpm, 3 min) using Micro Refrigerated Centrifuge (3740, Kubota Corp.). As a result, the supernatant became a clear liquid. Specifically, this method failed to produce a nanoparticle composition and produced a solution having [4-[N-(2,3-dimethyl-2H- indazol-6-yl)-N-methylamino]pyrimidin-2-ylamino]-2-methylbenzenesulfonamide hydrochloride with a concentration of 294 mg/mL.

Example 98

1-[[4-[(4-Fluoro-2-methyl-1H-indol-5-yl)oxy]-6-methoxyquinolin-7-yl]oxymethyl]cyclopropan-1-amine (Shanghai Lollane Biological Technology Co., Ltd.; the same holds true for the description below) was weighed into a zirconia container (Thinky Corp.) and subsequently prepared into a suspension by the addition of hydroxypropylcellulose (HPC), polysorbate 80, benzalkonium chloride BAC, D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/60 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 1-[[4-[(4-fluoro-2-methyl-1H-indol-5-yl)oxy]-6-methoxyquinolin-7-yl]oxymethyl]cyclopropan-1-amine/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

As a result of measuring the concentration of this nanoparticle composition, 1-[[4-[(4-fluoro-2-methyl-1H-indol-5-yl)oxy]-6-methoxyquinolin-7-yl]oxymethyl]cyclopropan-1-amine had a concentration of 9.69 mg/mL.

As a result of assaying the nanoparticle composition using Zeta Sizer (Malvern instruments Nano series), 1-[[4-[(4-fluoro-2-methyl-1H-indol-5-yl)oxy]-6-methoxyquinolin-7-yl]oxymethyl]cyclopropan-1-amine had a mean particle size of 164 nm in the nanoparticle composition.

Example 99

The nanoparticle composition prepared in Example 98 was purified (17000 rpm, 5 min) using Micro Refrigerated Centrifuge (3740, Kubota Corp.) to adjust the concentration of 1-[[4-[(4-fluoro-2-methyl-1H-indol-5-yl)oxy]-6-methoxyquinolin-7-yl]oxymethyl]cyclopropan-1-amine to 6.67 mg/mL.

As a result of assaying the nanoparticle composition using Zeta Sizer (Malvern instruments Nano series), 1-[[4-[(4-fluoro-2-methyl-1H-indol-5-yl)oxy]-6-methoxyquinolin-7-yl]oxymethyl]cyclopropan-1-amine had a mean particle size of 188 nm in the nanoparticle composition.

Example 100

The nanoparticle composition prepared in Example 98 was purified (17000 rpm, 15 min) using Micro Refrigerated Centrifuge (3740, Kubota Corp.) to adjust the concentration of 1-[[4-[(4-fluoro-2-methyl-1H-indol-5-yl)oxy]-6-methoxyquinolin-7-yl]oxymethyl]cyclopropan-1-amine to 4.78 mg/mL.

As a result of assaying the nanoparticle composition using Zeta Sizer (Malvern instruments Nano series), 1-[[4-[(4-fluoro-2-methyl-1H-indol-5-yl)oxy]-6-methoxyquinolin-7-yl]oxymethyl]cyclopropan-1-amine had a mean particle size of 165 nm in the nanoparticle composition.

Example 101

The nanoparticle composition prepared in the same way as in Example 98 was purified (17000 rpm, 100 min) using Micro Refrigerated Centrifuge (3740, Kubota Corp.) to adjust the concentration of 1-[[4-[(4-fluoro-2-methyl-1H-indol-5-yl)oxy]-6-methoxyquinolin-7-yl]oxymethyl]cyclopropan-1-amine to 2.34 mg/mL.

As a result of assaying the nanoparticle composition using Zeta Sizer (Malvern instruments Nano series), 1-[[4-[(4-fluoro-2-methyl-1H-indol-5-yl)oxy]-6-methoxyquinolin-7-yl]oxymethyl]cyclopropan-1-amine had a mean particle size of 106 nm in the nanoparticle composition.

Example 102

The nanoparticle composition prepared in Example 98 was purified (17000 rpm, 75 min) using Micro Refrigerated Centrifuge (3740, Kubota Corp.) to adjust the concentration of 1-[[4-[(4-fluoro-2-methyl-1H-indol-5-yl)oxy]-6-methoxyquinolin-7-yl]oxymethyl]cyclopropan-1-amine to 1.77 mg/mL.

As a result of assaying the nanoparticle composition using Zeta Sizer (Malvern instruments Nano series), 1-[[4-[(4-fluoro-2-methyl-1H-indol-5-yl)oxy]-6-methoxyquinolin-7-yl]oxymethyl]cyclopropan-1-amine had a mean particle size of 118 nm in the nanoparticle composition.

| Example | Compositional ratio (parts by weight) 1-[[4-[(4-fluoro-2-methyl-1H-indol-5-yl)oxy-6-methoxyquinolin-7-yl]oxymethyl]cyclopropan-1-amine/hydroxycellulose (HPC)/polysorbate 80/benzalkonium chloride (BAC)/D-mannitol | Concentration (mg/mL) | Mean particle size (nm) |
|---|---|---|---|
| 98 | 1/0.5/0.1/0.001/0.1 | 9.69 | 164 |
| 99 | 1/0.5/0.1/0.001/0.1 | 6.67 | 138 |
| 100 | 1/0.5/0.1/0.001/0.1 | 4.78 | 165 |

-continued

| Example | Compositional ratio (parts by weight) 1-[[4-[(4-fluoro-2-methyl-1H-indol-5-yl)oxy-6-methoxyquinolin-7-yl]oxymethyl]cyclopropan-1-amine/hydroxycellulose (HPC)/polysorbate 80/benzalkonium chloride (BAC)/D-mannitol | Concentration (mg/mL) | Mean particle size (nm) |
|---|---|---|---|
| 101 | 1/0.5/0.1/0.001/0.1 | 2.34 | 106 |
| 102 | 1/0.5/0.1/0.001/0.1 | 1.77 | 118 |

Reference Example 9

4-[3-Chloro-4-(cyclopropylcarbamoylamino)phenoxy]-7-methoxyquinoline-6-carboxamide (Shanghai Lollane Biological Technology Co., Ltd.; the same holds true for the description below) was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/10 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 4-[3-chloro-4-(cyclopropylcarbamoylamino)phenoxy]-7-methoxyquinoline-6-carboxamide/hydroxypropylcellulose (HPC)/Tween 80/benzalkonium chloride (BAC)/D-mannitol=1 part by weight/0.5 parts by weight/0.1 parts by weight/0.001 parts by weight/0.1 parts by weight.

This nanoparticle composition was purified (17000 rpm, 10 min) using Micro Refrigerated Centrifuge (3740, Kubota Corp.) to adjust the concentration of 4-[3-chloro-4-(cyclopropylcarbamoylamino)phenoxy]-7-methoxyquinoline-6-carboxamide to 239 mg/mL.

As a result of assaying the nanoparticle composition using Zeta Sizer (Malvern instruments Nano series), 4-[3-chloro-4-(cyclopropylcarbamoylamino)phenoxy]-7-methoxyquinoline-6-carboxamide had a mean particle size of 228 nm in the nanoparticle composition.

Reference Example 10

Methyl (3Z)-3-[({4-[N-methyl-2-(4-methylpiperazin-1-yl)acetamido]phenyl}amino)(phenyl)methylidene]-2-oxo-2·3-dihydro-1H-indole-6-carboxylate (RennoTech Co., Ltd.; the same holds true for the description below) was weighed into a zirconia container (Thinky Corp.) and subsequently prepared into a suspension by the addition of hydroxypropylcellulose (HPC, polysorbate 80, benzalkonium chloride (BAC, D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to methyl (3Z)-3-[({4-[N-methyl-2-(4-methylpiperazin-1-yl)acetamido]phenyl}amino)(phenyl)methylidene]-2-oxo-2·3-dihydro-1H-indole-6-carboxylate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

This nanoparticle composition was purified (17000 rpm, 20 min) using Micro Refrigerated Centrifuge (3740, Kubota Corp.) to adjust the concentration of methyl (3Z)-3-[({4-[N-methyl-2-(4-methylpiperazin-1-yl)acetamido]phenyl}amino)(phenyl)methylidene]-2-oxo-2·3-dihydro-1H-indole-6-carboxylate to 1.60 mg/mL.

As a result of assaying the nanoparticle composition using Zeta Sizer (Malvern instruments Nano series), methyl (3Z)-3-[({4-[N-methyl-2-(4-methylpiperazin-1-yl)acetamido]phenyl}amino)(phenyl)methylidene]-2-oxo-2·3-dihydro-1H-indole-6-carboxylate had a mean particle size of 147 nm in the nanoparticle composition.

TABLE 17

| Reference Example | Compositional ratio (parts by weight) 4-[3-chloro-4-(cyclopropylcarbamoylamino)phenoxy]-7-methoxyquinoline-6-carboxamide/hydroxypropylcellulose (HPC)/polysorbate 80/benzalkonium chloride (BAC)/D-mannitol | Concentration (mg/mL) | Mean particle size (nm) |
|---|---|---|---|
| 9 | 1/0.5/0.1/0.001/0.1 | 2.39 | 228 |

TABLE 18

| Reference Example | Compositional ratio (parts by weight) methyl (3Z)-3-[({4-[N-methyl-2-(4-methylpiperazin-1-yl)acetamido]phenyl}amino)(phenyl)methylidene]-2-oxo-2-3-dihydro-1H-indole-6-carboxylate/hydroxypropylcellulose (HPC)/polysorbate 80/benzalkonium chloride (BAC)/D-mannitol | Concentration (mg/mL) | Mean particle size (nm) |
|---|---|---|---|
| 10 | 1/0.5/0.1/0.001/0.1 | 1.60 | 147 |

Example 105

(E)-N-[4-(3-Chloro-4-fluoroanilino)-7-methoxyquinazolin-6-yl]-4-piperidin-1-ylbut-2-enamide (RennoTech Co., Ltd.; the same holds true for the description below) was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (Zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to (E)-N-[4-(3-chloro-4-fluoroanilino)-7-methoxyquinazolin-6-yl]-4-piperidin-1-ylbut-2-enamide/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

As a result of measuring the concentration of this nanoparticle composition, (E)-N-[4-(3-chloro-4-fluoroanilino)-7-methoxyquinazolin-6-yl]-4-piperidin-1-ylbut-2-enamide had a concentration of 8.32 mg/mL.

As a result of assaying the nanoparticle composition using Zeta Sizer (Malvern instruments Nano series), (E)-N-[4-(3-chloro-4-fluoroanilino)-7-methoxyquinazolin-6-yl]-4-piperidin-1-ylbut-2-enamide had a mean particle size of 170 nm in the nanoparticle composition.

Example 106

The nanoparticle composition prepared in Example 105 was purified (17000 rpm, 5 min) using Micro Refrigerated Centrifuge (3740, Kubota Corp.) to adjust the concentration of (E)-N-[4-(3-chloro-4-fluoroanilino)-7-methoxyquinazolin-6-yl]-4-piperidin-1-ylbut-2-enamide to 6.10 mg/mL.

As a result of assaying the nanoparticle composition using Zeta Sizer (Malvern instruments Nano series), (E)-N-[4-(3-chloro-4-fluoroanilino)-7-methoxyquinazolin-6-yl]-4-piperidin-1-ylbut-2-enamide had a mean particle size of 152 nm in the nanoparticle composition.

Example 107

The nanoparticle composition prepared in Example 105 was purified (17000 rpm, 10 min) using Micro Refrigerated Centrifuge (3740, Kubota Corp.) to adjust the concentration of (E)-N-[4-(3-chloro-4-fluoroanilino)-7-methoxyquinazolin-6-yl]-4-piperidin-1-ylbut-2-enamide to 4.66 mg/mL.

As a result of assaying the nanoparticle composition using Zeta Sizer (Malvern instruments Nano series), (E)-N-[4-(3-chloro-4-fluoroanilino)-7-methoxyquinazolin-6-yl]-4-piperidin-1-ylbut-2-enamide had a mean particle size of 138 nm in the nanoparticle composition.

Example 108

The nanoparticle composition prepared in the same way as in Example 105 was purified (17000 rpm, 60 min) using Micro Refrigerated Centrifuge (3740, Kubota Corp.) to adjust the concentration of (E)-N-[4-(3-chloro-4-fluoroanilino)-7-methoxyquinazolin-6-yl]-4-piperidin-1-ylbut-2-enamide to 2.39 mg/mL.

As a result of assaying the nanoparticle composition using Zeta Sizer (Malvern instruments Nano series), (E)-N-[4-(3-chloro-4-fluoroanilino)-7-methoxyquinazolin-6-yl]-4-piperidin-1-ylbut-2-enamide had a mean particle size of 94 nm in the nanoparticle composition.

Example 109

The nanoparticle composition prepared in Example 105 was purified (17000 rpm, 30 min) using Micro Refrigerated Centrifuge (3740, Kubota Corp.) to adjust the concentration of (E)-N-[4-(3-chloro-4-fluoroanilino)-7-methoxyquinazolin-6-yl]-4-piperidin-1-ylbut-2-enamide to 1.35 mg/mL.

As a result of assaying the nanoparticle composition using Zeta Sizer (Malvern instruments Nano series), (E)-N-[4-(3-chloro-4-fluoroanilino)-7-methoxyquinazolin-6-yl]-4-piperidin-1-ylbut-2-enamide had a mean particle size of 93 nm in the nanoparticle composition.

TABLE 19

| Example | Compositional ratio (parts by weight) (E)-N-[4-(3-chloro-4-fluoroanilino)-7-methoxyquinazolin-6-yl]-4-piperidin-1-ylbut-2-enamide/hydroxypropylcellulose (HPC)/polysorbate 80/benzalkonium chloride (BAC)/D-mannitol | Concentration (mg/mL) | Mean particle size (nm) |
|---|---|---|---|
| 105 | 1/0.5/0.1/0.001/0.1 | 8.32 | 170 |
| 106 | 1/0.5/0.1/0.001/0.1 | 6.10 | 152 |
| 107 | 1/0.5/0.1/0.001/0.1 | 4.65 | 138 |
| 108 | 1/0.5/0.1/0.001/0.1 | 2.39 | 94 |
| 109 | 1/0.5/0.1/0.001/0.1 | 1.35 | 93 |

Example 110

N-[4-[[3-Chloro-4-[(3-fluorobenzyl)oxy]phenyl]amino]quinazolin-6-yl]acrylamide (Shanghai Lollane Biological Technology Co., Ltd.; the same holds true for the description below) was weighed into a zirconia container (Thinky Corp.) and subsequently prepared into a suspension by the addition of hydroxypropylcellulose (HPC), polysorbate 80, benzalkonium chloride (BAC), D-mannitol, and water, Zirconia balls (zirconia milling balls, YTZ, diameter: 0.1 mm, Nikkato Corp.) were placed in the container, which was then covered with the lid. Wet milling (mill/mix 2000 rpm, 1 min, loop/60 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-[4-[[3-chloro-4-[(3-fluorobenzyl)oxy]phenyl]amino]quinazolin-6-yl]acrylamide/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

As a result of measuring the concentration of this nanoparticle composition, N-[4-[[3-chloro-4-[(3-fluorobenzyl)oxy]phenyl]amino]quinazolin-6-yl]acrylamide had a concentration of 8.93 mg/mL.

As a result of assaying the nanoparticle composition using Zeta Sizer (Malvern instruments Nano series), N-[4-[[3-chloro-4-[(3-fluorobenzyl)oxy]phenyl]amino]quinazolin-6-yl]acrylamide had a mean particle size of 334 nm in the nanoparticle composition.

Example 111

The nanoparticle composition prepared in Example 110 was purified using Micro Refrigerated Centrifuge (3740, Kubota Corp.) to adjust the concentration of N-[4-[[3-chloro-4-[(3-fluorobenzyl)oxy]phenyl]amino]quinazolin-6-yl]acrylamide to 4.25 mg/mL.

As a result of assaying the nanoparticle composition using Zeta Sizer (Malvern instruments Nano series), N-[4-[[3-chloro-4-[(3-fluorobenzyl)oxy]phenyl]amino]quinazolin-6-yl]acrylamide had a mean particle size of 252 nm in the nanoparticle composition.

Example 112

The nanoparticle composition prepared in the same way as in Example 110 was purified using Micro Refrigerated Centrifuge (3740, Kubota Corp.) to adjust the concentration of N-[4-[[3-chloro-4-[(3-fluorobenzyl)oxy]phenyl]amino]quinazolin-6-yl]acrylamide to 2.45 mg/mL.

As a result of assaying the nanoparticle composition using Zeta Sizer (Malvern instruments Nano series), N-[4-[[3-chloro-4-[(3-fluorobenzyl)oxy]phenyl]amino]quinazolin-6-yl]acrylamide had a mean particle size of 204 nm in the nanoparticle composition.

Example 113

The nanoparticle composition prepared in Example 110 was purified using Micro Refrigerated Centrifuge (3740, Kubota Corp.) to adjust the concentration of N-[4-[[3-chloro-4-[(3-fluorobenzyl)oxy]phenyl]amino]quinazolin-6-yl]acrylamide to 1.40 mg/mL.

As a result of assaying the nanoparticle composition using Zeta Sizer (Malvern instruments Nano series), N-[4-[[3-chloro-4-[(3-fluorobenzyl)oxy]phenyl]amino]quinazolin-6-yl]acrylamide had a mean particle size of 185 nm in the nanoparticle composition.

TABLE 20

| Example | Compositional ratio (parts by weight) N-[4-[[3-chloro-4-[(3-fluorobenzyl)oxy]phenyl]amino]quinazolin-6-yl]acrylamide/hydroxypropylcellulose (HPC)/polysorbate 80/benzalkonium chloride (BAC)/D-mannitol | Concentration (mg/mL) | Mean particle size (nm) |
| --- | --- | --- | --- |
| 110 | 1/0.5/0.1/0.001/0.1 | 8.93 | 334 |
| 111 | 1/0.5/0.1/0.001/0.1 | 4.25 | 252 |
| 112 | 1/0.5/0.1/0.001/0.1 | 2.45 | 204 |
| 113 | 1/0.5/0.1/0.001/0.1 | 1.40 | 185 |

Example 114

1-N-[4-(6,7-Dimethoxyquinolin6-4-yl)oxyphenyl]-1-N'-(4-fluorophenyl)cyclopropane-1,1-dicarboxamide (Shanghai Lollane Biological Technology Co., Ltd.; the same holds true for the description below) was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 1-N-[4-(6,7-dimethoxyquinolin6-4-yl)oxyphenyl]-1-N'-(4-fluorophenyl)cyclopropane-1,1-dicarboxamide/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

As a result of measuring the concentration of this nanoparticle composition, 1-N-[4-(6,7-dimethoxyquinolin6-4-yl)oxyphenyl]-1-N'-(4-fluorophenyl)cyclopropane-1,1-dicarboxamide had a concentration of 10.77 mg/mL.

As a result of assaying the nanoparticle composition using Zeta Sizer (Malvern instruments Nano series), 1-N-[4-(6,7-dimethoxyquinolin6-4-yl)oxyphenyl]-1-N'-(4-fluorophe-

Example 115

The nanoparticle composition prepared in Example 114 was purified using Micro Refrigerated Centrifuge (3740, Kubota Corp.) to adjust the concentration of 1-N-[4-(6,7-dimethoxyquinolin6-4-yl)oxyphenyl]-1-N'-(4-fluorophenyl)cyclopropane-1,1-dicarboxamide to 2.00 mg/mL.

As a result of assaying the nanoparticle composition using Zeta Sizer (Malvern instruments Nano series), 1-N-[4-(6,7-dimethoxyquinolin6-4-yl)oxyphenyl]-1-N'-(4-fluorophenyl)cyclopropane-1,1-dicarboxamide had a mean particle size of 266 nm in the nanoparticle composition.

Example 116

1-N-[4-(6,7-Dimethoxyquinolin6-4-yl)oxyphenyl]-1-N'-(4-fluorophenyl)cyclopropane-1,1-dicarboxamide was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 1.0 mm, Nikkato Corp.) were placed in the container, which was then covered with the lid. Wet milling (mill/mix 2000 rpm, 1 min, loop/10 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 1-N-[4-(6,7-dimethoxyquinolin6-4-yl)oxyphenyl]-1-N'-(4-fluorophenyl)cyclopropane-1,1-dicarboxamide/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

As a result of measuring the concentration of this nanoparticle composition, 1-N-[4-(6,7-dimethoxyquinolin6-4-yl)oxyphenyl]-1-N'-(4-fluorophenyl)cyclopropane-1,1-dicarboxamide had a concentration of 9.62 mg/mL.

As a result of assaying Lime nanoparticle composition using Zeta Sizer (Malvern instruments Nano series), 1-N-[4-(6,7-dimethoxyquinolin6-4-yl)oxyphenyl]-1-N'-(4-fluorophenyl)cyclopropane-1,1-dicarboxamide had a mean particle size of 642 nm in the nanoparticle composition.

Example 117

The nanoparticle composition prepared in Example 116 was purified using Micro Refrigerated Centrifuge (3740, Kubota Corp.) to adjust the concentration of 1-N-[4-(6,7-dimethoxyquinolin6-4-yl)oxyphenyl]-1-N'-(4-fluorophenyl)cyclopropane-1,1-dicarboxamide to 0.97 mg/mL.

As a result of assaying the nanoparticle composition using Zeta Sizer (Malvern instruments Nano series), 1-N-[4-(6,7-dimethoxyquinolin6-4-yl)oxyphenyl]-1-N'-(4-fluorophenyl)cyclopropane-1,1-dicarboxamide had a mean particle size of 314 nm in the nanoparticle composition.

Example 118

1-N-[4-(6,7-Dimethoxyquinolin6-4-yl)oxyphenyl]-1-N'-(4-fluorophenyl)cyclopropane-1,1-dicarboxamide was weighed into a zirconia container (Thinky Corp.) and subsequently prepared into a suspension by the addition of hydroxypropylcellulose (hydroxypropylcellulose (HPC) and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 1-N-[4-(6,7-dimethoxyquinolin6-4-yl)oxyphenyl]-1-N'-(4-fluorophenyl)cyclopropane-1,1-dicarboxamide/hydroxypropylcellulose (HPC)=1 part by weight/0.3 parts by weight.

As a result of measuring the concentration of this nanoparticle composition, 1-N-[4-(6,7-dimethoxyquinolin6-4-yl)oxyphenyl]-1-N'-(4-fluorophenyl)cyclopropane-1,1-dicarboxamide had a concentration of 8.94 mg/mL.

As a result of assaying the nanoparticle composition using Zeta Sizer (Malvern instruments Nano series), 1-N-[4-(6,7-dimethoxyquinolin6-4-yl)oxyphenyl]-1-N'-(4-fluorophenyl)cyclopropane-1,1-dicarboxamide had a mean particle size of 271 nm in the nanoparticle composition.

Example 119

The nanoparticle composition prepared in Example 118 was purified using Micro Refrigerated Centrifuge (3740, Kubota Corp.) to adjust the concentration of 1-N-[4-(6,7-dimethoxyquinolin6-4-yl)oxyphenyl]-1-N'-(4-fluorophenyl)cyclopropane-1,1-dicarboxamide to 2.31 mg/mL.

As a result of assaying the nanoparticle composition using Zeta Sizer (Malvern instruments Nano series), 1-N-[4-(6,7-dimethoxyquinolin6-4-yl)oxyphenyl]-1-N'-(4-fluorophenyl)cyclopropane-1,1-dicarboxamide had a mean particle size of 338 nm in the nanoparticle composition.

Example 120

The nanoparticle composition prepared in Example 118 was purified using Micro Refrigerated Centrifuge (3740, Kubota Corp.) to adjust the concentration of 1-N-[4-(6,7-dimethoxyquinolin6-4-yl)oxyphenyl]-1-N'-(4-fluorophenyl)cyclopropane-1,1-dicarboxamide to 1.06 mg/mL.

As a result of assaying the nanoparticle composition using Zeta Sizer (Malvern instruments Nano series), 1-N-[4-(6,7-dimethoxyquinolin6-4-yl)oxyphenyl]-1-N'-(4-fluorophenyl)cyclopropane-1,1-dicarboxamide had a mean particle size of 326 nm in the nanoparticle composition.

Example 121

1-N-[4-(6,7-Dimethoxyquinolin6-4-yl)oxyphenyl]-1-N'-(4-fluorophenyl)cyclopropane-1,1-dicarboxamide was weighed into a zirconia container (Thinky Corp.) and subsequently prepared into a suspension by the addition of polysorbate 80 and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C., mill/mix 2000 rpm, 1 min, loop/30 times/−5° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 1-N-[4-(6,7-dimethoxyquinolin6-yl)oxyphenyl]-1-N'-(4-fluorophenyl)cyclopropane dicarboxamide/polysorbate 80=0.5 parts by weight/0.5 parts by weight.

As a result of measuring the concentration of this nanoparticle composition, 1-N-[4-(6,7-dimethoxyquinolin6-4-yl)oxyphenyl]-1-N'-(4-fluorophenyl)cyclopropane-1,1-dicarboxamide had a concentration of 4.97 mg/mL.

As a result of assaying the nanoparticle composition using Zeta Sizer (Malvern instruments Nano series), 1-N-[4-(6,7-dimethoxyquinolin6-yl)oxyphenyl]-1-N'-(4-fluorophenyl) cyclopropane-1,1-dicarboxamide had a mean particle size of 273 nm in the nanoparticle composition.

Example 122

1-N-[4-(6,7-Dimethoxyquinolin6-yl)oxyphenyl]-1-N'-(4-fluorophenyl)cyclopropane-1,1-dicarboxamide was weighed into a zirconia container (Thinky Corp.) and subsequently prepared into a suspension by the addition of polysorbate 80 and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). After addition of an aqueous polysorbate 80 solution, wet milling (mill/mix 2000 rpm, 1 min, loop/30 times/−5° C.) was performed. Then, the milled product was diluted (mill/mix 400 rpm, 5 min) by the addition, of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 1-N-[4-(6,7-dimethoxyquinolin6-4-yl)oxyphenyl]-1-N'-(4-fluorophenyl)cyclopropane-1,1-dicarboxamide/polysorbate 80=0.5 parts by weight/0.5 parts by weight.

As a result of measuring the concentration of this nanoparticle composition, 1-N-[4-(6,7-dimethoxyquinolin6-4-yl)oxyphenyl]-1-N'-(4-fluorophenyl)cyclopropane-1,1-dicarboxamide had a concentration of 5.11 mg/mL.

As a result of assaying the nanoparticle composition using Zeta Sizer (Malvern instruments Nano series), 1-N-[4-(6,7-dimethoxyquinolin6-yl)oxyphenyl]-1-N'-(4-fluorophenyl)cyclopropane-1,1-dicarboxamide had a mean particle size of 184 nm in the nanoparticle composition.

Example 123

The nanoparticle composition prepared in Example 122 was purified (17000 rpm, 1 min) using Micro Refrigerated Centrifuge (3740, Kubota Corp.) to adjust the concentration of 1-N-[4-(6,7-dimethoxyquinolin6-4-yl)oxyphenyl]-1-N'-(4-fluorophenyl)cyclopropane-1,1-dicarboxamide to 4.77 mg/mL.

As a result of assaying the nanoparticle composition using Zeta Sizer (Malvern instruments Nano series), 1-N-[4-(6,7-dimethoxyquinolin6-4-yl)oxyphenyl]-1-N'-(4-fluorophenyl)cyclopropane-1,1-dicarboxamide had a mean particle size of 187 nm in the nanoparticle composition.

Example 124

The nanoparticle composition prepared in Example 122 was purified (17000 rpm, 10 min) using Micro Refrigerated Centrifuge (3740, Kubota Corp.) to adjust the concentration of 1-N-[4-(6,7-dimethoxyquinolin6-4-yl)oxyphenyl]-1-N'-(4-fluorophenyl)cyclopropane-1,1-dicarboxamide to 2.21 mg/mL.

As a result of assaying the nanoparticle composition using Zeta Sizer (Malvern instruments Nano series), 1-N-[4-(6,7-dimethoxyquinolin6-4-yl)oxyphenyl]-1-N'-(4-fluorophenyl)cyclopropane-1,1-dicarboxamide had a mean particle size of 158 cm in the nanoparticle composition.

TABLE 21

| Example | Compositional ratio (parts by weight) 1-N-[4-(6,7-dimethoxyquinolin6-4-yl)oxyphenyl]-1-N'-(4-fluorophenyl)cyclopropane-1,1-dicarboxamide/ hydroxypropylcellulose (HPC)/polysorbate 80/ benzalkonium chloride (BAC)/D-mannitol | Concentration (mg/mL) | Mean particle size (nm) |
|---|---|---|---|
| 114 | 1/0.5/0.1/0.001/0.1 | 10.77 | 432 |
| 115 | 1/0.5/0.1/0.001/0.1 | 2.00 | 266 |
| 116 | 1/0.5/0.1/0.001/0.1 | 9.62 | 642 |
| 117 | 1/0.5/0.1/0.001/0.1 | 0.97 | 314 |
| 118 | 1/0.3/0/0/0 | 8.94 | 271 |
| 119 | 1/0.3/0/0/0 | 2.31 | 338 |
| 120 | 1/0.3/0/0/0 | 1.06 | 326 |
| 121 | 0.5/0/0.5/0/0 | 4.97 | 273 |
| 122 | 0.5/0/0.5/0/0 | 5.11 | 184 |
| 123 | 0.5/0/0.5/0/0 | 4.77 | 187 |
| 124 | 0.5/0/0.5/0/0 | 2.21 | 158 |

Example 125

6-(6,7-Dimethoxyquinazolin-4-yl)oxy-N,2-dimethyl-1-benzofuran-3-carboxamide (Shanghai Lollane Biological Technology Co., Ltd.; the same holds true for the description below) was weighed into a zirconia container (Thinky Corp.) and subsequently prepared into a suspension by the addition of polysorbate 80 and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 6-(6,7-dimethoxyquinazolin-4-yl)oxy-N,2-dimethyl-1-benzofuran-3-carboxamide/polysorbate 80=0.5 parts by weight/0.5 parts by weight.

As a result of measuring the concentration of this nanoparticle composition, 6-(6,7-dimethoxyquinazolin-4-yl)oxy-N,2-dimethyl-1-benzofuran-3-carboxamide had a concentration of 0.48 mg/mL.

As a result of assaying the nanoparticle composition using Zeta Sizer (Malvern instruments Nano series), 6-(6,7-dimethoxyquinazolin-4-yl)oxy-N,2-dimethyl-1-benzofuran-3-carboxamide had a mean particle size of 264 nm in the nanoparticle composition.

Example 126

6-(6,7-Dimethoxyquinazolin-4-yl)oxy-N,2-dimethyl-1-benzofuran-3-carboxamide was weighed into a zirconia container (Thinky Corp.) and subsequently prepared into a suspension by the addition of polysorbate 80 and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 6-(6,7-dimethoxyquinazolin-4-yl)oxy-N,2-dimethyl-1-benzofuran-3-carboxamide/polysorbate 80=0.5 parts by weight/0.25 parts by weight.

As a result of measuring the concentration of this nanoparticle composition, 6-(6,7-dimethoxyquinazolin-4-yl)oxy-N,2-dimethyl-1-benzofuran-3-carboxamide had a concentration of 0.44 mg/mL.

As a result of assaying the nanoparticle composition using Zeta Sizer (Malvern instruments Nano series), 6-(6,7-dimethoxyquinazolin-4-yl)oxy-N,2-dimethyl-1-benzofuran-3-carboxamide had a mean particle size of 174 nm in the nanoparticle composition.

Example 127

6-(6,7-Dimethoxyquinazolin-4-yl)oxy-N,2-dimethyl-1-benzofuran-3-carboxamide was weighed into a zirconia container (Thinky Corp.) and subsequently prepared into a suspension by the addition of polysorbate 80 and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/60 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 6-(6,7-dimethoxyquinazolin-4-yl)oxy-N,2-dimethyl-1-benzofuran-3-carboxamide/polysorbate 80=0.5 parts by weight/0.25 parts by weight.

As a result of measuring the concentration of this nanoparticle composition, 6-(6,7-dimethoxyquinazolin-4-yl)oxy-N,2-dimethyl-1-benzofuran-3-carboxamide had a concentration of 5.22 mg/mL.

As a result of assaying the nanoparticle composition using Zeta Sizer (Malvern instruments Nano series), 6-(6,7-dimethoxyquinazolin-4-yl)oxy-N,2-dimethyl-1-benzofuran-3-carboxamide had a mean particle size of 281 nm in the nanoparticle composition.

Example 128

The nanoparticle composition prepared in Example 127 was purified using Micro Refrigerated Centrifuge (3740, Kubota Corp.) to adjust the concentration of 6-(6,7-dimethoxyquinazolin-4-yl)oxy-N,2-dimethyl-1-benzofuran-3-carboxamide to 1.18 mg/mL.

As a result of assaying the nanoparticle composition using Zeta Sizer (Malvern instruments Nano series), 6-(6,7-dimethoxyquinazolin-4-yl)oxy-N,2-dimethyl-1-benzofuran-3-carboxamide had a mean particle size of 218 nm in the nanoparticle composition.

TABLE 22

| Example | Compositional ratio (parts by weight) 6-(6,7-dimethoxyquinazolin-4-yl)oxy-N,2-dimethyl-1-benzofuran-3-carboxamide/polysorbate 80 | Concentration (mg/mL) | Mean particle size (nm) |
| --- | --- | --- | --- |
| 125 | 0.5/0.5 | 0.48 | 264 |
| 126 | 0.5/0.25 | 0.44 | 174 |
| 127 | 0.5/0.25 | 5.22 | 281 |
| 128 | 0.5/0.25 | 1.18 | 218 |

Example 129

N-(3-Ethynylphenyl)-7,8,10,11,13,14-hexahydro-[1,4,7,10]tetraoxacyclododecino[2,3-g]quinazolin-4-amine (Shanghai Lollane Biological Technology Co., Ltd.; the same holds true for the description below) was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-(3-ethynylphenyl)-7,8,10,11,13,14-hexahydro-[1,4,7,10]tetraoxacyclododecino[2,3-g]quinazolin-4-amine/hydroxypropylcellulose (HPC)/polysorbate 80/benzalkonium chloride (BAC)/D-mannitol=0.5 parts by weight/1 part by weight/0.2 parts by weight/0.002 parts by weight/0.2 parts by weight.

As a result of measuring the concentration of this nanoparticle composition, N-(3-ethynylphenyl)-7,8,10,11,13,14-hexahydro-[1,4,7,10]tetraoxacyclododecino[2,3-g]quinazolin-4-amine had a concentration of 5.32 mg/mL.

As a result of assaying the nanoparticle composition using Zeta Sizer (Malvern instruments Nano series), N-(3-ethynylphenyl)-7,8,10,11,13,14-hexahydro-[1,4,7,10]tetraoxacyclododecino[2,3-g]quinazolin-4-amine had a mean particle size of 197 nm in the nanoparticle composition.

Example 130

The nanoparticle composition prepared in Example 129 was purified using Micro Refrigerated Centrifuge (3740, Kubota Corp.) to adjust the concentration of N-(3-ethynylphenyl)-7,8,10,11,13,14-hexahydro-[1,4,7,10]tetraoxacyclododecino[2,3-g]quinazolin-4-amine to 2.20 mg/mL.

As a result of assaying the nanoparticle composition using Zeta Sizer (Malvern instruments Nano series), N-(3-ethynylphenyl)-7,8,10,11,13,14-hexahydro-[1,4,7,10]tetraoxacyclododecino[2,3-g]quinazolin-4-amine had a mean particle size of 196 nm in the nanoparticle composition.

Example 131

N-(3-Ethynylphenyl)-7,8,10,11,13,14-hexahydro-[1,4,7,10]tetraoxacyclododecino[2,3-g]quinazolin-4-amine was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 nm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-(3-ethynylphenyl)-7,8,10,11,13,14-hexahydro-[1,4,7,10]tetraoxacyclododecino[2,3-g]quinazolin-4-amine/hydroxypropylcellulose (HPC)/polysorbate 80/benzalkonium chloride (BAC)/D-mannitol=0.25 parts by weight/0.5 parts by weight/0.1 parts by weight/0.001 parts by weight/0.1 parts by weight.

As a result of measuring the concentration of this nanoparticle composition, N-(3-ethynylphenyl)-7,8,10,11,13,14-hexahydro-[1,4,7,10]tetraoxacyclododecino[2,5-g]quinazolin-4-amine had a concentration of 2.66 mg/mL.

As a result of assaying the nanoparticle composition using Zeta Sizer (Malvern instruments Nano series), N-(3-ethynylphenyl)-7,8,10,11,13,14-hexahydro-[1,4,7,10]tetraoxacyclododecino[2,3-g]quinazolin-4-amine had a mean particle size of 196 nm in the nanoparticle composition.

TABLE 23

| Example | Compositional ratio (parts by weight) N-(3-ethynylphenyl)-7,8,10,11,13,14-hexahydro-[1,4,7,10]tetraoxacyclododecino[2,3-g]quinazolin-4-amine/hydroxypropylcellulose (HPC)/polysorbate 80/benzalkonium chloride (BAC)/D-mannitol | Concentration (mg/mL) | Mean particle size (nm) |
|---|---|---|---|
| 129 | 0.5/1/0.2/0.002/0.2 | 5.32 | 197 |
| 130 | 0.5/1/0.2/0.002/0.2 | 2.20 | 179 |
| 131 | 0.25/0.5/0.1/0.001/0.1 | 2.66 | 196 |

Example 132

3-(2-Imidazo[1,2-b]pyridazin-3-ylethynyl)-4-methyl-N-[4-[(4-methylpiperazin-1-yl)methyl]-3-(trifluoromethyl)phenyl]benzamide (PharmaBlock Sciences (Nanjing), Inc.; the same holds true for the description below) was weighed into a zirconia container (Thinky Corp.) and subsequently prepared into a suspension by the addition of hydroxypropylcellulose (HPC) and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 3-(2-imidazo[1,2-b]pyridazin-3-ylethynyl)-4-methyl-N-[4-[(4-methylpiperazin-1-yl)methyl]-3-(trifluoromethyl)phenyl]benzamide/hydroxypropylcellulose (HPC)=1 part by weight/0.3 parts by weight.

This nanoparticle composition was purified (17000 rpm, 19 min) using Micro Refrigerated Centrifuge (3740, Kubota Corp.) to adjust the concentration of 3-(2-imidazo[1,2-b]pyridazin-3-ylethynyl)-4-methyl-N-[4-[(4-methylpiperazin-1-yl)methyl]-3-(trifluoromethyl)phenyl]benzamide to 2.43 mg/mL.

As a result of assaying the nanoparticle composition using Zeta Sizer (Malvern instruments Nano series), 3-(2-imidazo[1,2-b]pyridazin-3-ylethynyl)-4-methyl-N-[4-[(4-methylpiperazin-1-yl)methyl]-3-(trifluoromethyl)phenyl]benzamide had a mean particle size of 194 nm in the nanoparticle composition.

TABLE 24

| Example | Compositional ratio (parts by weight) 3-(2-imidazo[1,2-b]pyridazin-3-ylethynyl-4-methyl-N-[4-[(4-methylpiperazin-1-yl)methyl]-3-(trifluoromethyl)phenyl]benzamide/ hydroxypropylcellulose (HPC)/polysorbate 80/ benzalkonium chloride (BAC)/D-mannitol | Concentration (mg/ml) | Mean particle size (nm) |
|---|---|---|---|
| 132 | 1/0.3/0/0/0 | 2.43 | 194 |

Example 133

N-Methyl-2-[[3-[(E)-2-pyridin-2-ylethenyl]-1H-indazol-6-yl]sulfanyl]benzamide (Sun-Shine Chemical Technology Co., Ltd.; the same holds true for the description below) was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-methyl-2-[[3-[(E)-2-pyridin-2-ylethenyl]-1H-indazol-6-yl]sulfanyl]benzamide/hydroxypropylcellulose (HPC)/polysorbate 80/benzalkonium chloride (BAC)/D-mannitol=1.0 part by weight/0.5 parts by weight/0.1 parts by weight/0.001 parts by weight/0.1 parts by weight.

As a result of measuring the concentration of this nanoparticle composition, N-methyl-2-[[3-[(E)-2-pyridin-2-ylethenyl]-1H-indazol-6-yl]sulfanyl]benzamide had a concentration of 9.46 mg/mL.

As a result of assaying the nanoparticle composition using Zeta Sizer (Malvern instruments Nano series), N-methyl-2-[[3-[(E)-2-pyridin-2-ylethenyl]-1H-indazol-6-yl]sulfanyl]benzamide had a mean particle size of 127 nm in the nanoparticle composition.

Example 134

The nanoparticle composition prepared in Example 133 was purified using Micro Refrigerated Centrifuge (3740, Kubota Corp.) to adjust the concentration of N-methyl-2-[[3-[(E)-2-pyridin-2-ylethenyl]-1H-indazol-6-yl]sulfanyl]benzamide to 1.84 mg/mL.

As a result of assaying the nanoparticle composition using Zeta Sizer (Malvern instruments Nano series), N-methyl-2-[[3-[(E)-2-pyridin-2-ylethenyl]-1H-indazol-6-yl]sulfanyl]benzamide had a mean particle size of 125 nm in the nanoparticle composition.

Example 135

N-Methyl-2-[[3-[(E)-2-pyridin-2-ylethenyl]-1H-indazol-6-yl]sulfanyl]benzamide was weighed into a zirconia container (Thinky Corp.) and subsequently prepared into a suspension by the addition of hydroxypropylcellulose (HPC and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-methyl-2-[[3-[(E)-2-pyridin-2-ylethenyl]-1H-indazol-6-yl]sulfanyl]benzamide/hydroxypropylcellulose (HPC)=1 part by weight/0.3 parts by weight.

As a result of measuring the concentration of this nanoparticle composition, N-methyl-2-[[3-[(E)-2-pyridin-2-ylethenyl]-1H-indazol-6-yl]sulfanyl]benzamide had a concentration of 9.23 mg/mL.

As a result of assaying the nanoparticle composition using Zeta Sizer (Malvern instruments Nano series), N-methyl-2-[[3-[(E)-2-pyridin-2-ylethenyl]-1H-indazol-6-yl]sulfanyl]benzamide had a mean particle size of 159 nm in the nanoparticle composition.

Example 136

The nanoparticle composition prepared in Example 134 was purified using Micro Refrigerated Centrifuge (3740, Kubota Corp.) to adjust the concentration of N-methyl-2-[[3-[(E)-2-pyridin-2-ylethenyl]-1H-indazol-6-yl]sulfanyl]benzamide to 2.42 mg/mL.

As a result of assaying the nanoparticle composition using Zeta Sizer (Malvern instruments Nano series), N-methyl-2-[[3-[(E)-2-pyridin-2-ylethenyl]-1H-indazol-6-yl]sulfanyl]benzamide had a mean particle size of 84 nm in the nanoparticle composition.

TABLE 25

| Example | Compositional ratio (parts by weight) N-methyl-2-[[3-[(E)-2-pyridin-2-ylethenyl]-1H-indazol-6-yl]sulfanyl]benzamide/ hydroxypropylcellulose (HPC)/polysorbate 80/ benzalkonium chloride (BAC)/D-mannitol | Concentration (mg/mL) | Mean particle size (nm) |
|---|---|---|---|
| 133 | 1/0.5/0.1/0.001/0.1 | 9.46 | 127 |
| 134 | 1/0.5/0.1/0.001/0.1 | 1.84 | 125 |

TABLE 25-continued

| Example | Compositional ratio (parts by weight) N-methyl-2-[[3-[(E)-2-pyridin-2-ylethenyl]-1H-indazol-6-yl]sulfanyl]benzamide/ hydroxypropylcellulose (HPC)/polysorbate 80/ benzalkonium chloride (BAC)/D-mannitol | Concentration (mg/mL) | Mean particle size (nm) |
|---|---|---|---|
| 135 | 1/0.3/0/0/0 | 9.23 | 159 |
| 136 | 1/0.3/0/0/0 | 2.42 | 84 |

Example 137

A nanoparticle composition having composition of N-methyl-2-[[3-[(E)-2-pyridin-2-ylethenyl]-1H-indazol-6-yl]sulfanyl]benzamide/hydroxypropylmethylcellulose (HPMC)/polysorbate 80/benzalkonium chloride (BAC)/D-mannitol=1 part by weight/0.5 parts by weight/0.1 parts by weight/0.001 parts by weight/0.1 parts by weight and having N-methyl-2-[[3-[(E)-2-pyridin-2-ylethenyl]-1H-indazol-6-yl]sulfanyl]benzamide with a concentration of 1.44 mg/mL and a mean particle size of 225 nm was obtained from N-methyl-2-[[3-[(E)-2-pyridin-2-ylethenyl]-1H-indazol-6-yl]sulfanyl]benzamide, hydroxypropylmethylcellulose (HPMC), polysorbate 80, benzalkonium chloride (BAC), D-mannitol, and an aqueous glucose solution in accordance with Example 133 except that the thickening agent was changed from hydroxypropylcellulose (HPC) to hydroxypropylmethylcellulose (HPMC).

Example 138

A nanoparticle composition having composition of N-methyl-2-[[3-[(E)-2-pyridin-2-ylethenyl]-1H-indazol-6-yl]sulfanyl]benzamide/polyvinyl alcohol (PVA)/polysorbate 80/benzalkonium chloride (BAC)/D-mannitol=1 part by weight/0.5 parts by weight/0.1 parts by weight/0.001 parts by weight/0.1 parts by weight and having N-methyl-2-[[3-[(E)-2-pyridin-2-ylethenyl]-1H-indazol-6-yl]sulfanyl]benzamide with a concentration of 2.19 mg/mL and a mean particle size of 166 nm was obtained from N-methyl-2-[[3-[(E)-2-pyridin-2-ylethenyl]-1H-indazol-6-yl]sulfanyl]benzamide, polyvinyl alcohol (PVA), polysorbate 80, benzalkonium chloride (BAC), D-mannitol, and an aqueous glucose solution in accordance with Example 133 except that the thickening agent was changed from hydroxypropylcellulose (HPC) to polyvinyl alcohol (PVA).

Example 139

A nanoparticle composition having composition of N-methyl-2-[[3-[(E)-2-pyridin-2-ylethenyl]-1H-indazol-6-yl]sulfanyl]benzamide/Pluronic(Registered Trademark) F-127/polysorbate 80/benzalkonium chloride (BAC)/D-mannitol=1 part by weight/0.5 parts by weight/0.1 parts by weight/0.001 parts by weight/0.1 parts by weight and having N-methyl-2-[[3-[(E)-2-pyridin-2-ylethenyl]-1H-indazol-6-yl]sulfanyl]benzamide with a concentration of 3.94 mg/mL and a mean particle size of 111 nm was obtained from N-methyl-2-[[3-[(E)-2-pyridin-2-ylethenyl]-1H-indazol-6-yl]sulfanyl]benzamide, Pluronic(Registered Trademark) F-127, polysorbate 80, benzalkonium chloride (BAC), D-mannitol, and an aqueous glucose solution in accordance with Example 133 except that the thickening agent was changed from hydroxypropylcellulose (HPC) to Pluronic (Registered Trademark) F-127.

TABLE 26

| Example | Compositional ratio (parts by weight) N-methyl-2[[3-[(E)-2-pyridin-2-ylethenyl]-1H-indazol-6-yl]sulfanyl]benzamide/X/polysorbate 80/benzalkonium chloride (BAC)/D-mannitol | X | Concentration (mg/mL) | Mean particle size (nm) |
|---|---|---|---|---|
| 137 | 1/0.5/0.1/0.001/0.1 | HPMC | 1.44 | 225 |
| 138 | 1/0.5/0.1/0.001/0.1 | PVA | 2.19 | 166 |
| 139 | 1/0.5/0.1/0.001/0.1 | Pluronic F127 | 3.94 | 111 |

Example 140

A nanoparticle composition having composition of N-methyl-2-[[3-[(E)-2-pyridin-2-ylethenyl]-1H-indazol-6-yl]sulfanyl]benzamide/hydroxypropylcellulose (HPC)/Solutol(Registered Trademark) HS15/benzalkonium chloride (BAC)/D-mannitol=1 part by weight/0.5 parts by weight/0.1 parts by weight/0.001 parts by weight/0.1 parts by weight and having N-methyl-2-[[3-[(E)-2-pyridin-2-ylethenyl]-1H-indazol-6-yl]sulfanyl]benzamide with a concentration of 0.85 mg/mL and a mean particle size of 129 nm was obtained from N-methyl-2-[[3-[(E)-2-pyridin-2-ylethenyl]-1H-indazol-6-yl]sulfanyl]benzamide, hydroxypropylcellulose (HPC), Solutol(Registered Trademark) HS15, benzalkonium chloride (BAC), D-mannitol, and an aqueous glucose solution in accordance with Example 133 except that the surfactant was changed from polysorbate 80 to Solutol(Registered Trademark) HS15.

Example 141

A nanoparticle composition having composition of N-methyl-2-[[3-[(E)-2-pyridin-2-ylethenyl]-1H-indazol-6-yl]sulfanyl]benzamide/hydroxypropylcellulose (HPC)/tyloxapol/benzalkonium chloride (BAC)/D-mannitol=1 part by weight/0.5 parts by weight/0.1 parts by weight/0.001 parts by weight/0.1 parts by weight and having N-methyl-2-[[3-[(E)-2-pyridin-2-ylethenyl]-1H-indazol-6-yl]sulfanyl]benzamide with a concentration of 1.17 mg/mL and a mean particle size of 128 nm was obtained from N-methyl-2-[[3-[(E)-2-pyridin-2-ylethenyl]-1H-indazol-6-yl]sulfanyl]benzamide, hydroxypropylcellulose (HPC), tyloxapol, benzalkonium chloride (BAC), D-mannitol, and an aqueous glucose solution in accordance with Example 133 except that the surfactant was changed from polysorbate 80 to tyloxapol.

Example 142

A nanoparticle composition having composition of N-methyl-2-[[3-[(E)-2-pyridin-2-ylethenyl]-1H-indazol-6-yl]sulfanyl]benzamide/hydroxypropylcellulose (HPC)/Cremophor(Registered Trademark) EL/benzalkonium chloride (BAC)/D-mannitol=1 part by weight/0.5 parts by weight/0.1 parts by weight/0.001 parts by weight/0.1 parts by weight and having N-methyl-2-[[3-[(E)-2-pyridin-2-ylethenyl]-1H-indazol-6-yl]sulfanyl]benzamide with a concentration of 1.03 mg/mL and a mean particle size of 127 nm was obtained from N-methyl-2-[[3-[(E)-2-pyridin-2-ylethenyl]-1H-indazol-6-yl]sulfanyl]benzamide, hydroxypropylcellulose (HPC), Cremophor(Registered Trademark) EL, benzalkonium chloride (BAC), D-mannitol, and an aqueous glucose solution in accordance with Example 133 except that the surfactant was changed from polysorbate 80 to Cremophor(Registered Trademark) EL.

Example 143

A nanoparticle composition having composition of N-methyl-2-[[3-[(E)-2-pyridin-2-ylethenyl]-1H-indazol-6-yl]sulfanyl]benzamide/hydroxypropylcellulose (HPC)/n-octyl-β-D-glucoside/benzalkonium chloride (BAC)/D-mannitol=1 part by weight/0.5 parts by weight/0.1 parts by weight/0.001 parts by weight/0.1 parts by weight and having N-methyl-2-[[3-[(E)-2-pyridin-2-ylethenyl]-1H-indazol-6-yl]sulfanyl]benzamide with a concentration of 0.90 mg/mL and a mean particle size of 131 nm was obtained from N-methyl-2-[[3-[(E)-2-pyridin-2-ylethenyl]-1H-indazol-6-yl]sulfanyl]benzamide, hydroxypropylcellulose (HPC), n-octyl-β-D-glucoside, benzalkonium chloride (BAC), D-mannitol, and an aqueous glucose solution in accordance with Example 133 except that the surfactant was changed from polysorbate 80 to n-octyl-β-D-glucoside.

Example 144

A nanoparticle composition having composition of N-methyl-2-[[3-[(E)-2-pyridin-2-ylethenyl]-1H-indazol-6-yl]sulfanyl]benzamide/hydroxypropylcellulose (HPC)/sodium lauryl sulfate/benzalkonium chloride (BAC)/D-mannitol=1 part by weight/0.5 parts by weight/0.1 parts by weight/0.001 parts by weight/0.1 parts by weight and having N-methyl-2-[[3-[(E)-2-pyridin-2-ylethenyl]-1H-indazol-6-yl]sulfanyl]benzamide with a concentration of 3.24 mg/mL and a mean particle size of 116 nm was obtained from N-methyl-2-[[3-[(E)-2-pyridin-2-ylethenyl]-1H-indazol-6-yl]sulfanyl]benzamide, hydroxypropylcellulose (HPC), sodium lauryl sulfate, benzalkonium chloride (BAC), D-mannitol, and an aqueous glucose solution in accordance with Example 133 except that the surfactant was changed from polysorbate 80 to sodium lauryl sulfate.

TABLE 27

| Example | Compositional ratio (parts by weight) N-methyl-2[[3-[(E)-2-pyridin-2-ylethenyl]-1H-indazol-6-yl]sulfanyl]benzamide/ Hydroxypropylcellulose (HPC)/X/benzalkonium chloride (BAC)/D-mannitol | X | Concentration (mg/mL) | Mean particle size (nm) |
|---|---|---|---|---|
| 140 | 1/0.5/0.1/0.001/0.1 | Solutol HS15 | 0.85 | 129 |
| 141 | 1/0.5/0.1/0.001/0.1 | Tyloxapol | 1.17 | 128 |
| 142 | 1/0.5/0.1/0.001/0.1 | Cremophor EL | 1.03 | 127 |
| 143 | 1/0.5/0.1/0.001/0.1 | n-Octyl-β-D-glucoside | 0.90 | 131 |
| 144 | 1/0.5/0.1/0.001/0.1 | Sodium lauryl sulfate | 3.24 | 115 |

Example 145

N-(3-Ethynylphenyl)-6,7-bis(2-methoxyethoxy)quinazolin-4-amine hydrochloride (LC Laboratories, Inc; the same holds true for the description below) was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-(3-ethynylphenyl)-6,7-bis(2-methoxyethoxy)quinazolin-4-amine hydrochloride/hydroxypropylcellulose (HPC)/polysorbate 80/benzalkonium chloride (BAC)/D-mannitol=1 part by weight/0.125 parts by weight/0.025 parts by weight/0.00025 parts by weight/0.025 parts by weight.

As a result of measuring the concentration of this nanoparticle composition, N-(3-ethynylphenyl)-6,7-bis(2-methoxyethoxy)quinazolin-4-amine hydrochloride had a concentration of 10.10 mg/mL.

As a result of assaying the nanoparticle composition using Zeta Sizer (Malvern instruments Nano series), N-(3-ethynylphenyl)-6,7-bis(2-methoxyethoxy)quinazolin-4-amine hydrochloride had a mean particle size of 109 nm in the nanoparticle composition.

TABLE 28

| Example | Compositional ratio (parts by weight) N-(3-ethynylphenyl)-6,7-bis(2-methoxyethoxy) quinazolin-4-amine hydrochloride/ hydroxypropylcellulose (HPC)/polysorbate 80/benzalkonium chloride (BAC)/D-mannitol | Concentration (mg/mL) | Mean particle size (nm) |
|---|---|---|---|
| 145 | 1/0.125/0.025/0.00025/0.025 | 10.10 | 109 |

Example 146

A nanoparticle composition having composition of N-(3-ethynylphenyl)-6,7-bis(2-methoxyethoxy)quinazolin-4-amine hydrochloride/hydroxypropylcellulose (HPC)/sodium lauryl sulfate=1 part by weight/0.125 parts by weight/0.01 parts by weight and having N-(3-ethynylphenyl)-6,7-bis(2-methoxyethoxy)quinazolin-4-amine hydrochloride with a concentration of 10.23 mg/mL and a mean particle size of 111 nm was obtained from N-(3-ethynylphenyl)-6,7-bis(2-methoxyethoxy)quinazolin-4-amine hydrochloride, hydroxypropylcellulose (HPC), sodium lauryl sulfate, and an aqueous glucose solution in accordance with Example 145 except that the surfactant was changed from polysorbate 80 to sodium lauryl sulfate, and benzalkonium chloride (BAC) and D-mannitol were excluded from the composition.

Example 147

A nanoparticle composition having composition of N-(3-ethynylphenyl)-6,7-bis(2-methoxyethoxy)quinazolin-4-amine hydrochloride/hydroxypropylcellulose (HPC)/sodium lauryl sulfate=1 part by weight/0.125 parts by weight/0.001 parts by weight and having N-(3-ethynylphenyl)-6,7-bis(2-methoxyethoxy)quinazolin-4-amine hydrochloride with a concentration of 9.87 mg/mL and a mean particle size of 114 nm was obtained from N-(3-ethynylphenyl)-6,7-bis(2-methoxyethoxy)quinazolin-4-amine hydrochloride, hydroxypropylcellulose (HPC), sodium lauryl sulfate, and an aqueous glucose solution in accordance with Example 145 except that the surfactant was changed from polysorbate 80 to sodium lauryl sulfate, and benzalkonium chloride (BAC) and D-mannitol were excluded from the composition.

TABLE 29

| Example | Compositional ratio (parts by weight) N-(3-ethynylphenyl)-6,7-bis(2-methoxyethoxy)quinazolin-4-amine hydrochloride/ hydroxypropylcellulose (HPC)/sodium lauryl sulfate | Concentration (mg/mL) | Mean particle size (nm) |
|---|---|---|---|
| 146 | 1/0.125/0.01 | 10.23 | 111 |
| 147 | 1/0.125/0.001 | 9.87 | 114 |

Example 148

A nanoparticle composition having composition of N-(3-ethynylphenyl)-6,7-bis(2-methoxyethoxy)quinazolin-4-amine/carboxymethylcellulose (CMC Na)/polysorbate 80=1 part by weight/0.05 parts by weight/0.001 parts by weight and having N-(3-ethynylphenyl)-6,7-bis(2-methoxyethoxy)quinazolin-4-amine with a concentration of 8.18 mg/mL and a mean particle size of 205 nm was obtained from N-(3-ethynylphenyl)-6,7-bis(2-methoxyethoxy)quinazolin-4-amine, carboxymethylcellulose (CMC Na), polysorbate 80, and an aqueous glucose solution in accordance with Example 145 except that: N-(3-ethynylphenyl)-6,7-bis(2-methoxyethoxy)quinazolin-4-amine hydrochloride was changed to N-(3-ethynylphenyl)-6,7-bis(2-methoxyethoxy)quinazolin-4-amine (Combi-Blocks, Inc.; the same holds true for the description below); the thickening agent was changed from hydroxypropylcellulose (HPC) to carboxymethylcellulose (CMC Na); the amount of polysorbate 80 was changed from 0.025 parts by weight to 0.001 parts by weight; and benzalkonium chloride (BAC) and D-mannitol were excluded from the composition.

TABLE 30

| Example | Compositional ratio (parts by weight) N-(3-ethynylphenyl)-6,7-bis(2-methoxyethoxy)quinazolin-4-amine/ carboxymethylcellulose sodium (CMC Na)/ polysorbate 80 | Concentration (mg/mL) | Mean particle size (nm) |
|---|---|---|---|
| 148 | 1/0.05/0.001 | 8.18 | 205 |

Example 149

A nanoparticle composition having composition of N-(3-ethynylphenyl)-6,7-bis(2-methoxyethoxy)quinazolin-4-amine hydrochloride/carboxymethylcellulose (CMC Na)/polysorbate 80=1 part by weight/0.05 parts by weight/0.125 parts by weight and having N-(3-ethynylphenyl)-6,7-bis(2-methoxyethoxy)quinazolin-4-amine hydrochloride with a concentration of 6.76 mg/mL and a mean particle size of 258 nm was obtained from N-(3-ethynylphenyl)-6,7-bis(2- methoxyethoxy)quinazolin-4-amine hydrochloride, carboxymethylcellulose (CMC Na), polysorbate 80, and an aqueous glucose solution in accordance with Example 145 except that: N-(3-ethynylphenyl)-6,7-bis(2-methoxyethoxy) quinazolin-4-amine hydrochloride was changed to N-(3-ethynylphenyl)-6,7-bis(2-methoxyethoxy)quinazolin-4-amine; the thickening agent was changed from hydroxypropylcellulose (HPC) to carboxymethylcellulose (CMC Na); the amount of polysorbate 80 was changed from 0.025 parts by weight to 0.125 parts by weight; and benzalkonium chloride (BAC) and D-mannitol were excluded from the composition.

TABLE 31

| Example | Compositional ratio (parts by weight) N-(3-ethynylphenyl)-6,7-bis(2-methoxyethoxy)quinazolin-4-amine/ carboxymethylcellulose sodium (CMC Na)/ hydroxypropylcellulose (HPC) | Concentration (mg/mL) | Mean particle size (nm) |
|---|---|---|---|
| 149 | 1/0.05/0.125 | 6.76 | 258 |

Example 150

A nanoparticle composition having composition of N-(3-ethynylphenyl)-6,7-bis(2-methoxyethoxy)quinazolin-4-amine/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having N-(3-ethynylphenyl)-6,7-bis (2-methoxyethoxy)quinazolin-4-amine with a concentration of 9.33 mg/mL and a mean particle size of 114 nm was obtained from N-(3-ethynylphenyl)-6,7-bis(2-methoxyethoxy)quinazolin-4-amine, hydroxypropylcellulose (HPC), polysorbate 80, benzalkonium chloride (BAC), D-mannitol, and an aqueous glucose solution in accordance with Example 145 except that: N-(3-ethynylphenyl)-6,7-bis(2-methoxyethoxy)quinazolin-4-amine hydrochloride was changed to N-(3-ethynylphenyl)-6,7-bis(2-methoxyethoxy)quinazolin-4-amine; the amount of hydroxypropylcellulose (HPC) was changed from 0.125 parts by weight to 0.5 parts by weight; the amount of polysorbate 80 was changed from 0,025 parts by weight to 0.1 parts by weight; the amount of benzalkonium chloride (BAC) was changed from 0.00025 parts by weight to 0.001 parts by weight; and the amount of D-mannitol was changed from 0.025 parts by weight to 0.1 parts by weight.

Example 151

A nanoparticle composition having composition of N-(3-ethynylphenyl)-6,7-bis(2-methoxyethoxy)quinazolin-4-amine/hydroxypropylcellulose (HPC)/polysorbate 80/benzalkonium chloride (BAC)/D-mannitol=1 part by weight/ 0.125 parts by weight/0.025 parts by weight/0.00025 parts by weight/0.025 parts by weight and having N-(3-ethynylphenyl)-6,7-bis(2-methoxyethoxy)quinazolin-4-amine with a concentration of 10.34 mg/mL and a mean particle size of 76 nm was obtained from N-(3-ethynylphenyl)-6,7-bis(2-methoxyethoxy)quinazolin-4-amine, hydroxypropylcellulose (HPC), polysorbate 80, benzalkonium chloride (BAC), D-mannitol, and an aqueous glucose solution in accordance with Example 145 except that N-(3-ethynylphenyl)-6,7-bis(2-methoxyethoxy)quinazolin-4-amine hydrochloride was changed to N-(3-ethynylphenyl)-6,7-bis(2-methoxyethoxy)quinazolin-4-amine.

TABLE 32

| Example | Compositional ratio (parts by weight) N-(3-ethynylphenyl)-6,7-bis(2-methoxyethoxy)quinazolin-4-amine/ hydroxypropylcellulose (HPC)/ polysorbate 80/benzalkonium chloride (BAC)/D-mannitol | Concentration (mg/mL) | Mean particle size (nm) |
|---|---|---|---|
| 150 | 1/0.5/0.1/0.001/0.1 | 9.33 | 114 |
| 151 | 1/0.125/0.025/0.00025/0.025 | 10.34 | 75 |

Example 152

N-(3-Chloro-4-fluorophenyl)-7-methoxy-6-(3-morpholin-4-ylpropoxy)quinazolin-4-amine (LC Laboratories, Inc.; the same holds true for the description below) was weighed into a zirconia container (Thinky Corp.) and subsequently prepared into a suspension by the addition of hydroxypropylcellulose (HPC), polysorbate 80, benzalkonium chloride (BAC), D-mannitol, and water. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to N-(3-chloro-4-fluorophenyl)-7-methoxy-6-(3-morpholin-4-ylpropoxy)quinazolin-4-amine/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight.

As a result of measuring the concentration of this nanoparticle composition, N-(3-chloro-4-fluorophenyl)-7-methoxy-6-(3-morpholin-4-ylpropoxy)quinazolin-4-amine had a concentration of 11.20 mg/mL.

As a result of assaying the nanoparticle composition using Zeta Sizer (Malvern instruments Nano series), N-(3-chloro-4-fluorophenyl)-7-methoxy-6-(3-morpholin-4-ylpropoxy)quinazolin-4-amine had a mean particle size of 123 nm in the nanoparticle composition.

Example 153

A nanoparticle composition having composition of N-(3-chloro-4-fluorophenyl)-7-methoxy-6-(3-morpholin-4-ylpropoxy)quinazolin-4-amine/hydroxypropylcellulose (HPC)/polysorbate 80/benzalkonium chloride (BAC)/D-mannitol=1 part by weight/0.125 parts by weight/0.025 parts by weight/0.00025 parts by weight/0.025 parts by weight and having N-(3-chloro-4-fluorophenyl)-7-methoxy-6-(3-morpholin-4-ylpropoxy)quinazolin-4-amine with a concentration of 11.31 mg/mL and a mean particle size of 147 nm was obtained from N-(3-chloro-4-fluorophenyl)-7-methoxy-6-(3-morpholin-4-ylpropoxy)quinazolin-4-amine, hydroxypropylcellulose (HPC), polysorbate 80, benzalkonium chloride (BAC), D-mannitol, and an aqueous glucose solution in accordance with Example 152 except that the amount of hydroxypropylcellulose (HPC) was changed from 0.5 parts by weight to 0.125 parts by weight; the amount of polysorbate 80 was changed from 0.1 parts by weight to 0.025 parts by weight; the amount of benzalkonium chloride (BAC) was changed from 0.001 parts by weight to 0.00025 parts by weight; and the amount of D-mannitol was changed from 0.1 parts by weight to 0.025 parts by weight.

Example 154

A nanoparticle composition having composition of N-(3-chloro-4-fluorophenyl)-7-methoxy-6-(3-morpholin-4-ylpropoxy)quinazolin-4-amine/hydroxypropylcellulose (HPC)/sodium lauryl sulfate=1 part by weight/0.125 parts by weight/0.01 parts by weight and having N-(3-chloro-4-fluorophenyl)-7-methoxy-6-(3-morpholin-4-ylpropoxy)quinazolin-4-amine with a concentration of 11.11 mg/mL and a mean particle size of 214 nm was obtained from N-(3-chloro-4-fluorophenyl)-7-methoxy-6-(3-morpholin-4-ylpropoxy)quinazolin-4-amine, hydroxypropylcellulose (HPC), sodium lauryl sulfate, and an aqueous glucose solution in accordance with Example 152 except that: the surfactant was changed from polysorbate 80 to sodium lauryl sulfate; the amount of hydroxypropylcellulose (HPC) was changed from 0.5 parts by weight to 0.125 parts by weight; and benzalkonium chloride (BAC) and D-mannitol were excluded from the composition.

Example 155

A nanoparticle composition having composition of N-(3-chloro-4-fluorophenyl)-7-methoxy-6-(3-morpholin-4-ylpropoxy)quinazolin-4-amine/hydroxypropylcellulose (HPC)/sodium lauryl sulfate=1 part by weight/0.125 parts by weight/0.001 parts by weight and having N-(3-chloro-4-fluorophenyl)-7-methoxy-6-(3-morpholin-4-ylpropoxy)quinazolin-4-amine with a concentration of 11.03 mg/mL and a mean particle size of 432 nm was obtained from N-(3-chloro-4-fluorophenyl)-7-methoxy-6-(3-morpholin-4-ylpropoxy)quinazolin-4-amine, hydroxypropylcellulose (HPC), sodium lauryl sulfate, and an aqueous glucose solution in accordance with Example 152 except that: the surfactant was changed from polysorbate 80 to sodium lauryl sulfate; the amount of hydroxypropylcellulose (HPC) was changed from 0.5 parts by weight to 0.125 parts by weight; and benzalkonium chloride (BAC) and D-mannitol were excluded from the composition.

TABLE 33

| Example | Compositional ratio (parts by weight) N-(3-chloro-4-fluorophenyl)-7-methoxy-6-(3-morpholin-4-ylpropoxy)quinazolin-4-amine/ hydroxypropylcellulose (HPC)/ polysorbate 80/benzalkonium chloride (BAC)/D-mannitol | Concentration (mg/mL) | Mean particle size (nm) |
| --- | --- | --- | --- |
| 152 | 1/0.5/0.1/0.001/0.1 | 11.20 | 123 |
| 153 | 1/0.125/0.025/0.00025/0.025 | 11.31 | 147 |

TABLE 34

| Example | Compositional ratio (parts by weight) N-(3-chloro-4-fluorophenyl)-7-methoxy-6-(3-morpholin-4-ylpropoxy)quinazolin-4-amine/ hydroxypropylcellulose (HPC)/ sodium lauryl sulfate/benzalkonium chloride (BAC)/D-mannitol | Concentration (mg/mL) | Mean particle size (nm) |
|---|---|---|---|
| 154 | 1/0.125/0,01/0/0 | 11.11 | 214 |
| 155 | 1/0.125/0.001/0/0 | 11.03 | 432 |

Example 156

A nanoparticle composition having composition of N-(3-chloro-4-fluorophenyl)-7-methoxy-6-(3-morpholin-4-ylpropoxy)quinazolin-4-amine/carboxymethylcellulose sodium (CMC Na)/polysorbate 80=1 part by weight/0.05 parts by weight/0.1 parts by weight and having N-(3-chloro-4-fluorophenyl)-7-methoxy-6-(3-morpholin-4-ylpropoxy) quinazolin-4-amine with a concentration of 13.47 mg/mL and a mean particle size of 264 nm was obtained from N-(3-chloro-4-fluorophenyl)-7-methoxy-6-(3-morpholin-4-ylpropoxy)quinazolin-4-amine, carboxymethylcellulose sodium (CMC Na), polysorbate 80, and an aqueous glucose solution in accordance with Example 152 except that: the thickening agent was changed from hydroxypropylcellulose (HPC) to carboxymethylcellulose sodium (CMC Na); and benzalkonium chloride (BAC) and D-mannitol were excluded from the composition.

Example 157

A nanoparticle composition having composition of N-(3-chloro-4-fluorophenyl)-7-methoxy-6-(3-morpholin-4-ylpropoxy)quinazolin-4-amine/carboxymethylcellulose sodium (CMC Na)/polysorbate 80=1 part by weight/0.05 parts by weight/0.001 parts by weight and having N-(3-chloro-4-fluorophenyl)-7-methoxy-6-(3-morpholin-4-ylpropoxy)quinazolin-4-amine with a concentration of 12.77 mg/mL and a mean particle size of 252 nm was obtained from N-(3-chloro-4-fluorophenyl)-7-methoxy-6-(3-morpholin-4-ylpropoxy)quinazolin-4-amine, carboxymethylcellulose sodium (CMC Na), polysorbate 80, and an aqueous glucose solution in accordance with Example 152 except that: the thickening agent was changed from hydroxypropylcellulose (HPC) to carboxymethylcellulose sodium (CMC Na); the amount of polysorbate was changed from 0.1 parts by weight to 0.001 parts by weight; and benzalkonium chloride (BAC) and D-mannitol were excluded from the composition.

Example 158

A nanoparticle composition having composition of N-(3-chloro-4-fluorophenyl)-7-methoxy-6-(3-morpholin-4-ylpropoxy)quinazolin-4-amine/carboxymethylcellulose sodium (CMC Na)/polysorbate 80=1 part by weight/0.025 parts by weight/0.1 parts by weight and having N-(3-chloro-4-fluorophenyl)-7-methoxy-6-(3-morpholin-4-ylpropoxy) quinazolin-4-amine with a concentration of 13.16 mg/mL and a mean particle size of 220 nm was obtained from N-(3-chloro-4-fluorophenyl)-7-methoxy-6-(3-morpholin-4-ylpropoxy)quinazolin-4-amine, carboxymethylcellulose sodium (CMC Na), polysorbate 80, and an aqueous glucose solution in accordance with Example 152 except that: the thickening agent was changed from hydroxypropylcellulose (HPC) to carboxymethylcellulose sodium (CMC Na); and benzalkonium chloride (BAC) and D-mannitol were excluded from the composition.

Example 159

A nanoparticle composition having composition of N-(3-chloro-4-fluorophenyl)-7-methoxy-6-(3-morpholin-4-ylpropoxy)quinazolin-4-amine/carboxymethylcellulose sodium (CMC Na)/polysorbate 80=1 part by weight/0.025 parts by weight/0.001 parts by weight and having N-(3-chloro-4-fluorophenyl)-7-methoxy-6-(3-morpholin-4-ylpropoxy)quinazolin-4-amine with a concentration of 12.47 mg/mL and a mean particle size of 187 nm was obtained from N-(3-chloro-4-fluorophenyl)-7-methoxy-6-(3-morpholin-4-ylpropoxy)quinazolin-4-amine, carboxymethylcellulose sodium (CMC Na), polysorbate 80, and an aqueous glucose solution in accordance with Example 152 except that: the thickening agent was changed from hydroxypropylcellulose (HPC) to carboxymethylcellulose sodium (CMC Na); the amount of polysorbate was changed from 0.1 parts by weight to 0.001 parts by weight; and benzalkonium chloride (BAC) and D-mannitol were excluded from the composition.

TABLE 35

| Example | Compositional ratio (parts by weight) N-(3-chloro-4-fluorophenyl)-7-methoxy-6-(3-morpholin-4-ylpropoxy)quinazolin-4-amine/ carboxymethylcellulose sodium (CMC Na)/ polysorbate 80/benzalkonium chloride (BAC)/D-mannitol | Concentration (mg/mL) | Mean particle size (nm) |
|---|---|---|---|
| 156 | 1/0.05/0.1/0/0 | 13.47 | 264 |
| 157 | 1/0.05/0.001/0/0 | 12.77 | 252 |
| 158 | 1/0.025/0.1/0/0 | 13.16 | 220 |
| 159 | 1/0.025/0.001/0/0 | 12.47 | 187 |

Example 160

A nanoparticle composition having composition of N-(3-chloro-4-fluorophenyl)-7-methoxy-6-(3-morpholin-4-ylpropoxy)quinazolin-4-amine/carboxymethylcellulose sodium (CMC Na)/sodium lauryl sulfate=1 part by weight/0.05 parts by weight/0.001 parts by weight and having N-(3-chloro-4-fluorophenyl)-7-methoxy-6-(3-morpholin-4-ylpropoxy)quinazolin-4-amine with a concentration of 10.70 mg/mL and a mean particle size of 255 nm was obtained from N-(3-chloro-4-fluorophenyl)-7-methoxy-6-(3-morpholin-4-ylpropoxy)quinazolin-4-amine, carboxymethylcellulose sodium (CMC Na), sodium lauryl sulfate (, and an aqueous glucose solution in accordance with Example 152 except that: the thickening agent was changed from hydroxypropylcellulose (HPC) to carboxymethylcellulose sodium (CMC Na); the surfactant was changed from polysorbate 80 to sodium lauryl sulfate; and benzalkonium chloride (BAC) and D-mannitol were excluded from the composition.

TABLE 36

| Example | Compositional ratio (parts by weight) N-(3-chloro-4-fluorophenyl)-7-methoxy-6-(3-morpholin-4-ylpropoxy)quinazolin-4-amine/ carboxymethylcellulose sodium (CMC Na)/ sodium lauryl sulfate/benzalkonium chloride (BAC)/D-mannitol | Concentration (mg/mL) | Mean particle size (nm) |
|---|---|---|---|
| 160 | 1/0.05/0.001/0/0 | 10.70 | 255 |

Example 161

A nanoparticle composition having composition of N-(3-chlorophenyl)-N-(6,7-dimethoxyquinazolin-4-yl)amine/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having a mean particle size of 1000 nm or smaller was obtained from N-(3-chlorophenyl)-N-(6,7-dimethoxyquinazolin-4-yl)amine, hydroxypropylcellulose (HPC), polysorbate 80, benzalkonium chloride (BAC), D-mannitol, and an aqueous glucose solution in accordance with Example 1 except that N-[2-chloro-4-(6,7-dimethoxyquinolin-4-yloxy)phenyl]-N'-(5-methylisoxazol-3-yl)urea hydrochloride hydrate was changed to N-(3-chlorophenyl)-N-(6,7-dimethoxyquinazolin-4-yl)amine.

Example 162

A nanoparticle composition having composition of N-[2-[[2-(dimethylamino)ethyl]methylamino]-5-[[4-(1H-indol-3-yl)-2-pyrimidinyl]amino]-4-methoxyphenyl]-2-propanamide/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having a mean particle size of 1000 nm or smaller was obtained from N-[2-[[2-(dimethylamino)ethyl]methylamino]-5-[[4-(1H-indol-3-yl)-2-pyrimidinyl]amino]-4-methoxyphenyl]-2-propanamide, hydroxypropylcellulose (HPC), polysorbate 80, benzalkonium chloride (BAC), D-mannitol, and an aqueous glucose solution in accordance with Example 1 except that N-[2-chloro-4-(6,7-dimethoxyquinolin-4-yloxy)phenyl]-N'-(5-methylisoxazol-3-yl)urea hydrochloride hydrate was changed to N-[2-[[2-(dimethylamino)ethyl]methylamino]-5-[[4-(1H-indol-3-yl)-2-pyrimidinyl]amino]-4-methoxyphenyl]-2-propanamide.

Example 163

A nanoparticle composition having composition of N4-[3-chloro-4-(thiazol-2-ylmethoxy)phenyl]-N6-[4(R)-methyl-4,5-dihydroxyoxazol-2-yl]quinazoline-4,6-diamine ditoluenesulfonate/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having a mean particle size of 1000 nm or smaller was obtained from N4-[3-chloro-4-(thiazol-2-ylmethoxy)phenyl]-N6-[4(R)-methyl-4,5-dihydroxyoxazol-2-yl]quinazoline-4,6-diamine ditoluenesulfonate, hydroxypropylcellulose (HPC), polysorbate 80, benzalkonium chloride (BAC), D-mannitol, and an aqueous glucose solution in accordance with Example 1 except that N-[2-chloro-4-(6,7-dimethoxyquinolin-4-yloxy)phenyl]-N'-(5-methylisoxazol-3-yl)urea hydrochloride hydrate was changed to N4-[3-chloro-4-(thiazol-2-ylmethoxy)phenyl]-N6-[4(R)-methyl-4,5-dihydroxyoxazol-2-yl]quinazoline-4,6-diamine ditoluenesulfonate.

Example 164

A nanoparticle composition having composition of (2Z)-but-2-enedionic acid N-[3-([2-[3-fluoro-4-(4-methylpiperazin-1-yl)anilino]-1H-pyrrolo[2,3-d]pyrimidin-4-yl]oxy)phenyl]prop-2-enamide/hydroxypropylcellulose (HPC)/polysorbate 80/benzalkonium chloride (BAC)/D-mannitol=1 part by weight/0.5 parts by weight/0.1 parts by weight/0.001 parts by weight/0.1 parts by weight and having a mean particle size of 1000 nm or smaller was obtained from (2Z)-but-2-enedionic acid N-[3-([2-[3-fluoro-4-(4-methylpiperazin-1-yl)anilino]-1H-pyrrolo[2,3-d]pyrimidin-4-yl]oxy)phenyl]prop-2-enamide, hydroxypropylcellulose (HPC), polysorbate 80, benzalkonium chloride (BAC), D-mannitol, and an aqueous glucose solution in accordance with Example 1 except that N-[2-chloro-4-(6,7-dimethoxyquinolin-4-yloxy)phenyl]-N'-(5-methylisoxazol-3-yl)urea hydrochloride hydrate was changed to (2Z)-but-2-enedionic acid N-[3-([2-[3-fluoro-4-(4-methylpiperazin-1-yl)anilino]-1H-pyrrolo[2,3-d]pyrimidin-4-yl]oxy)phenyl]prop-2-enamide.

Reference Example 11

4-{4-[3-(4-Chloro-3-trifluoromethylphenyl)-ureido]-3-fluorophenoxy}pyridine-2-carboxylic acid methylamide (Active Bio; the same holds true for the description below) was weighed into a zirconia container (Thinky Corp.) and subsequently prepared into a suspension by the addition of hydroxypropylcellulose (hydroxypropylcellulose (HPC), Wako Pure Chemical Industries, Ltd.; the same holds true for the description below), Tween 80 (Junsei Chemical Co., Ltd.; the same holds true for the description below), benzalkonium chloride (benzalkonium chloride (BAC), Nacalai Tesque, Inc.; the same holds true for the description below), D-mannitol (Junsei Chemical Co., Ltd.; the same holds true for the description below), and an aqueous glucose solution. Zirconia balls (zirconia milling balls, YTZ, diameter: 0.1 mm, Nikkato Corp.) were placed in the container, which was then covered with the lid. Wet milling (mill/mix 2000 rpm, 1 min, loop/30 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 4-{4-[3-(4-chloro-3-trifluoromethylphenyl)-ureido]-3-fluorophenoxy}pyridine-2-carboxylic acid methylamide/hydroxypropylcellulose (HPC)/Tween 80/benzalkonium chloride (BAC)/D-mannitol=1 part by weight/0.125 parts by weight/0.025 parts by weight/0.00025 parts by weight/0.025 parts by weight.

This nanoparticle composition was purified (13200 rpm, 15 min) using Micro Refrigerated Centrifuge (3740, Kubota Corp.) to adjust the concentration of 4-{4-[3-(4-chloro-3-trifluoromethylphenyl)-ureido]-3-fluorophenoxy}pyridine-2-carboxylic acid methylamide to 1.72 mg/mL.

As a result of assaying the nanoparticle composition using Zeta Sizer (Malvern instruments Nano series), 4-{4-[3-(4-chloro-3-trifluoromethylphenyl)-ureido]-3-fluorophenoxy}pyridine-2-carboxylic acid methylamide had a mean particle size of 97 nm in the nanoparticle composition.

Reference Example 12

4-{4-[3-(4-Chloro-3-trifluoromethylphenyl)-ureido]-3-fluorophenoxy}pyridine-2-carboxylic acid methylamide was weighed into a zirconia container (Thinky Corp.) and subsequently prepared into a suspension by the addition of hydroxypropylcellulose (hydroxypropylcellulose (HPC), Wako Pure Chemical Industries, Ltd.; the same holds true for the description below), Tween 80 (Junsei Chemical Co., Ltd.; the same holds true for the description below), benzalkonium chloride (benzalkonium chloride (BAC), Nacalai Tesque, Inc.; the same holds true for the description below), D-mannitol (Junsei Chemical Co., Ltd.; the same holds true for the description below), and an aqueous glucose solution. Zirconia balls (zirconia milling balls, YTZ, diameter: 1.0 mm, Nikkato Corp.) were placed in the container, which was then covered with the lid. Wet milling (mill/mix 2000 rpm, 1 min, loop/10 times/−10° C.) was performed using Rotation/Revolution Nano Pulverizer (NP-100, Thinky Corp.). Then, the milled product was diluted (mill/mix 400 rpm, 5 min) by the addition of an aqueous glucose solution, and the zirconia balls were removed through a screen (Clean Media 2000 rpm, 1 min, mill/mix 400 rpm, 1 min) to obtain a nanoparticle composition.

The composition of the nanoparticle composition was set to 4-{4-[3-(4-chloro-3-trifluoromethylphenyl)-ureido]-3-fluorophenoxy}pyridine-2-carboxylic acid methylamide/hydroxypropylcellulose (HPC)/Tween 80/benzalkonium chloride (BAC)/D-mannitol=1 part by weight/0.5 parts by weight/0.01 parts by weight/0.001 parts by weight/0.01 parts by weight.

As a result of measuring the concentration of this nanoparticle composition, 4-{4-[3-(4-chloro-3-trifluoromethylphenyl)-ureido]-3-fluorophenoxy}pyridine-2-carboxylic acid methylamide had a concentration of 12.90 mg/mL.

As a result of assaying the nanoparticle composition using Zeta Sizer (Malvern instruments Nano series), 4-{4-[3-(4-chloro-3-trifluoromethylphenyl)-ureido]-3-fluorophenoxy}pyridine-2-carboxylic acid methylamide had a mean particle size of 451 nm in the nanoparticle composition.

Reference Example 13

The nanoparticle composition prepared in Reference Example 12 was purified using Micro Refrigerated Centrifuge (3740, Kubota Corp.) to adjust the concentration of 4-{4-[3-(4-chloro-3-trifluoromethylphenyl)-ureido]-3-fluorophenoxy}pyridine-2-carboxylic acid methylamide to 2.06 mg/mL.

As a result of assaying the nanoparticle composition using Zeta Sizer (Malvern instruments Nano series), 4-{4-[3-(4-chloro-3-trifluoromethylphenyl)-ureido]-3-fluorophenoxy}pyridine-2-carboxylic acid methylamide had a mean particle size of 234 nm in the nanoparticle composition.

Comparative Example 1

4-{4-[3-(4-Chloro-3-trifluoromethylphenyl)-ureido]-3-fluorophenoxy}pyridine-2-carboxylic acid methylamide (Active Bio; the same holds true for the description below) was weighed into a polypropylene container and subsequently prepared into a suspension by the addition of light liquid paraffin (Nacalai Tesque, Inc.; the same holds true for the description below). Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310, Thinky Corp.; the same holds true for the description below). Then, the milled product was diluted by the addition of light liquid paraffin. Then, wet milling was performed using a rotation/revolution mixer, and the milled product was diluted by the addition of light liquid paraffin to obtain a microsuspension having 4-{4-[3-(4-chloro-3-trifluoromethylphenyl)-ureido]-3-fluorophenoxy}pyridine-2-carboxylic acid methylamide with a concentration of 21.1 mg/mL.

As a result of assaying the microsuspension using a laser diffraction/scattering particle size distribution measurement apparatus (Microtrac, Nikkiso Co., Ltd.), it was confirmed that a microparticle composition having 4-{4-[3-(4-chloro-3-trifluoromethylphenyl)-ureido]-3-fluorophenoxy}pyridine-2-carboxylic acid methylamide with a particle size of 5.15 μm in terms of D50 was prepared.

Comparative Example 2

[4-[N-(2,3-Dimethyl-2H-indazol-6-yl)-N-methylamino]pyrimidin-2-ylamino]-2-methylbenzenesulfonamide hydrochloride was weighed into a container, and subsequently, an aqueous solution of Captisol (CYDEX; the same holds true for the description below), sodium dihydrogen phosphate (Wako Pure Chemical Industries, Ltd.; the same holds true for the description below), and sodium chloride (Wako Pure Chemical Industries, Ltd.; the same holds true for the description below) were added thereto. The pH of the mixture was adjusted to 5.0 using sodium hydroxide to obtain a solution composition (aqueous pazopanib solution). The composition of the solution composition was set to [4-[N-(2,3-dimethyl-2H-indazol-6-yl)-N-methylamino]pyrimidin-2-ylamino]-2-methylbenzenesulfonamide hydrochloride/Captisol/phosphate/sodium chloride=5 mg/mL/70 mg/mL/3.45 mg/mL/1.45 mg/mL.

Comparative Example 3

N-[2-Chloro-4-(6,7-dimethoxyquinolin-4-yloxy)phenyl]-N'-(5-methylisoxazol-3-yl)urea hydrochloride hydrate was weighed into a polypropylene container and subsequently prepared into a suspension by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Then, wet milling was performed using a rotation/revolution mixer, and the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight to obtain a microsuspension having N-[2-chloro-4-(6,7-dimethoxyquinolin-4-yloxy)phenyl]-N'-(5-methylisoxazol-3-yl)urea hydrochloride hydrate with a concentration of 0.46 mg/mL.

As a result of assaying the microsuspension using a laser diffraction/scattering particle size distribution measurement apparatus (Microtrac, Nikkiso Co., Ltd.), N-[2-chloro-4-(6,7-dimethoxyquinolin-4-yloxy)phenyl]-N'-(5-methylisoxazol-3-yl)urea hydrochloride hydrate had a particle size of 8.56 μm in terms of D50.

Comparative Example 4

A microparticle composition having N-[2-chloro-4-(6,7-dimethoxyquinolin-4-yloxy)phenyl]-N'-(5-methylisoxazol-3-yl)urea hydrochloride hydrate with a concentration of 0.17 mg/mL and D50 of 6.83 μm was obtained in accordance with Comparative Example 1 except that N-[2-chloro-4-(6,7-dimethoxyquinolin-4-yloxy)phenyl]-N'-(5-methylisoxazol-3-yl)urea hydrochloride hydrate was used instead of 4-{4-[3-(4-chloro-3-trifluoromethylphenyl)-ureido]-3-fluorophenoxy}pyridine-2-carboxylic acid methylamide.

TABLE 37

| Comparative Example | Particle size (D50, μm) |
|---|---|
| 3 | 8.56 |
| 4 | 6.83 |

Comparative Example 5

N-[2-Chloro-4-(6,7-dimethoxyquinolin-4-yloxy)phenyl]-N'-(5-methylisoxazol-3-yl)urea hydrochloride hydrate was weighed into a polypropylene container and prepared into a suspension by the addition of an aqueous solution of phosphate-buffered saline. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous solution of phosphate-buffered saline. Then, wet milling was performed using a rotation/revolution mixer, and the milled product was diluted by the addition of an aqueous solution of phosphate-buffered saline to obtain a microsuspension having N-[2-chloro-4-(6,7-dimethoxyquinolin-4-yloxy)phenyl]-N'-(5-methylisoxazol-3-yl)urea hydrochloride hydrate with a concentration of 5.27 mg/mL.

As a result of assaying the microsuspension using a laser diffraction/scattering particle size distribution measurement apparatus (Microtrac, Nikkiso Co., Ltd.), N-[2-chloro-4-(6,7-dimethoxyquinolin-4-yloxy)phenyl]-N'-(5-methylisoxazol-3-yl)urea hydrochloride hydrate had a particle size of 4.80 μm in terms of D50.

Comparative Example 6

1-[[4-[(4-Fluoro-2-methyl-1H-indol-5-yl)oxy]-6-methoxyquinolin-7-yl]oxymethyl]cyclopropan-1-amine was weighed into a polypropylene container and subsequently prepared into a suspension by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARB-310). Then, the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Then, wet milling was performed using a rotation/revolution mixer, and the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight to obtain a microsuspension having 1-[[4-[(4-fluoro-2-methyl-1H-indol-5-yl)oxy]-6-methoxyquinolin-7-yl]oxymethyl]cyclopropan-1-amine with a concentration of 2.01 mg/mL.

As a result of assaying the microsuspension using a laser diffraction/scattering particle size distribution measurement apparatus (Microtrac, Nikkiso Co., Ltd.), 1-[[4-[(4-fluoro-2-methyl-1H-indol-5-yl)oxy]-6-methoxyquinolin-7-yl]oxymethyl]cyclopropan-1-amine had a particle size of 4.84 μm in terms of D50.

Comparative Example 7

4-[3-Chloro-4-(cyclopropylcarbamoylamino)phenoxy]-7-methoxyquinoline-6-carboxamide was weighed into a polypropylene container and subsequently prepared into a suspension by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight.

Then, wet milling was performed using a rotation/revolution mixer, and the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight to obtain a microsuspension having 4-[3-chloro-4-(cyclopropylcarbamoylamino)phenoxy]-7-methoxyquinoline-6-carboxamide with a concentration of 1.92 mg/mL.

As a result of assaying the microsuspension using a laser diffraction/scattering particle size distribution measurement apparatus (Microtrac, Nikkiso Co., Ltd.), 4-[3-chloro-4-(cyclopropylcarbamoylamino)phenoxy]-7-methoxyquinoline-6-carboxamide had a particle size of 4.59 μm in terms of D50.

Comparative Example 8

Methyl (3Z)-3-[({4-[N-methyl-2-(4-methylpiperazin-1-yl)acetamido]phenyl}amino)(phenyl)methylidene]-2-oxo-2·3-dihydro-1H-indole-6-carboxylate was weighed into a polypropylene container and subsequently prepared into a suspension by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Then, wet milling was performed using a rotation/revolution mixer, and the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Then, wet milling was performed using a rotation/revolution mixer to obtain a microsuspension having methyl (3Z)-3-[({4-[N-methyl-2-(4-methylpiperazin-1-yl)acetamido]phenyl}amino)(phenyl)methylidene]-2-oxo-2·3-dihydro-1H-indole-6-carboxylate with a concentration of 1.13 mg/mL.

As a result of assaying the microsuspension using a laser diffraction/scattering particle size distribution measurement apparatus (Microtrac, Nikkiso Co., Ltd.), methyl (3Z)-3-[({4-[N-methyl-2-(4-methylpiperazin-1-yl)acetamido]phenyl}amino)(phenyl)methylidene]-2-oxo-2·3-dihydro-1H-indole-6-carboxylate had a particle size of 5.37 μm in terms of D50.

Comparative Example 9

(E)-N-[4-(3-Chloro-4-fluoroanilino)-7-methoxyquinazolin-6-yl]-4-piperidin-1-ylbut-2-enamide was weighed into a polypropylene container and subsequently prepared into a suspension by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Then, wet milling was performed using a rotation/revolution mixer, and the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight to obtain a microsuspension having (E)-N-[4-(3-chloro-4-fluoroanilino)-7-methoxyquinazolin-6-yl]-4-piperidin-1-ylbut-2-enamide with a concentration of 2.01 mg/mL.

As a result of assaying the microsuspension using a laser diffraction/scattering particle size distribution measurement apparatus (Microtrac, Nikkiso Co., Ltd.), (E)-N-[4-(3-chloro-4-fluoroanilino)-7-methoxyquinazolin-6-yl]-4-piperidin-1-ylbut-2-enamide had a particle size of 4.43 μm in terms of D50.

Comparative Example 10

N-[4-[[3-Chloro-4-[(3-fluorobenzyl)oxy]phenyl]amino]quinazolin-6-yl]acrylamide was weighed into a polypropylene container and subsequently prepared into a suspension by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Then, wet milling was performed using a rotation/revolution mixer, and the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight to obtain a microsuspension having N-[4-[[3-chloro-4-[(3-fluorobenzyl)oxy]phenyl]amine]quinazolin-6-yl]acrylamide with a concentration of 2.14 mg/mL.

As a result of assaying the microsuspension using laser diffraction/scattering particle size distribution measurement apparatus (Microtrac, Nikkiso Co., Ltd.), N-[4-[[3-chloro-4-[(3-fluorobenzyl)oxy]phenyl]amino]quinazolin-6-yl]acrylamide had a particle size of 4.87 μm in terms of D50.

Comparative Example 11

1-N-[4-(6,7-Dimethoxyquinolin6-4-yl)oxyphenyl]-1-N'-(4-fluorophenyl)cyclopropane-1,1-dicarboxamide was weighed into a polypropylene container and subsequently prepared into a suspension by the addition of an aqueous glucose solution having composition of polysorbate 80=0.5 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of polysorbate 80=0.5 parts by weight. Then, wet milling was performed using a rotation/revolution mixer, and the milled product was diluted by the addition of an aqueous glucose solution having composition of polysorbate 80=0.5 parts by weight to obtain a microsuspension having 1-N-[4-(6,7-dimethoxyquinolin6-4-yl)oxyphenyl]-1-N'-(4-fluorophenyl)cyclopropane-1,1-dicarboxamide with a concentration of 2.20 mg/mL.

As a result of assaying the microsuspension using a laser diffraction/scattering particle size distribution measurement apparatus (Microtrac, Nikkiso Co., Ltd.), 1-N-[4-(6,7-dimethoxyquinolin6-4-yl)oxyphenyl]-1-N'-(4-fluorophenyl)cyclopropane-1,1-dicarboxamide had a particle size of 2.61 µm in terms of D50.

Comparative Example 12

6-(6,7-Dimethoxyquinazolin-4-yl)oxy-N,2-dimethyl-1-benzofuran-3-carboxamide was weighed into a polypropylene container and subsequently prepared into a suspension by the addition of an aqueous glucose solution having composition of polysorbate 80=0.5 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of polysorbate 80=0.5 parts by weight. Then, wet milling was performed using a rotation/revolution mixer, and the milled product was diluted by the addition of an aqueous glucose solution having composition of polysorbate 80=0.5 parts by weight to obtain a microsuspension having 6-(6,7-dimethoxyquinazolin-4-yl)oxy-N,2-dimethyl-1-benzofuran-3-carboxamide with a concentration of 2.00 mg/mL.

As a result of assaying the microsuspension using a laser diffraction/scattering particle size distribution measurement apparatus (Microtrac, Nikkiso Co., Ltd.), 6-(6,7-dimethoxyquinazolin-4-yl)oxy-N,2-dimethyl-1-benzofuran-3-carboxamide had a particle size of 2.73 µm in terms of D50.

Comparative Example 13

N-(3-Ethynylphenyl)-7,8,10,11,13,14-hexahydro-[1,4,7,10]tetraoxacyclododecino[2,3-g]quinazolin-4-amine was weighed into a polypropylene container and subsequently prepared into a suspension by the addition of an aqueous glucose solution having composition of hydroxypropylcellulose (HPC)/polysorbate 80/benzalkonium chloride (BAC)/D-mannitol=1 part by weight/0.2 parts by weight/0.002 parts by weight/0.2 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of hydroxypropylcellulose (HPC)/polysorbate 80/benzalkonium chloride (BAC)/D-mannitol=1 part by weight/0.2 parts by weight/0.002 parts by weight/0.2 parts by weight. Then, wet milling was performed using a rotation/revolution mixer, and the milled product was diluted by the addition of an aqueous glucose solution having composition of hydroxypropylcellulose (HPC)/polysorbate 80/benzalkonium chloride (BAC)/D-mannitol=1 part by weight/0.2 parts by weight/0.002 parts by weight/0.2 parts by weight to obtain a microsuspension having N-(3-ethynylphenyl)-7,8,10,11,13,14-hexahydro-[1,4,7,10]tetraoxacyclododecino[2,3-g]quinazolin-4-amine with a concentration of 2.12 mg/mL.

As a result of assaying the microsuspension using a laser diffraction/scattering particle size distribution measurement apparatus (Microtrac, Nikkiso Co., Ltd.), N-(3-ethynylphenyl)-7,8,10,11,13,14-hexahydro-[1,4,7,10]tetraoxacyclododecino[2,3-g]quinazolin-4-amine had a particle size of 11.44 µm in terms of D50.

Comparative Example 14

3-(2-Imidazo[1,2-b]pyridazin-3-ylethynyl)-4-methyl-N-[4-[(4-methylpiperazin-1-yl)methyl]-3-(trifluoromethyl)phenyl]benzamide was weighed into a polypropylene container and subsequently prepared into a suspension by the addition of an aqueous glucose solution having composition of hydroxypropylcellulose (HPC)=0.3 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of hydroxypropylcellulose (HPC)=0.3 parts by weight. Then, wet milling was performed using a rotation/revolution mixer, and the milled product was diluted by the addition of an aqueous glucose solution having composition of hydroxypropylcellulose (HPC)=0.3 parts by weight to obtain a microsuspension having 3-(2-imidazo[1,2-b]pyridazin-3-ylethynyl)-4-methyl-N-[4-[(4-methylpiperazin-1-yl)methyl]-(trifluoromethyl)phenyl]benzamide with a concentration of 2.59 mg/mL.

As a result of assaying the microsuspension using a laser diffraction/scattering particle size distribution measurement apparatus (Microtrac, Nikkiso Co., Ltd.), 3-(2-imidazo[1,2-b]pyridazin-3-ylethynyl)-4-methyl-N-[4-[(4-methylpiperazin-1-yl)methyl]-3-(trifluoromethyl)phenyl]benzamide had a particle size of 4.42 µm in terms of D50.

Comparative Example 15

N-Methyl-2-[[3-[(E)-2-pyridin-2-ylethenyl]-1H-indazol-6-yl]sulfanyl]benzamide was weighed into a polypropylene container and subsequently prepared into a suspension by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight. Then, wet milling was performed using a rotation/revolution mixer, and the milled product was diluted by the addition of an aqueous glucose solution having composition of hydroxypropylcellulose (HPC)/polysorbate 80/benzalkonium chloride (BAC)/D-mannitol=0.5 parts by weight/0.1 parts by weight/0.001 parts by weight/0.1 parts by weight to obtain a microsuspension having N-methyl-2-[[3-[(E)-2-pyridin-2-ylethenyl]-1H-indazol-6-yl]sulfanyl]benzamide with a concentration of 2.32 mg/mL.

As a result of assaying the microsuspension using a laser diffraction/scattering particle size distribution measurement apparatus (Microtrac, Nikkiso Co., Ltd.), N-methyl-2-[[3-[(E)-2-pyridin-2-ylethenyl]-1H-indazol-6-yl]sulfanyl]benzamide had a particle size of 6.83 μm in terms of D50.

Comparative Example 16

N-(3-Ethynylphenyl)-6,7-bis(2-methoxyethoxy)quinazolin-4-amine hydrochloride was weighed into a polypropylene container and subsequently prepared into a suspension by the addition of an aqueous glucose solution having composition of hydroxypropylcellulose (HPC)/polysorbate 80/benzalkonium chloride (BAC)/D-mannitol=0.125 parts by weight/0.025 parts by weight/0.00025 parts by weight/0.025 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of hydroxypropylcellulose (HPC)/polysorbate 80/benzalkonium chloride (BAC)/D-mannitol=0.125 parts by weight/0.025 parts by weight/0.00025 parts by weight/0.025 parts by weight. Then, wet milling was performed using a rotation/revolution mixer, and the milled product was diluted by the addition of an aqueous glucose solution having composition of hydroxypropylcellulose (HPC)/polysorbate 80/benzalkonium chloride (BAC)/D-mannitol=0.125 parts by weight/0.025 parts by weight/0.00025 parts by weight/0.025 parts by weight to obtain a microsuspension having N-(3-ethynylphenyl)-6,7-bis(2-methoxyethoxy)quinazolin-4-amine hydrochloride with a concentration of 10.24 mg/mL.

As a result of assaying the microsuspension using a laser diffraction/scattering particle size distribution measurement apparatus (Microtrac, Nikkiso Co., Ltd.), N-(3-ethynylphenyl)-6,7-bis(2-methoxyethoxy)quinazolin-4-amine hydrochloride had a particle size of 7.20 μm in terms of D50 in the microparticle composition.

Comparative Example 17

N-(3-Chloro-4-fluorophenyl)-7-methoxy-6-(3-morpholin-4-ylpropoxy)quinazolin-4-amine was weighed into a polypropylene container and subsequently prepared into a suspension by the addition of an aqueous glucose solution having composition of hydroxypropylcellulose (HPC)/polysorbate 80/benzalkonium chloride (BAC)/D-mannitol=0.125 parts by weight/0.025 parts by weight/0.00025 parts by weight/0.025 parts by weight. Stainless beads (diameter: 3.0 mm, Bio-Medical Science Co., Ltd.) were placed in the container, which was then covered with the lid. Wet milling was performed using a rotation/revolution mixer (Awatori-Rentaro ARE-310). Then, the milled product was diluted by the addition of an aqueous glucose solution having composition of hydroxypropylcellulose (HPC)/polysorbate 80/benzalkonium chloride (BAC)/D-mannitol=0.125 parts by weight/0.025 parts by weight/0.00025 parts by weight/0.025 parts by weight. Then, wet milling was performed using a rotation/revolution mixer, and the milled product was diluted by the addition of an aqueous glucose solution having composition of hydroxypropylcellulose (HPC)/polysorbate 80/benzalkonium chloride (BAC)/D-mannitol=0.125 parts by weight/0.025 parts by weight/0.00025 parts by weight/0.025 parts by weight to obtain a microsuspension having N-(3-chloro-4-fluorophenyl)-7-methoxy-6-(3-morpholin-4-ylpropoxy)quinazolin-4-amine with a concentration of 11.85 mg/mL.

As a result of assaying the microsuspension using a laser diffraction/scattering particle size distribution measurement apparatus (Microtrac, Nikkiso Co., Ltd.), N-(3-chloro-4-fluorophenyl)-7-methoxy-6-(3-morpholin-4-ylpropoxy)quinazolin-4-amine had a particle size of 7.07 μm in terms of D50 in the microparticle composition.

Test Example 1 Pharmacokinetics of Nanoparticle Composition of Present Invention and Microparticle Composition of Comparative Example Administered at Single Dose by Ocular Instillation to Rat The nanoparticle compositions of the present invention obtained in Examples 19 and 24 and the microparticle compositions obtained in Comparative Examples 3 and 4 were evaluated for their pharmacokinetics when administered at a single dose by ocular instillation (4 to 12 μL/eye, n=2 for each group) to rats. Each nanoparticle composition was administered at a single dose by ocular instillation to the right eyes of male Brown Norway rats. Four to 7 hours after the ocular instillation, each rat was euthanized, and the right eyeball was excised. The eyeball was washed, and an eyeball tissue sample (choroid/sclera) was then harvested.

A given amount of a 50 vol % methanol solution was added to the harvested eyeball tissue sample, which was then homogenized. Acetonitrile was further added thereto, and the mixture was stirred. The sample was centrifuged, and the supernatant was harvested. A 10 mmol/L ammonium acetate solution was added thereto to prepare an assay sample.

The drug concentration in the assay sample was measured using a liquid chromatograph-tandem mass spectrometer (LC/MS/MS). The results are shown in Table 38 and FIG. 1.

TABLE 38

| Example No. | Compound | Formulation concentration (mg/mL) | Mean particle size (nm) | Concentration in choroid and sclera (ng/g) | Concentration in choroid and sclera (ng/g)/ formulation concentration (mg/mL) |
|---|---|---|---|---|---|
| Example 19 | II | 0.49 | 133 | 435 | 888 |
| Example 24 | II | 0.54 | 153 | 378 | 700 |

TABLE 38-continued

| Example No. | Compound | Formulation concentration (mg/mL) | Mean particle size (nm) | Concentration in choroid and sclera (ng/g) | Concentration in choroid and sclera (ng/g)/ formulation concentration (mg/mL) |
|---|---|---|---|---|---|
| Comparative Example 3 | II | 0.46 | 8560 | 69.8 | 152 |
| Comparative Example 4 | II | 0.17 | 6830 | 32.5 | 191 |

Concentration in choroid and sclera and concentration in choroid and sclera/formulation concentration are indicated by mean (n=2).

Compound II: N-[2-chloro-4-(6,7-dimethoxyquinolin-4-yloxy)phenyl]-N'-(5-methylisoxazol-3-yl)urea Hydrochloride Hydrate Table 38 revealed that compound II in the form of a nanoparticle composition having a mean particle size of 1000 nm or smaller exhibits drastically enhanced transfer to the choroid and/or the sclera.

Test Example 2 Pharmacokinetics of Nanoparticle Composition of Present Invention Administered at Single Dose by Ocular Instillation to Rat The nanoparticle compositions of the present invention prepared according to Examples 1, 7, 9, 15, 27, 29 and 39 were evaluated for their pharmacokinetics when administered at a single dose by ocular instillation to rats. Each nanoparticle composition was administered at a single dose by ocular instillation to the right eyes of male Brown Norway rats (5 µL/eye, n=2 for each group). Four hours after the ocular instillation, each rat was euthanized, and the right eyeball was excised. The eyeball was washed, and a choroid/sclera sample was then harvested.

A given amount of a 50 vol % methanol solution was added to the harvested choroid/sclera sample, which was then homogenized. Acetonitrile was further added thereto, and the mixture was stirred. The sample was centrifuged, and the supernatant was harvested. A 10 mmol/L ammonium acetate solution was added thereto to prepare an assay sample.

The drug concentration in the assay sample was measured using a liquid chromatograph-tandem mass spectrometer (LC/MS/MS). The results are shown in Table 39.

Compound II: N-[2-chloro-4-(6,7-dimethoxyquinolin-4-yloxy)phenyl]-N'-(5-methylisoxazol-3-yl)urea Hydrochloride Hydrate Table 39 revealed that: compound II in the form of a nanoparticle composition having a mean particle size of smaller than 400 nm is preferred for transfer to the choroid and/or the sclera; compound II having a mean particle size of smaller than 200 nm is more preferred for transfer to the choroid and/or the sclera; and compound II having a mean particle size of smaller than 120 nm is further preferred for transfer to the choroid and/or the sclera.

Test Example 3 Pharmacokinetics of Nanoparticle Composition of Present Invention Administered at Single Dose by Ocular Instillation to Rat The nanoparticle compositions of the present invention prepared in accordance with Examples 1 and 26 and the nanoparticle compositions of the present invention obtained in Examples 50, 52, 53, 54, 57 and 96 were evaluated for their pharmacokinetics when administered at a single dose by ocular instillation to rats. Each nanoparticle composition was administered at a single dose by ocular instillation to the right eyes of male Brown Norway rats (5 µL/eye, n=2 for each group). Four hours after the ocular instillation, each rat was euthanized, and the right eyeball was excised. The eyeball was washed, and a choroid/sclera sample was then harvested.

A given amount of a 50 vol % methanol solution was added to the harvested choroid/sclera sample, which was then homogenized. Acetonitrile was further added thereto, and the mixture was stirred. The sample was centrifuged, and the supernatant was harvested. A 10 mmol/L ammonium acetate solution was added thereto to prepare an assay sample.

TABLE 39

| Example No. for reference | Compound | Formulation concentration (mg/mL) | Mean particle size (nm) | Concentration in choroid and sclera (ng/g) | Concentration in choroid and sclera (ng/g)/ formulation concentration (mg/mL) |
|---|---|---|---|---|---|
| Example 1 | II | 1.26 | 130 | 1330 | 1060 |
| Example 7 | II | 1.65 | 189 | 1320 | 800 |
| Example 9 | II | 1.51 | 167 | 1580 | 1050 |
| Example 15 | II | 0.410 | 421 | 400 | 976 |
| Example 27 | II | 1.59 | 94 | 1020 | 642 |
| Example 29 | II | 1.58 | 96 | 1440 | 911 |
| Example 39 | II | 1.57 | 111 | 1130 | 920 |

Concentration in choroid and sclera and concentration in choroid and sclera/formulation concentration are indicated by mean (n=3).

The drug concentration in the assay sample was measured using a liquid chromatograph-tandem mass spectrometer (LC/MS/MS). The results are shown in Table 40.

TABLE 40

| Example No. for reference or Example No. | Compound | Formulation concentration (mg/mL) | Mean particle size (nm) | Concentration in choroid and sclera (ng/g) | Concentration in choroid and sclera (ng/g)/ formulation concentration (mg/mL) |
|---|---|---|---|---|---|
| Example 1  | II | 1.26 | 130 | 1110 | 881 |
| Example 26 | II | 1.61 | 145 | 1130 | 702 |
| Example 50 | II | 1.31 | 133 | 1170 | 893 |
| Example 52 | II | 1.35 | 137 | 654  | 484 |
| Example 53 | II | 0.75 | 227 | 573  | 764 |
| Example 54 | II | 1.30 | 203 | 1020 | 785 |
| Example 57 | II | 1.62 | 128 | 1130 | 698 |
| Example 96 | II | 2.06 | 206 | 460  | 223 |

Concentration in choroid and sclera and concentration in choroid and sclera/formulation concentration are indicated by mean (n=3).

Compound II: N-[2-chloro-4-(6,7-dimethoxyquinolin-4-yloxy)phenyl]-N'-(5-methylisoxazol-3-yl)urea Hydrochloride Hydrate As seen from Table 40, compound II in a nanoparticle form exhibited high transfer to the choroid and/or the sclera, regardless of the composition of the formulation thereof. On the other hand, only the composition of Example 96, which was an eye ointment obtained with glycerol as a dispersion media, exhibited reduced transfer into the choroid and/or the sclera.

Test Example 4 Pharmacokinetics of Nanoparticle Composition of Present Invention and Microparticle Composition of Comparative Example Administered at Single Dose by Ocular Instillation to Rabbit The nanoparticle compositions of the present invention prepared according to Examples 1 and 40, the nanoparticle composition of the present invention obtained in Example 84, and the microparticle composition prepared according to Comparative Example 5 were evaluated for their pharmacokinetics when administered at a single dose by ocular instillation (20 μL/eye) to Kbl:Dutch rabbits. Each nanoparticle composition of the present invention obtained as the nanoparticle composition prepared according to Example 1, the nanoparticle composition prepared according to Example 40, and the nanoparticle composition prepared according to Example 84, or the microparticle composition prepared according to Comparative Example 5 was administered at a single dose by ocular instillation to the right eyes of the animals (n=3 for each condition). 1.5 hours after the ocular instillation, each animal was euthanized, and the eyeballs were excised. The eyeballs were washed, and a choroid/retina sample was then harvested.

A given amount of a 50 vol % methanol solution was added to the harvested choroid/retina sample, which was then homogenized. Acetonitrile was further added thereto, and the mixture was stirred. The sample was centrifuged, and the supernatant was harvested. A 10 mmol/L ammonium acetate solution was added thereto to prepare an assay sample.

The concentration of compound II in the assay sample was measured using a liquid chromatograph-tandem mass spectrometer (LC/MS/MS). The results are shown in Tables 41 and 42.

TABLE 41

| | | Compound II concentration in choroid and retina (ng/g) | | | |
|---|---|---|---|---|---|
| Example No. for reference or Example No. | | Example 40 | Example 1 | Example 84 | Comparative Example 5 |
| Tissue | Formulation concentration (mg/mL) | 1.72 | 2.02 | 2.05 | 5.49 |
|        | Mean particle size (nm) | 64 | 139 | 365 | 7530 |
| Right eye (administration eye) | Mean | 194 | 130 | 94.7 | 65.5 |
|                                | Standard deviation | 71 | 57 | 42.4 | 39.5 |
| Left eye (non-administration eye) | Mean | 14.8 | 22.8 | 6.90 | 4.30 |
|                                   | Standard deviation | 8 | 13.1 | 0.77 | 1.53 |

Mean (n = 3)

Compound II: N-[2-chloro-4-(6,7-dimethoxyquinolin-4-yloxy)phenyl]-N'-(5-methylisoxazol-3-yl)urea Hydrochloride Hydrate

TABLE 42

| | | Compound II concentration in choroid and retina (ng/g)/ formulation concentration (mg/mL) | | | |
|---|---|---|---|---|---|
| Example No. for reference or Example No. | | Example 40 | Example 1 | Example 84 | Comparative Example 5 |
| Tissue | Formulation concentration (mg/mL) | 1.72 | 2.02 | 2.05 | 5.49 |
|        | Mean particle size (nm) | 64 | 139 | 365 | 7530 |

TABLE 42-continued

| | | Compound II concentration in choroid and retina (ng/g)/ formulation concentration (mg/mL) | | | |
|---|---|---|---|---|---|
| Example No. for reference or Example No. | | Example 40 | Example 1 | Example 84 | Comparative Example 5 |
| Right eye (administration eye) | Mean | 113 | 64.3 | 46.2 | 11.9 |
| | Standard deviation | 41 | 28.4 | 20.7 | 7.2 |

Mean (n = 3)

Tables 41 and 42 revealed that: compound II in the form of a nanoparticle composition having a mean particle size of smaller than 400 nm is preferred for transfer to the choroid and/or the retina; compound II having a mean particle size of smaller than 150 nm is more preferred for transfer to the choroid and/or the retina; and compound II having a mean particle size of smaller than 70 nm is further preferred for transfer to the choroid and/or the retina.

Tables 41 and 42 demonstrated that when the nanoparticle composition of the present invention and the microparticle composition of Comparative Example were administered at a single dose by ocular instillation to rabbits, compound II having a smaller particle size exhibited higher transfer to the choroid and/or the retina.

Test Example 5 Pharmacokinetics of Nanoparticle Composition Obtained in Reference Example and Microparticle Composition of Comparative Example Administered at Single Dose by Ocular Instillation to Rabbit The nanoparticle compositions obtained in Reference Examples 11 to 13 and the microparticle composition prepared according to Comparative Example 1 were evaluated for their pharmacokinetics when administered at a single dose by ocular instillation (20 μL/eye) to Kbl:Dutch rabbits. Each of the nanoparticle compositions obtained in Reference Examples 11 to 13 and the microparticle composition prepared according to Comparative Example 1 was administered at a single dose by ocular instillation to the left eyes of the animals (n=3 for each condition). 1.5 hours after the ocular instillation, each animal was euthanized, and the eyeballs were excised. The eyeballs were washed, and a choroid/retina sample was then harvested.

A given amount of a 50 vol % methanol solution was added to the harvested choroid/retina sample, which was then homogenized. Acetonitrile was further added thereto, and the mixture was stirred. The sample was centrifuged and the supernatant was harvested. A 10 mmol/L ammonium acetate solution was added thereto to prepare an assay sample.

The concentration of compound III in the assay sample was measured using a liquid chromatograph-tandem mass spectrometer (LC/MS/MS). The results are shown in Table 43.

TABLE 43

| | | Compound III concentration in choroid and retina (ng/g) | | | |
|---|---|---|---|---|---|
| Reference Example No. or Comparative Example No. for reference | | Reference Example 11 | Reference Example 12 | Reference Example 13 | Comparative Example 1 |
| Tissue | Formulation concentration (mg/mL) | 1.72 | 12.90 | 2.06 | 24.13 |
| | Mean particle size (nm) | 97 | 451 | 234 | 6400 |
| Left eye | Mean | 3.73 | 1.84 | 1.24 | Less than lower limit of quantification |
| | Standard deviation | 0.56 | 0.74 | 135 | impossible to calculate |

Mean (n = 3)

Less than lower limit of quantification: less than 1 ng/g

Compound III: 4-{4-[3-(4-chloro-3-trifluoromethylphenyl)-ureido]-3-fluorophenoxy}pyridine-2-carboxylic Acid Methylamide (Regorafenib)

Table 43 revealed that when the nanoparticle composition obtained in Reference Example and the microparticle composition of Comparative Example were administered at a single dose by ocular instillation to rabbits, the transfer of compound III to the choroid was very low for all the particle sizes evaluated.

Test Example 6 Pharmacokinetics of Nanoparticle Composition of Present Invention Prepared According to Example 1 and Microparticle Composition Prepared According to Comparative Example 1, Administered at Single Dose by Ocular Instillation to Cynomolgus Monkey The nanoparticle composition of the present invention prepared according to Example 1 and the microparticle composition prepared according to Comparative Example 1 were evaluated for their pharmacokinetics when administered at a single dose by ocular instillation to male cynomolgus monkeys. The nanoparticle composition of the present invention prepared according to Example 1 was administered by ocular instillation (50 μL/eye) to the right eye of each animal, while the microparticle composition prepared according to Comparative Example 1 was administered by ocular instillation (50 μL/eye) to the left eye thereof. Four hours or 48 hours (n=2 for each point in time) after the ocular instillation, blood was collected. Then, the animal was euthanized, and the eyeballs were excised. The eyeballs were washed, and a choroid tissue was then harvested.

A given amount of a 50 vol % methanol solution was added to the harvested choroid sample, which was then homogenized. Acetonitrile was further added thereto, and the mixture was stirred. The sample was centrifuged, and the supernatant was harvested. A 10 mmol/L ammonium acetate solution was added thereto to prepare an assay sample. The drug concentration in the assay sample was measured using a liquid chromatograph-tandem mass spectrometer (LC/MS/MS), and the drug concentration in the eye tissue sample was calculated. The results are shown in Table 44.

TABLE 44

| Example No. for reference or Comparative Example No. for reference (administration eye) | Compound | Formulation concentration (mg/mL) | Mean particle size (nm) | Concentration in choroid (ng/g) 4 hr | 48 hr |
|---|---|---|---|---|---|
| Example 1 (right eye) | II | 1.14 | 108 | 51.8 | 69.3 |
| Comparative Example 1 (left eye) | II | 17.1 | 4620 | 1.98 | 6.2 |

Mean (n = 2)

Compound II: N-[2-chloro-4-(6,7-dimethoxyquinolin-4-yloxy)phenyl]-N'-(5-methylisoxazol-3-yl)urea Hydrochloride Hydrate Compound III: Regorafenib (4-{4-[3-(4-chloro-3-trifluoromethylphenyl)-ureido]-3-fluorophenoxy}pyridine-2-carboxylic Acid Methylamide)

When the nanoparticle composition of the present invention prepared according to Example 1 or the microparticle composition prepared according to Comparative Example 1 was administered at a single dose by ocular instillation to male cynomolgus monkeys, the concentration in the choroid of N-[2-chloro-4-(6,7-dimethoxyquinolin-4-yloxy)phenyl]-N'-(5-methylisoxazol-3-yl)urea hydrochloride hydrate (compound II) comprised in the nanoparticle composition of the present invention prepared according to Example 1 was much higher than that of regorafenib (compound III) comprised in the microparticle composition prepared according to Comparative Example 1.

Test Example 7 Anti-Angiogenic Effect of Nanoparticle Composition of Present Invention on Laser-Induced Choroidal Neovascularization Model of Rat This test aims at evaluating whether or not the nanoparticle composition of the present invention exhibits an anti-angiogenic effect on a laser-induced choroidal neovascularization model of a rat, which is a typical wet age-related macular degeneration model.

The mydriasis of the eyeballs of each male Brown Norway rat (n=12 or 13 for each group) was caused with mydriatic eye drops for examination. A ketamine hydrochloride/xylazine hydrochloride (7:1, v/v) mixed solution was intramuscularly administered (1 mL/kg) to the femur for general anesthesia. Then, the right eyeground was observed using a slit lamp, and 8 sites in the retina were irradiated with laser (wavelength: 532 nm, spot size: 80 μm, irradiation time: 0.05 sec, output: 120 mW) using a multicolor laser photocoagulator to prepare laser-induced choroidal neovascularization model animals.

A vehicle of Example 1 or the nanoparticle composition of the present invention obtained in each of Examples 1 and 2 was administered twice a day by ocular instillation (5 μL/eye, 6 hr:18 hr interval) to each model animal from immediately after the laser irradiation to 14 days after the laser irradiation. Aflibercept (EYLEA(Registered Trademark) solution for intravitreal injection, Bayer Corp.) was intravitreally injected (5 μL/eye, once) thereto immediately after the laser irradiation.

Fourteen days after the laser irradiation, a 4% (v/v) FITC-dextran solution was administered (1 mL/animal) to the tail vein under general anesthesia. The animal was euthanized by excessive anesthesia through isoflurane (Mylan N.V.) inhalation, and the eyeballs were excised. The excised eyeballs were fixed for 24 hours in a 0.1 mol/L phosphate buffer solution containing 4% paraformaldehyde (PFA).

In order to prepare a choroid flat mount preparation, a hole was made in the corneal limbus of the eyeballs thus fixed using an injection needle under a stereoscopic microscope (EZ-4, Leica Microsystems GmbH), and the whole cornea, the iris and the crystalline lens were resected starting at the hole to create an optic cup state. Retina tissues other than retinal pigment epithelial cells were detached, and the optic cup was divided. Fluoromount (Diagnostic BioSystems (DBS)) was added dropwise thereto. A preparation was prepared by enclosure with a cover glass and dried at 4° C. for 24 hours in the dark.

A choroidal neovascular site was photographed using a confocal microscope (Nikon ECLIPSE TE 2000-U). For choroidal neovascular evaluation, an area (unit: pixel) that contained a newly formed blood vessel and was at the inner side relative to the highest raised portion was calculated using ImageJ (National Institutes of Health). Then, an average neovascular area of 3 or more sites, except for obscure laser irradiation sites, among data on the 8 sites per eye was used as an individual value to calculate an average area of each group. For statistical processing, the Bartlett test was conducted on the aflibercept (EYLEA(Registered Trademark) solution for intravitreal injection, Bayer Corp.) administration group, the Example 1 administration group and the Example 2 administration group vs. the vehicle group. In the case of equal variance, the Dunnet test was conducted. The tests employed statistical analysis software (Stat Light, Yukms Co. Ltd.), and the significance level was set to 5% (two-tailed test) in all the tests. The results are shown in FIG. 2 and Table 45.

TABLE 45

| Administered substance or Example No. | Vehicle of Example 1 | Aflibercept (EYLEA) | Example 1 | Example 2 |
|---|---|---|---|---|
| Mean | 127002.7 | 102931.7* | 106577.7* | 93936.9* |
| Standard deviation | 12460.8 | 18761.7 | 14207.9 | 12632.9 |
| Standard error | 3456.0 | 5416.0 | 3940.5 | 3503.7 |

Mean (n = 12 or 13)
*$p < 0.05$, vehicle vs. aflibercept, Example 1 and Example 2

When the nanoparticle compositions of the present invention obtained in Examples 1 and 2 were administered by ocular instillation to the laser-induced choroidal neovascularization models of rats, an anti-angiogenic effect equivalent to or higher than that of aflibercept (EYLEA, intravitreal injection) was confirmed.

Test Example 8 Pharmacological Effects of Nanoparticle Composition of Present Invention and Solution of Comparative Example on Laser-Induced Choroidal Neovascularization Model of Cynomolgus Monkey This test aims at evaluating whether or not the nanoparticle composition of the present invention exhibits a pharmacological effect on a laser-induced choroidal neovascularization model of a cynomolgus monkey, which is a typical wet age-related macular degeneration model.

Twenty-one days before the start of drug administration, both the eyes of each animal (all cases) were irradiated with laser to prepare animal models. Drops of a mydriatic agent were placed in the animal eyes to be irradiated. After confirmation of mydriasis, a mixed solution of ketamine hydrochloride (50 mg/mL) and an aqueous xylazine solution (20 mg/mL) [7:1 (v/v)] was intramuscularly administered (0.2 mL/kg or 10 mg/kg) to each animal. An appropriate amount of a special aid for contact lens placement to the cornea (Scopisol Solution for Eye) was added dropwise to an eyepiece of a retinal laser lens. The retinal laser lens was pressure-bonded to the eyes to be irradiated, and a yellow spot was confirmed. After the confirmation of a yellow spot, 8 sites around the yellow spot excluding the central pit were irradiated with green laser (wavelength: 532 nm, irradiation spot size: 80 μm, irradiation time; 0.1 sec, output: 1000 mW) using a multicolor laser photocoagulator (MC-500, Nidek Co., Ltd.).

According to the test configuration shown in Table 46, a vehicle, the nanoparticle composition of the present invention prepared according to Example 1, and the solution composition obtained in Comparative Example 2 were administered four times a day by ocular instillation for 35 days to the animal. Aflibercept (EYLEA(Registered Trademark) solution for intravitreal injection, Bayer Corp.) was intravitreally injected (once) to the animal.

Ophthalmoscopic examination was carried out during the acclimatization period (day −1) and during the administration period (administration days 7, 14, 21, 28 and 34). Macroscopic examination and light reflex examination were carried out using a portable slit lamp (SL-15, Kowa Co., Ltd.). Drops of a mydriatic agent were placed in the animal eyes. After confirmation of mydriasis, ketamine hydrochloride (50 mg/mL) was intramuscularly administered (0.2 mL/kg or 10 mg/kg) to each animal. The anterior segment of the eye and the ocular media were examined using a portable slit lamp, while the eyegrounds were examined using a head-type binocular indirect ophthalmoscope (IO-αSmall Pupil, Neitz Instruments Co., Ltd.). The eyegrounds were photographed using a fundus camera (VX-10α, Kowa Co., Ltd.) in all cases.

Fluorescein fundus angiography was carried out during the acclimatization period (day −1) and during the administration period (administration days 7, 14, 21, 28 and 34). For examination, a contrast medium (Fluorescite Intravenous Injection 500 mg, Alcon Japan Ltd.) was administered (0.1 mL/kg or 0.1 mL/s) from the cephalic vein of the forearm under mydriasis and anesthesia of the macroscopic examination and the ophthalmoscopic examination. Approximately 1, 3, and 5 minutes after the contrast medium administration, photographs were taken using a fundus camera. Choroidal neovascular grading was carried out on an irradiation spot basis. The fluorescein fundus angiographic images were observed and graded on an irradiation spot basis according to the criteria of Table 47.

TABLE 47

| Grade 1 | No hyperfluorescence |
|---|---|
| Grade 2 | Hyperfluorescence without leakage |
| Grade 3 | Hyperfluorescence at the first[a] or middle[b] stage of angiography and fluorescent leakage at the late stage[c] of angiography |
| Grade 4 | Clear hyperfluorescence at the first[a] or middle[b] stage of angiography and fluorescent leakage at the late stage[c] except for injured region |

[a] Fluorescein fundus image taken approximately 1 minute after the contrast medium administration
[b] Fluorescein fundus image taken approximately 3 minutes after the contrast medium administration
[c] Fluorescein fundus image taken approximately 5 minutes after the contrast medium administration The incidences of grades 1 to 4 of each eye at each point in time of examination were each calculated according to the following expression:

Incidence of grade (%)=The number of irradiation spots/8×100

The results about the incidence of grade 4 are shown in Table 48 and FIG. 3.

TABLE 46

| Test substance Example No. for reference or Comparative Example No. | Administration route* | Dose (mg/eye) | Dosing solution concentration (mg/mL) | Dosing volume (μL/eye) | The number of animals |
|---|---|---|---|---|---|
| Vehicle of Example 1 | Ocular instillation | — | — | 20 | 6 |
| Example 1 | | 0.04 | 2 | 20 | 6 |
| Comparative Example 2 | | 0.15 | 5 | 30 | 6 |
| Aflibercept | Intravitreal injection | 0.5 | 10 | 50 | 6 |

TABLE 48

| Group | | Day | | | | | |
|---|---|---|---|---|---|---|---|
| | | −1 | 7 | 14 | 21 | 28 | 34 |
| Vehicle of Example 1 | Mean | 31.3 | 22.9 | 18.8 | 20.8 | 20.8 | 20.8 |
| | Standard error | 13.2 | 13.1 | 12.0 | 11.5 | 11.5 | 11.5 |
| Example 1 | Mean | 52.1 | 8.3 | 6.3 | 6.3 | 6.3 | 4.2 |
| | Standard error | 14.2 | 6.2 | 6.3 | 6.3 | 6.3 | 4.2 |
| Comparative Example 2 | Mean | 50.0 | 47.9 | 43.8 | 45.8 | 43.8 | 43.8 |
| | Standard error | 10.7 | 15.9 | 15.7 | 15.0 | 15.1 | 15.1 |
| Aflibercept | Mean | 43.8 | 4.2 | 4.2 | 4.2 | 4.2 | 4.2 |
| | Standard error | 11.5 | 4.2 | 4.2 | 4.2 | 4.2 | 4.2 |

Mean (n = 6)
Standard error (n = 6)

When the nanoparticle composition of the present invention obtained in Example 1 was administered by ocular instillation to the laser-induced choroidal neovascularization models of cynomolgus monkeys, an anti-angiogenic effect equivalent to that of aflibercept (EYLEA, intravitreal injection) was confirmed and the effect was much higher than that of the solution composition obtained in Comparative Example 2.

Test Example 9 Pharmacological Effect of Nanoparticle Composition of Present Invention on Oxygen-Induced Retinopathy Model of Mouse This test aims at evaluating whether or not the nanoparticle composition of the present invention exhibits a pharmacological effect on an oxygen-induced retinopathy model of a mouse, which is a typical diabetic retinopathy model.

Each immature (1-week-old) 129SVE mouse (n=10 to 12 for each group) was subjected to high-oxygen loading treatment (under 75% oxygen, 5 days). Then, a vehicle or the nanoparticle composition of the present invention prepared in accordance with Example 1 was administered twice a day (once between 8 a.m. and 9 a.m. and once between 4 p.m. and 5 p.m.) by ocular instillation (2 μL/eye) to the right eye for 5 days under normal oxygen. After the completion of the administration period, ketamine/xylazine was intraperitoneally administered thereto for anesthesia, and the animal was euthanized by the intraperitoneal administration of Euthasol. The eyeballs were excised and fixed by treatment with 4% paraformaldehyde at room temperature for 1 hour. Retina tissues were isolated from the fixed eyeballs and stained with a calcium chloride buffer solution containing Isolectin-B4. The eyeballs were washed, and a flat mount preparation was then prepared. A neovascular area (the ratio of a neovascular area to the total tissue area of the retina) in the retina was evaluated under a microscope.

For statistical processing, significant difference was tested by the unpaired t-test on the administration group of the pharmaceutical composition of the present invention prepared according to Example 1 vs. the vehicle group. The tests employed Graphpad Prism as statistical analysis software, and the significance level was set to 5% in all the tests.

The results are shown in Table 49 and FIG. 4.

TABLE 49

| | Ratio of neovascular area to total tissue area of retina (% of Total Retinal Area) | |
|---|---|---|
| | Vehicle | Example 1 |
| Mean | 18.88 | 11.30 |
| Median | 19.68 | 10.13 |
| Maximum | 22.35 | 14.88 |
| Minimum | 11.34 | 9.60 |
| Standard deviation | 3.76 | 1.91 |
| Standard error | 1.19 | 0.60 |

When the pharmaceutical composition of the present invention prepared in accordance with Example 1 was administered twice a day by ocular instillation to the oxygen-induced retinopathy models of mice, a significant anti-angiogenic effect ($p<0.001$; unpaired student t-test) in the retina was confirmed as compared with the vehicle group.

Test Example 10 Pharmacokinetics of Nanoparticle Composition of Present Invention and Microparticle Composition of Comparative Example Administered at Single Dose by Ocular Instillation to Rat The nanoparticle compositions of the present invention obtained in Example 101, Example 108, Example 112, Reference Example 9 and Reference Example 10 and the microparticle compositions of Comparative Examples 6, 7, 8, 9 and 10 were evaluated for their pharmacokinetics when administered at a single dose by ocular instillation to Brown-Norway rats. Each of the nanoparticle compositions of the present invention obtained in Example 101, Example 108, Example 112, Reference Example 9 and Reference Example 10 and the microparticle compositions of Comparative Examples 6, 7, 8, 9 and 11 was administered at a single dose by ocular instillation to the right eye of each animal (n=2 for each condition). 1.5 hours after the ocular instillation, blood was collected. Then, the animal was euthanized, and both the eyeballs were excised. The eyeballs were washed, and a choroid/sclera sample was then harvested.

A given amount of a 50 vol % methanol solution was added to the harvested choroid/retina sample, which was then homogenized. Acetonitrile was further added thereto, and the mixture was stirred. The sample was centrifuged, and the supernatant was harvested. A 0.1 vol % formic acid solution was added thereto to prepare an assay sample.

A given amount of a 50 vol % methanol solution was added to the harvested choroid sample, which was then homogenized. Acetonitrile was further added thereto, and the mixture was stirred. The sample was centrifuged, and the supernatant was harvested. A 0.1 vol % formic acid solution was added thereto to prepare an assay sample.

The drug concentration in the assay sample was measured using a liquid chromatograph-tandem mass spectrometer (LC/MS/MS). The results are shown in Table 50 and FIG. 5.

TABLE 50

| Example No. for reference, Reference Example No., Example No. or Comparative Example No. | Compound | Formulation concentration (mg/mL) | Mean particle size or D50 (nm) | Concentration in choroid and sclera (ng/g) | Concentration in choroid and sclera (ng/g)/ formulation concentration (mg/mL) |
|---|---|---|---|---|---|
| Example 101 | IV | 2.34 | 106 | 132 | 56.4 |
| Reference Example 9 | V | 2.39 | 228 | 36.0 | 15.1 |
| Reference Example 10 | VI | 1.60 | 147 | 21.2 | 13.2 |
| Example 108 | VII | 2.39 | 94 | 249 | 104 |
| Example 112 | VIII | 2.45 | 204 | 106 | 43.3 |
| Comparative Example 6 | IV | 2.01 | 4840 | 75.8 | 37.7 |
| Comparative Example 7 | V | 1.92 | 4590 | 31.0 | 16.1 |
| Comparative Example 8 | VI | 1.13 | 5370 | 15.4 | 13.6 |
| Comparative Example 9 | VII | 2.01 | 4430 | 27.8 | 13.8 |
| Comparative Example 10 | VIII | 2.14 | 4870 | 28.0 | 13.1 |

Compound IV: Anlotinib (1-[[4-[(4-fluoro-2-methyl-1H-indol-5-yl)oxy]-6-methoxyquinolin-7-yl]oxymethyl]cyclopropan-1-amine)

Compound V: Lenvatinib (4-[3-chloro-4-(cyclopropylcarbamoylamino)phenoxy]-7-methoxyquinoline-6-carboxamide)

Compound VI: Nintedanib (methyl (3Z)-3-[({4-[N-methyl-2-(4-methylpiperazin-1-yl)acetamido]phenyl}amino)(phenyl)methylidene]-2-oxo-2·3-dihydro-1H-indole-6-carboxylate)

Compound VII: Dacomitinib ((E)-N-[4-(3-chloro-4-fluoroanilino)-7-methoxyquinazolin-6-yl]-4-piperidin-1-ylbut-2-enamide)

Compound VIII: Allitinib (N-[4-[[3-chloro-4-[(3-fluorobenzyl)oxy]phenyl]amino]quinazolin-6-yl]acrylamide)

Table 50 demonstrated that in the comparison between the microparticle composition and the nanoparticle composition, compound V and compound VI did not differ in transfer to the choroid and/or the sclera, whereas compound IV in the form of the nanoparticle composition exhibited moderately improved transfer and compound VII and compound VIII in the form of the nanoparticle composition exhibited drastically improved transfer.

Test Example 11 Pharmacokinetics of Nanoparticle Composition of Present Invention and Microparticle Composition of Comparative Example Administered at Single Dose by Ocular Instillation to Rat The nanoparticle composition of the present invention obtained in Example 145 and the microparticle composition of Comparative Example 16 were evaluated for their pharmacokinetics when administered at a single dose by ocular instillation to Brown-Norway rats. Each of the nanoparticle composition of the present invention obtained in Example 145 and the microparticle composition of Comparative Example 16 was administered at a single dose by ocular instillation to the right eye of each animal (n=2 for each condition). 1.5 hours after the ocular instillation, blood was collected. Then, the animal was euthanized, and both the eyeballs were excised. The eyeballs were washed, and a choroid/sclera sample was then harvested.

A given amount of a 50 vol % methanol solution was added to the harvested choroid/sclera sample, which was then homogenized. Acetonitrile was further added thereto, and the mixture was stirred. The sample was centrifuged, and the supernatant was harvested. A 0.1 vol % formic acid solution was added thereto to prepare an assay sample. The blood sample was centrifuged to harvest a plasma sample. Acetonitrile was added to the plasma sample, and the mixture was stirred. Then, the sample was centrifuged, and the supernatant was harvested. A 0.1 vol % formic acid solution was added thereto to prepare an assay sample.

The drug concentration in the assay sample was measured using a liquid chromatograph-tandem mass spectrometer (LC/MS/MS). The results are shown in Table 51 and FIG. 6.

TABLE 51

| Example No, or Comparative Example No. | Compound | Formulation concentration (mg/mL) | Mean particle size or D50 (nm) | Concentration in choroid and sclera (ng/g) | Concentration in choroid and sclera (ng/g)/ formulation concentration (mg/mL) |
|---|---|---|---|---|---|
| Example 145 | IX | 10.10 | 109 | 3590 | 355 |
| Comparative Example 16 | IX | 10.24 | 7200 | 1960 | 191 |

Compound IX: erlotinib hydrochloride (N-(3-ethynylphenyl)-6,7-bis(2-methoxyethoxy)quinazolin-4-amine Hydrochloride)

Table 51 demonstrated that in the comparison between the microparticle composition and the nanoparticle composition, the nanoparticle composition drastically improved transfer to the choroid and/or the sclera.

Test Example 12 Pharmacokinetics of Nanoparticle Composition of Present Invention and Microparticle Composition of Comparative Example Administered at Single Dose by Ocular Instillation to Rat The nanoparticle composition of the present invention obtained in Example 153 and the microparticle composition of Comparative Example 17 were evaluated for their pharmacokinetics when administered at a single dose by ocular instillation to Brown-Norway rats. Each of the nanoparticle composition of the present invention obtained in Example 153 and the microparticle composition of Comparative Example 17 was administered at a single dose by ocular instillation to the right eye of each animal (n=2 for each condition). Four hours after the ocular instillation, blood was collected. Then, the animal was euthanized, and both the eyeballs were excised. The eyeballs were washed, and a choroid/sclera sample was then harvested.

A given amount of a 50 vol % methanol solution was added to the harvested choroid/sclera sample, which was then homogenized. Acetonitrile was further added thereto, and the mixture was stirred. The sample was centrifuged, and the supernatant was harvested. A 0.1 vol % formic acid solution was added thereto to prepare an assay sample. The blood sample was centrifuged to harvest a plasma sample. Acetonitrile was added to the plasma sample, and the mixture was stirred. Then, the sample was centrifuged, and the supernatant was harvested. A 0.1 vol % formic acid solution was added thereto to prepare an assay sample.

The drug concentration in the assay sample was measured using a liquid chromatograph-tandem mass spectrometer (LC/MS/MS). The results are shown in Table 52 and FIG. 7.

4 compounds, and the mixture was diluted with saline containing 3.3 (w/v) % Tween 80 to prepare 7 types of intravenous dosing solutions. Each intravenous dosing solution was administered (0.5 mL/kg) to the tail vein of each Brown Norway rat. Twenty-four, 72 and 168 hours after the administration, blood was collected. Then, the animal was euthanized, and the eyeballs were excised. The eyeballs were washed, and a choroid/sclera sample was then harvested.

A given amount of a 50 vol % methanol solution was added to the harvested choroid/sclera sample, which was then homogenized. Acetonitrile was further added thereto, and the mixture was stirred. The sample was centrifuged, and the supernatant was harvested. A 0.1 vol % formic acid solution was added thereto to prepare an assay sample. The drug concentration in the assay sample was measured using a liquid chromatograph-tandem mass spectrometer (LC/MS/MS). The results are shown in Tables 53 and 54.

Table 53 shows the half-lives in the choroid and/or the sclera of the VEGF receptor inhibitors intravenously administered to the rats.

TABLE 52

| Example No, or Comparative Example No. | Compound | Formulation concentration (mg/mL) | Mean particle size or D50 (nm) | Concentration in choroid and sclera (ng/g) | Concentration in choroid and sclera (ng/g)/formulation concentration (mg/mL) |
|---|---|---|---|---|---|
| Example 153 | X | 11.31 | 147 | 88.3 | 7.81 |
| Comparative Example 17 | X | 11.85 | 7070 | 22.7 | 1.92 |

Compound X: gefitinib (N-(3-chloro-4-fluorophenyl)-7-methoxy-6-(3-morpholin-4-ylpropoxy)quinazolin-4-amine)

Table 52 demonstrated that in the comparison between the microparticle composition and the nanoparticle composition, the nanoparticle composition drastically improved transfer to the choroid and/or the sclera.

Test Example 13 Pharmacokinetics of Vascular Endothelial Growth Factor (VEGF) Receptor Inhibitor or Epidermal Growth Factor (EGF) Receptor Inhibitor Intravenously Administered at Single Dose to Rat N-[2-Chloro-4-(6,7-dimethoxyquinolin-4-yloxy)phenyl]-N'-(5-methylisoxazol-3-yl)urea hydrochloride hydrate, icotinib, allitinib, nazartinib, brigatinib, cabozantinib, glesatinib, 4-[(3-chloro-2-fluorophenyl)amino]-7-methoxyquinazolin-6-yl (2R)-2,4-dimethylpiperazine-1-carboxylate (AZD-3759), erlotinib, anlotinib, fruquintinib, dacomitinib, lenvatinib, rebastinib, nintedanib, poziotinib, sunitinib, lapatinib, tesevatinib, gefitinib, N-(3-chlorophenyl)-N-(6,7-dimethoxyquinazolin-4-yl) amine (AG-1478), N-[2-[[2-(dimethylamino)ethyl]methylamino]-5-[[4-(1H-indol-3-yl)-2-pyrimidinyl]amino]-4-methoxyphenyl]-2-propanamide (AZD-5104), axitinib, varlitinib, and avitinib (all compounds evaluated in sets are described) were evaluated for their pharmacokinetics when intravenously administered at a single dose to rats. Each compound was dissolved in DMA. Compound II was mixed with the DMA solutions of

TABLE 53

| Compound | Dose (mg/kg) | Half-life in choroid and sclera (hr) |
|---|---|---|
| Axitinib | 0.2 | 57.4 |
| Anlotinib | 0.2 | 141 |
| Cabozantinib | 0.2 | 65.8 |
| Glesatinib | 0.2 | 132 |
| Sunltinib | 0.2 | 187 |
| Nintedanib | 0.2 | 194 |
| Ponatinib | 0.1 | 191 |
| Fruquintinib | 0.2 | 32.5 |
| Lenvatinib | 0.2 | 42.3 |
| Rebastinib | 0.2 | not calculated |
| N-[2-Chloro-4-(6,7-dimethoxyquinolin-4-yloxy)phenyl]-N'-(5-methylisoxazol-3-yl)urea hydrochloride hydrate | 0.2 | 52.2, 60.1, 40.7, 60.2, 79.3, 103, 69.8 |

Table 54 shows the half-lives in the choroid and/or the sclera of the EGFR inhibitors intravenously administered to the rats.

TABLE 54

| Compound | Dose (mg/kg) | Half-life in choroid and sclera (hr) |
|---|---|---|
| Avitinib | 0.2 | 85.5 |
| Allitinib | 0.2 | 52.9, 40.1 |
| Icotinib | 0.2 | 64.8 |
| Erlotinib | 0.05 | 56.7, 71.2 |

TABLE 54-continued

| Compound | Dose (mg/kg) | Half-life in choroid and sclera (hr) |
|---|---|---|
| N-[2-[[2-(Dimethylamino)ethyl]methyl-amino]-5-[[4-(1H-indol-3-yl)-2-pyrimidinyl]amino]-4-methoxyphenyl]-2-propanamide (AZD-5104) | 0.2 | 195 |
| Gefitinib | 0.2 | 161 |
| Dacomitinib | 0.2 | 918, 486 |
| Tesevatinib | 0.2 | 305 |
| Nazartinib | 0.2 | 65.4 |
| Varlitinib | 0.2 | 46.1 |
| Brigatinib | 0.1 | 137 |
| Lapatinib | 0.2 | 246 |
| 4-[(3-Chloro-2-fluorophenyl)amino]-7-methoxyquinazolin-6-yl (2R)-2,4-dimethylpiperazine-1-carboxylate (AZD-3759) | 0.2 | 120 |
| Poziotinib | 0.2 | 31.9 |
| N-(3-Chlorophenyl)-N-(6,7-dimethoxyquinazolin-4-yl)amine (AG-1478) | 0.05 | 42.8 |

Test Example 14 Pharmacokinetics of Microparticle Composition of Comparative Example 1 Administered at Single Dose by Ocular Instillation to Rat The microparticle composition obtained in Comparative Example 1 was evaluated for its pharmacokinetics when administered at a single dose by ocular instillation (10 μL/eye, n=2 for each point in time) to rats. The microparticle composition was administered by ocular instillation to the right eye of each male Brown Norway rat. 0.5 to 96 hours after the ocular instillation, the rat was euthanized, and the right eyeball was excised. The eyeball was washed, and a choroid/sclera sample was then harvested.

A given amount of a 50 vol % methanol solution was added to the harvested choroid/sclera sample, which was then homogenized. Acetonitrile was further added thereto, and the mixture was stirred. The sample was centrifuged, and the supernatant was harvested. A 10 mmol/L ammonium acetate solution was added thereto to prepare an assay sample.

The drug concentration in the assay sample was measured using a liquid chromatograph-tandem mass spectrometer (LC/MS/MS). Also, the elimination half-life of compound III in the choroid and/or the sclera was calculated from change in the concentration of compound III in the choroid and/or the sclera.

The microparticle composition obtained in Comparative Example 1 had an elimination half-life of 29.7 hours in the choroid and/or the sclera when administered at a single dose by ocular instillation to the rats.

The invention claimed is:

1. Eye drops comprising a vascular endothelial growth factor (VEGF) receptor inhibitor in a nanoparticle form, wherein the VEGF receptor inhibitor is a compound represented by formula (II):

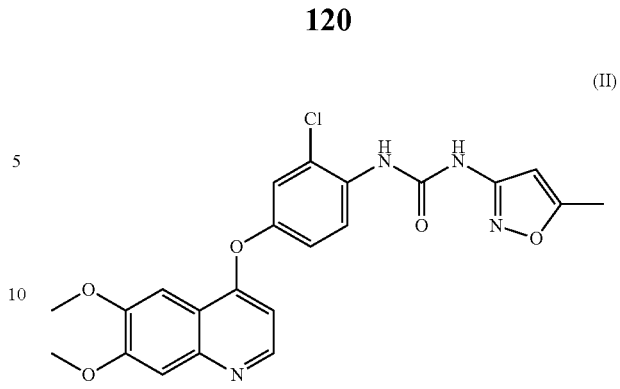

(II)

or a pharmaceutically acceptable salt thereof, or a hydrate or a solvate of the compound or the salt, and
the VEGF receptor inhibitor has a mean particle size of 400 nm or smaller.

2. The eye drops according to claim 1, wherein the content of the VEGF receptor inhibitor is 0.01 to 10 parts by weight per 100 parts by weight of the eye drops.

3. The eye drops according to claim 1, wherein the VEGF receptor inhibitor is a pharmaceutically acceptable salt of the compound represented by formula (II) or a hydrate or a solvate of the pharmaceutically acceptable salt.

4. The eye drops according to claim 1, wherein the VEGF receptor inhibitor has a mean particle size of 10 to 300 nm.

5. The eye drops according to claim 1, wherein the VEGF receptor inhibitor has a mean particle size of 10 to 200 nm.

6. The eye drops according to claim 1, further comprising at least one component selected from the group consisting of a thickening agent, a surfactant and a dispersion media.

7. The eye drops according to claim 6, wherein the thickening agent is at least one selected from the group consisting of carboxyvinyl polymer, carboxymethylcellulose calcium, carboxymethylcellulose sodium, povidone, partially hydrolyzed polyvinyl alcohol, hydroxypropylcellulose, hydroxypropylmethylcellulose, hydroxypropylmethylcellulose phthalate, hydroxyethylcellulose, amorphous cellulose, methylcellulose, magnesium aluminum silicate and triethanolamine.

8. The eye drops according to claim 6, wherein the surfactant is at least one selected from the group consisting of polyoxyethylene castor oil, polyoxyl 40 stearate, sucrose stearate, polyoxyethylene sorbitan monolaurate, polyoxyethylene sorbitan monostearate, polyoxyethylene sorbitan tristearate, polyoxyethylene sorbitan monooleate, polyoxyethylene sorbitan trioleate, sorbitan monolaurate, sodium lauryl sulfate, L-α-phosphatidylcholine (PC), 1,2-dipalmitoylphosphatidylcholine (DPPC), oleic acid, natural lecithin, synthetic lecithin, polyoxyethylene oleyl ether, polyoxyethylene lauryl ether, diethylene glycol dioleate, tetrahydrofurfuryl oleate, ethyl oleate, isopropyl myristate, glyceryl monooleate, glyceryl monostearate, glyceryl monoricinoleate, cetyl alcohol, stearyl alcohol, polyethylene glycol, tyloxapol, octylphenol ethoxylate, alkyl glucoside and poloxamer.

9. The eye drops according to claim 6, wherein the dispersion media is at least one selected from the group consisting of water, an alcohol, liquid paraffin, water containing a solute, an alcohol containing a solute and a liquid paraffin containing a solute.

10. The eye drops according to claim 6, wherein the dispersion media is water containing a solute.

11. The eye drops according to claim 9, wherein the solute is at least one selected from the group consisting of sodium chloride, glucose, glycerol, mannitol, sodium dihydrogen phosphate, dibasic sodium phosphate hydrate, sodium bicarbonate, trishydroxymethylaminomethane, citric acid hydrate, boric acid, borax and phosphoric acid.

12. The eye drops according to claim 1, further comprising at least one component selected from the group consisting of a preservative and an inclusion substance.

13. The eye drops according to claim 12, wherein the preservative is at least one selected from the group consisting of benzalkonium chloride, methyl parahydroxybenzoate, propyl parahydroxybenzoate, chlorobutanol, disodium edetate hydrate, chlorhexidine gluconate and sorbic acid.

14. The eye drops according to claim 12, wherein the inclusion substance is at least one substance selected from the group consisting of α-cyclodextrin, β-cyclodextrin, 2-hydroxypropyl-γ-cyclodextrin and γ-cyclodextrin.

15. The eye drops according to claim 1, wherein the eye drops are in the form of a suspension formulation.

16. The eye drops according to claim 1, wherein the eye drops are a therapeutic agent for an ophthalmic disease, and the ophthalmic disease is a vascular endothelial growth factor (VEGF)-related disease.

17. The eye drops according to claim 16, wherein the VEGF-related disease is wet age-related macular degeneration, dry age-related macular degeneration, choroidal neovascularization, myopic choroidal neovascularization, branch retinal vein occlusion, macular edema, macular edema following central retinal vein occlusion, diabetic macular edema, proliferative diabetic retinopathy, neovascular glaucoma, angioid streaks of the retina, retinopathy of prematurity, Coats disease, central retinal vein occlusion, cystoid macular edema, vitreous hemorrhage caused by diabetic retinopathy, Eales disease, central serous chorioretinopathy, epiretinal membrane, uveitis, multifocal choroiditis, anterior ischemic optic neuropathy, corneal neovascularization, pterygium, intraocular melanoma, vasoproliferative tumor of the retina, radiation retinopathy, tuberous sclerosis, conjunctival squamous cell carcinoma or ocular hypertension.

18. The eye drops according to claim 16, wherein the VEGF-related disease is wet age-related macular degeneration, myopic choroidal neovascularization, branch retinal vein occlusion, central retinal vein occlusion, macular edema following central retinal vein occlusion, diabetic macular edema, proliferative diabetic retinopathy, neovascular glaucoma or retinopathy of prematurity.

19. A freeze-dried product for producing eye drops, wherein
the freeze-dried product comprises a vascular endothelial growth factor (VEGF) receptor inhibitor in a nanoparticle form,
the VEGF receptor inhibitor is a compound represented by formula (II):

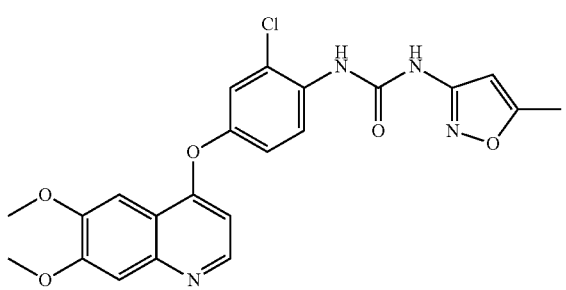

(II)

or a pharmaceutically acceptable salt thereof, or a hydrate or a solvate of the compound or the salt, and
the VEGF receptor inhibitor has a mean particle size of 400 nm or smaller.

20. A method for producing eye drops, comprising dispersing a freeze-dried product into a dispersion media, wherein
the freeze-dried product comprises a vascular endothelial growth factor (VEGF) receptor inhibitor in a nanoparticle form,
the VEGF receptor inhibitor is a compound represented by formula (II):

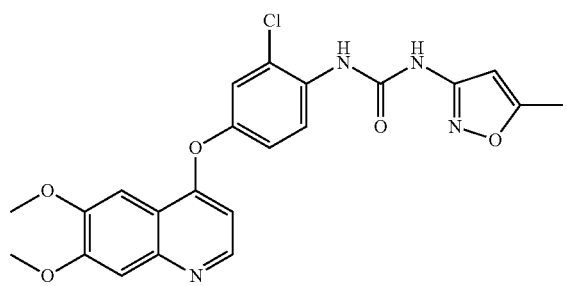

(II)

or a pharmaceutically acceptable salt thereof, or a hydrate or a solvate of the compound or the salt, and
the VEGF receptor inhibitor has a mean particle size of 400 nm or smaller.

21. A freeze-dried product for producing eye drops, wherein
the freeze-dried product comprises a vascular endothelial growth factor (VEGF) receptor inhibitor,
the VEGF receptor inhibitor is a compound represented by formula (II):

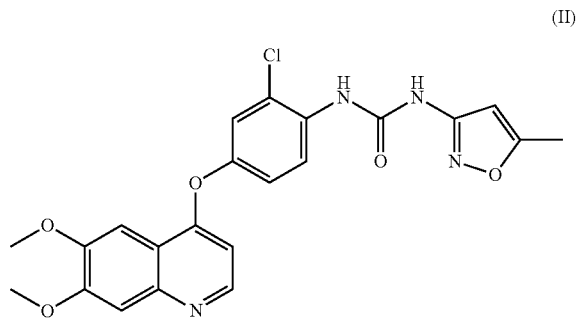

(II)

or a pharmaceutically acceptable salt thereof, or a hydrate or a solvate of the compound or the salt,
the VEGF receptor inhibitor in the eye drops produced from the freeze-dried product is in a nanoparticle form, and
the VEGF receptor inhibitor has a mean particle size of 400 nm or smaller.

22. A method for producing eye drops, comprising dispersing a freeze-dried product into a dispersion media, wherein
the freeze-dried product comprises a vascular endothelial growth factor (VEGF) receptor inhibitor, the VEGF receptor inhibitor is a compound represented by formula (II):

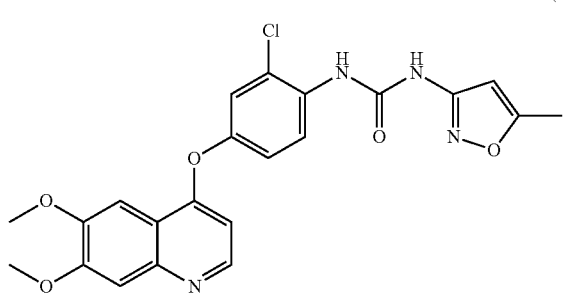

(II)

or a pharmaceutically acceptable salt thereof, or a hydrate or a solvate of the compound or the salt, the VEGF receptor inhibitor in the eye drops produced from the freeze-dried product is in a nanoparticle form, and the VEGF receptor inhibitor has a mean particle size of 400 nm or smaller.

23. The eye drops according to claim 1, wherein the VEGF receptor inhibitor is in a crystalline form.

24. The eye drops according to claim 1, wherein the VEGF receptor inhibitor is N-[2-Chloro-4-(6,7-dimethoxyquinolin-4-yloxy)phenyl]-N'-(5-methylisoxazol-3-yl)urea hydrochloride hydrate.

25. A vascular endothelial growth factor (VEGF) receptor inhibitor in a nanoparticle form for the treatment of an ophthalmic disease, wherein the VEGF receptor inhibitor is a compound represented by formula (II):

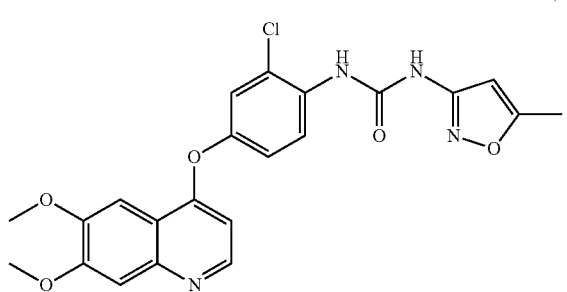

(II)

or a pharmaceutically acceptable salt thereof, or a hydrate or a solvate of the compound or the salt, and the VEGF receptor inhibitor has a mean particle size of 400 nm or smaller.

26. The VEGF receptor inhibitor according to claim 25, wherein the VEGF receptor inhibitor is in a crystalline form.

27. The VEGF receptor inhibitor according to claim 25, wherein the ophthalmic disease is a vascular endothelial growth factor (VEGF)-related disease.

28. The VEGF receptor inhibitor according to claim 27, wherein the VEGF-related disease is wet age-related macular degeneration, dry age-related macular degeneration, choroidal neovascularization, myopic choroidal neovascularization, branch retinal vein occlusion, macular edema, macular edema following central retinal vein occlusion, diabetic macular edema, proliferative diabetic retinopathy, neovascular glaucoma, angioid streaks of the retina, retinopathy of prematurity, Coats disease, central retinal vein occlusion, cystoid macular edema, vitreous hemorrhage caused by diabetic retinopathy, Eales disease, central serous chorioretinopathy, epiretinal membrane, uveitis, multifocal choroiditis, anterior ischemic optic neuropathy, corneal neovascularization, pterygium, intraocular melanoma, vasoproliferative tumor of the retina, radiation retinopathy, tuberous sclerosis, conjunctival squamous cell carcinoma or ocular hypertension.

29. The VEGF receptor inhibitor according to claim 25, wherein the VEGF receptor inhibitor is a pharmaceutically acceptable salt of the compound represented by formula (II) or a hydrate or a solvate of the pharmaceutically acceptable salt, and the pharmaceutically acceptable salt is hydrochloride, hydrofluoride, hydrobromide, hydroiodide, sulfate, phosphate, nitrate, perchlorate, acetate, citrate, fumarate, succinate, tartrate, oxalate, maleate, malate, lactate, ascorbate, mesylate, trifluoromethanesulfonate, ethanesulfonate, benzenesulfonate tosylate, glycinate, phenylalanate, glutamate or aspartate.

30. The VEGF receptor inhibitor according to claim 25, wherein the VEGF receptor inhibitor is a pharmaceutically acceptable salt of the compound represented by formula (II) or a hydrate or a solvate of the pharmaceutically acceptable salt, and the pharmaceutically acceptable salt is hydrochloride.

31. The VEGF receptor inhibitor according to claim 25, wherein the VEGF receptor inhibitor is N-[2-Chloro-4-(6,7-dimethoxyquinolin-4-yloxy)phenyl]-N'-(5-methylisoxazol-3-yl)urea hydrochloride hydrate.

32. The eye drops according to claim 1, wherein the eye drops are a therapeutic agent for an ophthalmic disease, and the ophthalmic disease is wet age-related macular degeneration, diabetic macular edema, branch retinal vein occlusion, central retinal vein occlusion, or proliferative diabetic retinopathy.

33. The VEGF receptor inhibitor according to claim 25, wherein the VEGF receptor inhibitor has a mean particle size of 10 to 300 nm.

* * * * *